(12) United States Patent
Alberte et al.

(10) Patent No.: US 6,841,718 B2
(45) Date of Patent: Jan. 11, 2005

(54) TRANSGENIC PLANTS INCORPORATING TRAITS OF *ZOSTERA MARINA*

(75) Inventors: Randall S. Alberte, Falmouth, ME (US); Robert Smith, Falmouth, ME (US)

(73) Assignee: Cerno Biosciences LLC, Fort Myers, FL (US)

( * ) Notice: Subject to any disclaimer, the term of this patent is extended or adjusted under 35 U.S.C. 154(b) by 15 days.

(21) Appl. No.: 09/854,122

(22) Filed: May 10, 2001

(65) Prior Publication Data

US 2002/0016980 A1 Feb. 7, 2002

Related U.S. Application Data

(60) Provisional application No. 60/202,529, filed on May 10, 2000.

(51) Int. Cl.[7] .................. C12N 15/29; C12N 15/82; A01H 5/00
(52) U.S. Cl. .................. 800/279; 435/320.1; 435/419; 435/252.3; 536/23.6; 800/278
(58) Field of Search .................. 435/320.1, 419, 435/252.3; 536/23.6, 23.2; 800/278, 279, 298

(56) References Cited

U.S. PATENT DOCUMENTS

| | | | |
|---|---|---|---|
| 5,384,176 A | 1/1995 | Zimmerman et al. | 428/68 |
| 5,607,741 A | 3/1997 | Zimmerman et al. | 428/68 |
| 2001/0051274 A1 | 12/2001 | Alberte et al. | 428/411.1 |

OTHER PUBLICATIONS

Varin et al. Expression of flavonol sulfotransferase gene in canola, potato and tobacco. Bulletin de liaison– Groupe Polyphenols 1992, vol. 16, part 2, pp. 305–308.*

Hoeren et al. Evidence for a role for AtMYB2 in the induction of the Arabidopsis alcohol dehydrogenase gene (ADH1) by low oxygen. Genetics, Jun. 1988, vol. 149, pp. 479–490.*

Xu et al. Expression of a late embryogenesis abundant protein gene, HVA1, from barley confers tolerance to water deficit and salt stress in transgenic rice. Plant Physiology, 1996, vol. 110, pp. 249–257.*

Varin et al. Novel flavonol 3–sulfotransferase. The Journal of Biological Chemistry, Jan. 25, 1992, vol. 267, No. 3, pp. 1858–1863.*

Rhoads et al. Regulation of the cyanide–resistant alternative oxidase of plant mitochondria. Identification of the cysteine residue involved in alpha–keto acid stimulation and inter-subunit, J. Biol. Chem., Nov. 1998, vol. 273, No. 46, pp. 30750–30756.*

Varin et al. (1997) "Sulfation and Sulfotransferases 6: Bio-schemistry and molecular biology of plant sulfotrans-ferases," *The FASEB Journal*, vol. 11, pp. 517–525.

Todd et al. (1993) "The Antifouling Activity of Natural And Synthetic Phenolic Acid Sulphate Esters," *Phytochemistry*, vol. 34, No. 2, pp. 401–404.

International Search Report, PCT Application No. PCT/US 01/15412, mailed Mar. 5, 2002.

* cited by examiner

*Primary Examiner*—David T. Fox
*Assistant Examiner*—Cynthia Collins
(74) *Attorney, Agent, or Firm*—Foley Hoag LLP

(57) ABSTRACT

The invention provides methods and compositions related to transgenic plants which incorporate genetic traits of the marine eelgrass *Zostera marina*. These traits include patho-gen resistance, which may be conferred by stimulating zosteric acid biosynthesis.

31 Claims, 31 Drawing Sheets

Figure 3

| Primer name | Primer Sequence (from 5' to 3') | Protein sequence |
|---|---|---|
| Degenerate: | | |
| Z-ST-P14 (5'primer) | TAYCCIAARAGYGGIACIACITGG | YPKSGTTW |
| Z-ST-P16 (3'primer) | YTTCCARTCICCIIIIIIICCYTTYCT | RKGXXGDWK |
| Z-ST-P17 (3'primer) | YTTCCARTCICCIIIIIIICCYTTIGC | RKGXXGDWK |
| Gene specific: | | |
| Z-ST-P18 (5'primer) | ATCTGATTAACCCCGACAAGTTATTGG | |
| Z-ST-P19 (3'primer) | CCAATAACTTGTCGGGGTTAATCAGAT | |
| Z-ST-P26 (5'primer) | ATCCGAGCTCGATGGCTGGAATTTTAGC TTTGGAG | |
| Z-ST-P25 (3'primer) | CTAGAAGCTTACGAATGAATACGATAA TAAAC | |

Figure 4

```
ACGCGGGGAATAACTGGAATCGCTGTTGCTTGCTAGCTACCACTGATAATGGCTGGAATTTTAGCTTTGGAGAAATGTTTCGGATCCAAG  90
 T  R  G  I  T  G  I  A  V  A  C  .  L  P  L  I  M  A  G  I  L  A  L  E  K  C  F  G  S  K

AATGAGCAAGAGAAGGAAGAAGATTCCAAAATGTACAAGAGATATAGAGAGATTGTTTCTTCACTTCCCTCGAATGATTATTGGGGGGAT  180
 N  E  Q  E  K  E  E  D  S  K  M  Y  K  R  Y  R  E  I  V  S  S  L  P  S  N  D  Y  W  G  D

ACCATGAGGTTGTACAAGGGATTTTGGCAAATGGGATATCTTGTACCTGGTATCATGGCTTTCGAAGATAATTTCAAGGCTCGAGAGACG  270
 T  M  R  L  Y  K  G  F  W  Q  M  G  Y  L  V  P  G  I  M  A  F  E  D  N  F  K  A  R  E  T

GACATTATCCTTACGACTCTTCCAAAGGCTGGAACGACATGGACGAAGGCACTGACGTTTGCCATCCTAACACGAGATGTTAACCACCCA  360
 D  I  I  L  T  T  L  P  K  A  G  T  T  W  T  K  A  L  T  F  A  I  L  T  R  D  V  N  H  P

TCATCACCGACACATCCACTTTTGTTCTTCAACCCTCATTCGTGTGTTCAAAATTTGGAGTATTTGTACATGGGTAGAGAAAATACGATG  450
 S  S  P  T  H  P  L  L  F  F  N  P  H  S  C  V  Q  N  L  E  Y  L  Y  M  G  R  E  N  T  M

CCAGACCTCGATATGTTGAATGAATCGCCGAGGTTGTTTGCCGGACACATCCCATACTCTTTGTTGCCGGCGTCTGTTTTGAAATCGGGA  540
 P  D  L  D  M  L  N  E  S  P  R  L  F  A  G  H  I  P  Y  S  L  L  P  A  S  V  L  K  S  G

ACAAAAATCATCAATATAAGCCGCAACCGTAAGAGTACATTTGTGTCTTTTTGGAAATTTGGCAATCTGATTAACCCCGACAAGTTATTG  630
 T  K  I  I  N  I  S  R  N  R  K  S  T  F  V  S  F  W  K  F  G  N  L  I  N  P  D  K  L  L

GACCTCGAAAAGAGCGTTGATATCTTCGCATCGGGAATCTCCTTTTGTGGACCGGAATGGAATTTCCAAGCGGAGTTCACCAATGCGGCG  720
 D  L  E  K  S  V  D  I  F  A  S  G  I  S  F  C  G  P  E  W  N  F  Q  A  E  F  T  N  A  A

TCTACTAATTCAAACTTGCTATTGTTGAGTTACGAAGAAATGTTAGAGAAGCCAGTTGAAAATGTGAAGAAGCTAGCTGAGTTCATGGGA  810
 S  T  N  S  N  L  L  L  L  S  Y  E  E  M  L  E  K  P  V  E  N  V  K  K  L  A  E  F  M  G

TGTGGGTTCACAGACGATGAGGAGAAACAAGGGATTGTTGATGAGATAGTTAAACTTTGTAGCTTCGACAATCTGAAGAATCAACAGGTG  900
 C  G  F  T  D  D  E  E  K  Q  G  I  V  D  E  I  V  K  L  C  S  F  D  N  L  K  N  Q  Q  V

AACAAAAACGGATCAAGCTACAATTCGAAAATCGACAACAAGCATTTCTTCAGGAAAGGTGAGGTGAGAGATTGGGCAAACTATCTAACG  990
 N  K  N  G  S  S  Y  N  S  K  I  D  N  K  H  F  F  R  K  G  E  V  R  D  W  A  N  Y  L  T

TCGGAAATGATTAAGAAACTGGAGACGGCCGGAAAAATAAATGAATCAGAGTAAAAGCATTTATTATCGTGAAATAAGAATCTTACATGA  1080
 S  E  M  I  K  K  L  E  T  A  G  K  I  N  E  S  .  K  H  L  L  S  .  N  K  N  L  T  .

AACTTCTGAAATCTTAATAATTACTGTGAGAAATCGAACTAAATATCTCTTTGTTTATTATCGTATTCATTCGTAATAAATAATTTCATT  1170
 N  F  .  N  L  N  N  Y  C  E  K  S  N  .  I  S  L  C  L  L  S  Y  S  F  V  I  N  N  F  I

TTGTTAAAAAAAAAAAAAAAAA  1192
 L  L  K  K  K  K
```

Figure 5

| | | |
|---|---|---|
| Z. marina | MAGILALEKCFGSKNEQEKEEDSKHYKRYREIVSSLPSNDYK-GDTMRLYKSFWQMGYLV | 59 |
| B. napus | MSS---------SSSVPDYLRDENLTQKTKDLISSLPSEKGWLVCQMYQFQGRWHTQALL | 51 |
| A. thaliana | MSS---------SSSVPAYLGDEDLTQETRALISSLPKEKGWLVSEIYEFQGLWHTQAIL | 51 |
| F. bidentis | MET---------TKT--QFESHAEMIKKLPQHTCS---SLKGRIT--LYKYQDFAGLQNNI | 45 |
| H. sipiens | MELIQD-----TSRPPLEYVKGVPLIKYFAEALGPL------------------------ | 31 |

I

| | | |
|---|---|---|
| Z. marina | PGIMAFEDNFKARETDIILTTLPKAGTTWTKALTFAILTRD-VNHPSSPTHPLLFFNPHS | 118 |
| B. napus | QGILTCQKHFEAKDSDIILVTNPKSGTTWLKALVFALINRHKFPVYSV--IILSCYQSAL | 109 |
| A. thaliana | QGILICQKRFEAKDSDIILVTNPKSGTTWLKALVFALLNRHKFPVSSGNHPLLVTNPHL | 111 |
| F. bidentis | EGAILAQOSFKARPDDVFLCSYPKSGTTWLKALAYAIVTREKFDEFTS---PLLTNIPHN | 102 |
| H. sipiens | -------QSFQARPDDLLINTYPKSGTTWVSQILDMIYQGGDLEKCNRAPI-------YV | 77 |

II

| | | |
|---|---|---|
| Z. marina | CVQNLEYLYMGRENTHPDLDHLN-ESPRLFAGHIPYSLLFASVIKSGTKIINISRNRKST | 177 |
| B. napus | LVPFLGRSLL----RSPDFDFSQLSPRLMNTHISHLSLFESVKSSSCKIVYCCRNPKDM | 165 |
| A. thaliana | LVPPLGVYY----ESPDFDFSSLPSPRLMNTHISHLSLFESVKSSSCK-IVYCCRNPKDM | 167 |
| F. bidentis | CIPYIDKDLK----KIVENQNNSCFTP--MATHMFYHVLEKSILALNCKMVYIYRNIKDV | 156 |
| H. sipiens | RVPFLDVNDPGEPSGLETLK--DTPPPRLIKSHLPLALLPQTLLDQKVKVYVARNPKDV | 135 |

III

| | | |
|---|---|---|
| Z. marina | FVSFNKFGNLINPDKLLD--LEKSVDIFASGISFCGPEWNFQAEFINBASINSN-LPLLS | 234 |
| B. napus | FVSLWHFGKKLAPEETADYPIEKAVEABCQGKFIGGPFWDHVLEYWYASLENPNKVLFVS | 225 |
| A. thaliana | FVSLWHFGKKLAPEETADYDIEKAVEARCEGKFIGGFFWDHILEYWYASRENPNKVLFVT | 227 |
| F. bidentis | IVSFYHFGREITKLPLEBAPFEEAFDEFYHGISQFGPYWDELLGYWKASLERFEVILFLK | 216 |
| H. sipiens | AVSYYHF-HRHEKAHPEPGTWDSFLEKFMAGEVSYGSWYQHVQFWA--ELSRTHPVLYLF | 192 |

IV

| | | |
|---|---|---|
| Z. marina | YEEMLEKBVENVKKLAEFMSCGFTDDEEKQGIVDEIVKLCSFDWLKHQQVNKNGS--SYN | 292 |
| B. napus | YEEPKKKTGETIKRIAEFLICGLVGEEE----VRAIVKLCSFESLSSLEVNRESKLFS-- | 279 |
| A. thaliana | YEELKKQTEVEMKRIAEFLECGFIEEEE----VREIVKLCSFESLSNLEVNKEGKLPN-- | 281 |
| F. bidentis | YEDVKKDPTSNVKRLAEFIGYPFTFEEEKEGVIESLIKLCSFEWLSNLEVNKSGHSKGFL | 276 |
| H. sipiens | YEDMKENPKREIQKILEFVGRSLPEET-----MDFHVQBTSFKEMKKNPMTNYTTVBQEL | 247 |

| | | |
|---|---|---|
| Z. marina | SKIDNKHFFRKGEVRDWANYLTSEMIKKLETA--GKIMESE | 331 |
| B. napus | G-METRAFFRKGEVGGWRDTLIESLAEVIDRTIEBKFQGSGLKFSC | 324 |
| A. thaliana | G-LETKTFFRKGEIGGWRDSFE | 302 |
| F. bidentis | P-LENRLYFRKAKDGDWKNYIDEMTBKIDKLIDELSATGLVLK | 320 |
| H. sipiens | MDHSISPFMRKGMAGDWKTTFTVAQNERFDADYABKMAGCSLSFRSEL | 295 |

Figure 6

```
[AG GTAAGT]
 | | | | | |
AG GTGATTACTGCTTCTTTTTTAGTGAAGTTTTATTTTGTGTCGCGGTCGTGCTAAGGCACG   60

GCAAAAAACTGACTTGTAGGAACGGATTTAGCGACGGCTCTAAATCTGAAGAAGAATTTT   120

GCTAAGGGTCATTTTCCGTTCTTAATTAATAATTAGCGACGGCTTTTGATCATTGGGGAC   180

GGATTCTGGCCGTCCCTAAAGATCGTTTTTCTTGTAGTGAGGGCGGTATATTAATTCTCT   240

CTTCAATCGTCGAAGAAAAACACGTACATACTGAAGATTTATTTTGTGTATATATAG GC   297
                                                    | | | | | |
                                                    [TTTTGCAG GC]
```

Figure 7
Subcloning of full-length ST gene onto expression vector:
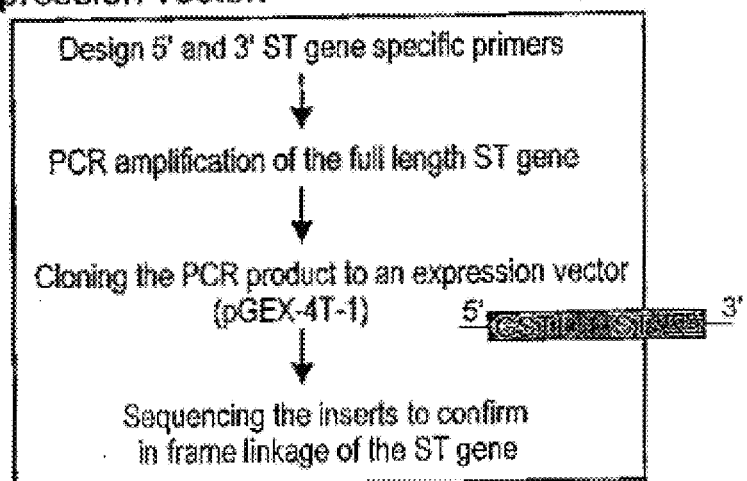
Expression of ST fusion protein:
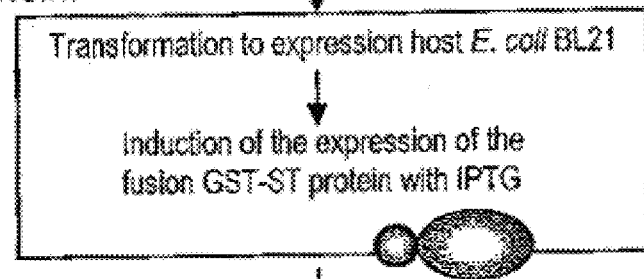
Determination of enzymic activity:
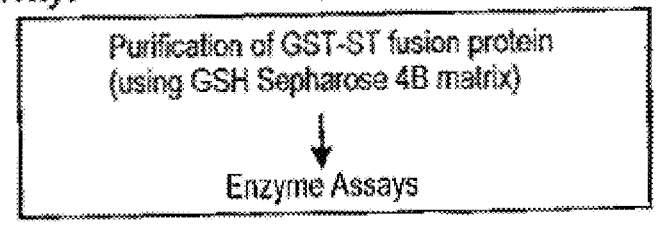

ST catalyzed sulfur transferation:

Figure 10

| Substrate | Sp. Enzyme Activity (nmol/min/mg) | | |
|---|---|---|---|
| | Z. marina ST | Flaveria ST | Rat Dopa/tyrosine ST |
| Quercetin | 60-100 | 0.27 | |
| P-nitrophenol | 0.3 | | 125 |

Figure 11

| Primer Names | Primer sequences (From 5' to 3') | Corresponding conserved Protein Sequences |
|---|---|---|
| 5' primers: | | |
| Z-ADH-P1 | GTIGCITGGGARSCIGGIAARCC | VAWEA(P)GKP |
| Z-CH-P1 | CARRAIATGGTITTYACIGTITAYGG | QD(K)MVFTVYG |
| Z-PAL-P1 | AARCAYCAYCCIGGICARATIGARGC | KHHPGQIEA |
| 3' primers: | | |
| Z-ADH-P5 | TTRTARTTICCRAARAAIGTICCYTT | KGTFFGNYK |
| Z-CH-P4 | GGIARIGCIARDATDATICCGIIRCA | CPGIILALP |
| Z-PAL-P4 | YTCIACYTCYTTIGGIARIACIGC | AVLPKEVE |

Figure 12

| Gene Name | Size of the genes | Size of the partial clone | Strain File Designation |
|---|---|---|---|
| Alcohol dehydrogenase (ADH) | ~1300 bp | 938 bp | S19 |
| Cinnamate 4-hydroxylase (CH) | ~1500 bp | 1083 bp | S20 |
| Phenylalanine ammonia lyase (PAL) | ~2000 bp | 910 bp | S21 |
| Peroxidase (POX) | ~950 bp | 590 bp | S2 |

Figure 13

```
GTGGCGTGGGAACCGGGGAAACCATTGGTTATGGAGGAAGTTGACGTCGCACCACCGCAGAAAGATGAGGTTCGTGTCAAGATCAAGTTC  90
 V  A  W  E  P  G  K  P  L  V  M  E  E  V  D  V  A  P  P  Q  K  D  E  V  R  V  K  I  K  F

ACGGCACTCTGTCACACCGATGTCTTCTTTTGGGAAGCCAAGGGCCAAACGCCGGTGTTCCCTCGTATCTTCGGTCACGAGGCCGGAGGG  180
 T  A  L  C  H  T  D  V  F  F  W  E  A  K  G  Q  T  P  V  F  P  R  I  F  G  H  E  A  G  G

ATTGTGGAAAGTGTCGGGGAAGGCGTGACCGACGTCGTGCCGGGAGATCACGTCCTCCCAGTTTTCACTGGGGAATGTAAAGAATGCCGC  270
 I  V  E  S  V  G  E  G  V  T  D  V  V  P  G  D  H  V  L  P  V  F  T  G  E  C  K  E  C  R

CACTGCAAATCAGAAGAGAGTAATATGTGCGATCTCCTTCGAATAAACACCGATCGGGGTGTCATGCTCGCTGATGGAAAAATCTAGATTC  360
 H  C  K  S  E  E  S  N  M  C  D  L  L  R  I  N  T  D  R  G  V  M  L  A  D  G  K  S  R  F

TCCATCAAAGGCAAACCAATCTACCATTTTGTCGGAACCTCCACTTTCAGTGAATACACTATTGTGCATGTTGGTTGTTTGGCTAAGATC  450
 S  I  K  G  K  P  I  Y  H  F  V  G  T  S  T  F  S  E  Y  T  I  V  H  V  G  C  L  A  K  I

AACCCTGAAGCACCTCTTGACAAAGTTTGCATTCTTAGCTGTGGAATTTCCACCGGATTTGGCGCGACGGTTAATGTGGCAAAGCCGACC  540
 N  P  E  A  P  L  D  K  V  C  I  L  S  C  G  I  S  T  G  F  G  A  T  V  N  V  A  K  P  T

AAAGGTTCTTCCGTCGCCGTCTTCGGCCTGGGAGCCGTCGGTCTTTCTGCTTGTGAAGGAGCGAGGGTTTCTGGAGCGGCGAGAATAATC  630
 K  G  S  S  V  A  V  F  G  L  G  A  V  G  L  S  A  C  E  G  A  R  V  S  G  A  A  R  I  I

GGTATCGACATCAATCCTGATAGATTTGAAGAAGCTAGGAAATTCGGGTGCACTGATTTTGTGAATCCAAAGGAACACACCAAACCTGTT  720
 G  I  D  I  N  P  D  R  F  E  E  A  R  K  F  G  C  T  D  F  V  N  P  K  E  H  T  K  P  V

CAAGAGGTTATTGCTGAAATGACCGACGGTGGAGTAGATCGTTGTTTGGAATGTACTGGTAACATCAACGCCATGATTTCTGCATTCGAA  810
 Q  E  V  I  A  E  M  T  D  G  G  V  D  R  C  L  E  C  T  G  N  I  N  A  M  I  S  A  F  E

TGCGTCCATGATGGATGGGGTGTGGCTGTTCTGGTGGGAGTTCCTCAGAAAGATGCAGTTTTCAAGACTCACCCACTGCAATTTCTGAGT  900
 C  V  H  D  G  W  G  V  A  V  L  V  G  V  P  Q  K  D  A  V  F  K  T  H  P  L  Q  F  L  S

GAAAAAACACTCAAGGGCACCTTACTTCGGCAACTATAA  939
 E  K  T  L  K  G  T  L  L  R  Q  L
```

Figure 14

```
Z. Marina    V---------------------AWEPGKPLVMEEVDVAPPQKDEVRVKIKETALCHTDVFFK  41
Arabidopsis  MSTTQIIRC------KAAVAWEAGKPLVIEEVEVAPPQKHEVEIKILPTSLCHTDLYFK  54
Corn         KATAGKVIKC------KAAVAWEAGKPLSEEVEVAPPCAMEVRVKILPTSLCHTDVYFH  54
E. Coli      MKS-----------RAAVAFAPGKPLEIVEIDVAPPKKGEVLIKVTHTGVCHTDAFTL  47

Z. Marina    EAKGQTPVFPRIFGHEAGGIVESVGEGVTDVVPGDHVLPVFTGECKECRHCKSEESNMCE  101
Arabidopsis  EAKGQTPLFPRIFGHEAGGIVESVGEGVTDLQPGDHVLPIFTGECGECRHCHSEESNMCE  114
Corn         EAKGQTPVFPRIFGHEAGGIESVGEGVTDVAPGDHVLPVFTGECKECAHCKSAFSNMCE  114
E. Coli      SGDDPEGVFPVVLSHEGAGVVVEVGEGVTSVKPGDHVIPLYTAECGECEFCRSGKTNLCV  107

Z. Marina    LLRINTDRGVMLADGKSRFSIKGKPIYHFVGTSTFSEYTIVHVGCLAKINPEAPLDKVCI  161
Arabidopsis  LLRINTERGGMIHDGESRFSINGKPIYHFLGTSTFSEYTVVFSGQVAKINPDAPLDKVCI  174
Corn         LLRINTDRGVMIGDGKSRFSINGKPIYHFVGTSTFSEYTVMHVGCVAKINPQAPLDKVCV  174
E. Coli      AVEETQGKG-LMPDGTTRFSYNGQPLYHYMCSTFSEYTVJAEVSLAKINPEANHEHVCL  166

Z. Marina    LSCGISTGFGATVNVAKPTKGSSVAVFGLGAVGLSACEGARVSGAARIIGIDINPDRFEE  221
Arabidopsis  VSCGLSTGLGASLNVAKPKKGQSVAIFGLGAVGLGAAEGARIAGASRIIGVDFNSRRFDQ  234
Corn         LSCGISTGLGASINVAKPPKGSTVAVFGLGAVGLAAAEGARIAGASRIIGVDLNFSSFEF  234
E. Coli      LGCGVTGIGAVHNTAKVQPGDSVAVFGLGAIGLAVVQGARQKAGRIIAISTNPKEDL  226

Z. Marina    ARKFGCTDFVNPKEHTKPVQEVIAEMTDGGVDRCLECTGNINAMISAFECVHDGWGVAVL  281
Arabidopsis  AKEFGVTECVNPKDHDKFIQQVIAEMTDGGVDRSVECTCSVQAMIQAFECVHDGWGVAVL  294
Corn         ARKFGCTEFVNPKDFNKPVQEVLAEMTNGGVDRSVECTGNINAMIOAFECVHDGWGVAVL  294
E. Coli      AHRFGATDCINPNDYDKPIKDVLLDINKWGIDHTFECIGNVFVMRAALESAGRGWGQSVI  286

Z. Marina    VGVFQKDAVFKTHPLQFLSEKTLKGT-----------L-----------308
Arabidopsis  VGVFSKDDAFKTHPMNFLMERTLKGTFFGNYKFKTDIFGVVEKYMNKELELEKFITHTVP  354
Corn         VGVPHKDAEEKTHPMNFLMERTLKGTFFGNYKPRTDLPNJVELYMKKELEVEKFITHSVP  354
E. Coli      IGVAVAGQEISTRDFQLVTGRVWKGSAFGGVNGESQLPGMVEDAMKGDIDDEPFVTHTHS  346

Z. Marina    IRQL----------------.                                        313
Arabidopsis  FSEINKAFDYMLKGESIRCI--UTMGA                                   379
Corn         FAEINKAFNLMAKGEGIRCI--IRMEN                                   379
E. Coli      LDEINDAFDLMHEGKSIFTV--IE--Y                                   369
```

Figure 15

```
CAGGAGATGGTGTTCACGGTGTATGGCGATCACTGGAGGAAGATGCGGAGGATCATGACTGTGCCTTTTTTCACCAACAAGGTCGTCCAA   90
 Q  E  M  V  F  T  V  Y  G  D  H  W  R  K  M  R  R  I  M  T  V  P  F  F  T  N  K  V  V  Q

CAGTACCGATTCGGATGGGAGGATGAGACGAAAAGAGTCGTGGAGGATTTAGAGGCCAACCCCAAAGCCGCGACGGAAGGGACTGTGCTG  180
 Q  Y  R  F  G  W  E  D  E  T  K  R  V  V  E  D  L  E  A  N  P  K  A  A  T  E  G  T  V  L

AGGAGGAGGTTGCAGCTGATGATGTACAATAATCTGTACAGAATCATGTTTGACCGGAGGTTCGAGAGTGAAGATGATCCTTTGTTTCTG  270
 R  R  R  L  Q  L  M  M  Y  N  N  L  Y  R  I  M  F  D  R  R  F  E  S  E  D  D  P  L  F  L

AAGCTCAAGGCGTTGAACGGGGAGAGGAGTAAACTGGCGCAGAGCTTCGACTACAACTACGGAGATTTCATCCCCATCTTGAGACCTTTT  360
 K  L  K  A  L  N  G  E  R  S  K  L  A  Q  S  F  D  Y  N  Y  G  D  F  I  P  I  L  R  P  F

CTGAAAGGCTACCTTAAGAAATGCCAAGAGTTGAAGGACAATCGAATTAAGCTGTTTAAGGATTACTTCGTCGACGAGAGGAGGAAGTTG  450
 L  K  G  Y  L  K  K  C  Q  E  L  K  D  N  R  I  K  L  F  K  D  Y  F  V  D  E  R  R  K  L

TTAGGTTCGATGACCTCCAAGTCGGAACAGCAGAAGTGCGCCATCGATCATATTCTGGAAGCCGAGAAGAAAGGAGAGATCAATGAGGAC  540
 L  G  S  M  T  S  K  S  E  Q  Q  K  C  A  I  D  H  I  L  E  A  E  K  K  G  E  I  N  E  D

AACGTCCTGTACATCGTGGAGAACATCAACGTCGCCGCCATTGAGACGACACTATGGTCGGTGGAGTGGGGGGTGGCGGAGTTGGTGAAC  630
 N  V  L  Y  I  V  E  N  I  N  V  A  A  I  E  T  T  L  W  S  V  E  W  G  V  A  E  L  V  N

CACCCCGAAATCCAGAAGAAACTGAGACACGAGTTGGACACTGTACTCGGCCCCGGCGTACAGGTGACCGAACCAGACACGGCGAAGCTT  720
 H  P  E  I  Q  K  K  L  R  H  E  L  D  T  V  L  G  P  G  V  Q  V  T  E  P  D  T  A  K  L

CCGTACCTCCAAGCTGTCATCAAAGAGACCTTACGTCTCCGCATGGCAATCCCTCTTTTGGTGCCGCACATGAACCTTCACGATGCGAAA  810
 P  Y  L  Q  A  V  I  K  E  T  L  R  L  R  M  A  I  P  L  L  V  P  H  M  N  L  H  D  A  K

CTCGGAAGCTACGACATCCCTGCCGAGAGCAAGATTCTTGTCAACGCATGGTTCCTGGCTAACAATCCGGAGAAGTGGAAGAATCCGGAG  900
 L  G  S  Y  D  I  P  A  E  S  K  I  L  V  N  A  W  F  L  A  N  N  P  E  K  W  K  N  P  E

GAGTTCAGACCGGAGAGGTTCATGGAAGAAGAGTCCAAGGTCGAAGCTAGTGGGAACGACTTCAGGTACTTGCCTTTCGGCACTGGAAGG  990
 E  F  R  P  E  R  F  M  E  E  E  S  K  V  E  A  S  G  N  D  F  R  Y  L  P  F  G  T  G  R

AGGAGCTGTCCCGGCATAATCTTCGCCCTCCCAAGGGCGAATTCTGCAGATATCCATCACACTGGCGGCCGCTCGAGCATGCATCTAGAG 1080
 R  S  C  P  G  I  I  F  A  L  P  R  A  N  S  A  D  I  H  H  T  G  G  R  S  S  M  H  L  E

GGCCC 1085
 G  P
```

```
AAGCATCACCCGGGTCAGATGGAGGCCGTCCTCCCCAAAGAAGTCGAAACAGGACAGGTACGCTCTTCGGACGTCTCCCCAGTGGCTGGG   90
  S  I  T  R  V  R  W  R  P  S  S  P  K  K  S  K  Q  D  R  Y  A  L  R  T  S  P  Q  W  L  G

TCCGCAGGTGGAAGTTATTCGAGCATCGACCAAGTCGATAGAGCGAGAGATCAACTCCGTGAATGACAACCCACTCATCGATGTCTCCG   180
  P  Q  V  E  V  I  R  A  S  T  K  S  I  E  R  E  I  N  S  V  N  D  N  P  L  I  D  V  S  R

TAACAAGGCTCTCCACGGCGGAAACTTCCAAGGCACGCCCATCGGAGTATCCATGGACAACACCCGTCTGGCCATCGCTGCCATCGGGAA   270
  N  K  A  L  H  G  G  N  F  Q  G  T  P  I  G  V  S  M  D  N  T  R  L  A  I  A  A  I  G  K

ACTCATGTTCGCCCAGTTCTCCGAGTTGGTGAACGACTTCTACAACAACGGACTTCCGTCGAATCTATCCGGTGGCAGGAACCCAAGTCT   360
  L  M  F  A  Q  F  S  E  L  V  N  D  F  Y  N  N  G  L  P  S  N  L  S  G  G  R  N  P  S  L

TGATTACGGATTCAAAGGTGGAGAAATCGCCATGGCTTCCTATTGTTCCGAGCTTCAGTTCCTCGCAAACCCAGTAACCAACCACGTTCA   450
  D  Y  G  F  K  G  G  E  I  A  M  A  S  Y  C  S  E  L  Q  F  L  A  N  P  V  T  N  H  V  Q

ATCCGCCGAGCAACACAACCAAGATGTAAATTCTCTCGGTCTCATCTCCGCCAGAAAGACGGCGGAATCAATCGAGATTCTAAAGCTCAT   540
  S  A  E  Q  H  N  Q  D  V  N  S  L  G  L  I  S  A  R  K  T  A  E  S  I  E  I  L  K  L  M

GACATCTACATTCTTGGTTGGAATCTGCCAAGCCATCGATCTCAGACACATGGAAGAAAACCTTAAAGCTTCCGTGAAGAACACAGTGAG   630
  T  S  T  F  L  V  G  I  C  Q  A  I  D  L  R  H  M  E  E  N  L  K  A  S  V  K  N  T  V  S

TCAAGTGGCGAAACGCGTCCTCACCATGACCGCTAACGGTGAGCTCCACCCCTCCCGTTTCTGCGAGAAAGACCTTCTGAAAGTAGTTGA   720
  Q  V  A  K  R  V  L  T  M  T  A  N  G  E  L  H  P  S  R  F  C  E  K  D  L  L  K  V  V  D

CAGGGAGTACGTGTTTTCGTACATCGACGACCCATGCAGCGCCACTTACCCACTCATGCAGAAACTCCGATCCGTACTCGTCGACCATGC   810
  R  E  Y  V  F  S  Y  I  D  D  P  C  S  A  T  Y  P  L  M  Q  K  L  R  S  V  L  V  D  H  A

TCTGAACAACGGTGACAAAGAGAAAGACGAGGCAATGTCGATATTCCAGAAGATCGCCGTCTTCGAGGAGGAGTTGATTGCCGTCTTCCC   900
  L  N  N  G  D  K  E  K  D  E  A  M  S  I  F  Q  K  I  A  V  F  E  E  E  L  I  A  V  F  P

CAAGGAGGTCGA   912
  K  E  V  E
```

| | Disease | Fungus | Crops |
|---|---|---|---|
| Ascomycetes | Glume Blotch | Septoria nodorum | Cereals |
| | Leaf Spot | Septoria tritici | Cereals |
| | Powdery Mildew | Erysiphe spp. | Cereals Grapes |
| | Leaf Blotch | Rhynchosporium secalis | Cereals |
| | Stem Canker | Leptosphaeria maculans | Cereals |
| Basidiomycetes | Yellow Rust | Puccinia striiformis | Cereals |
| Oomycetes | Bluemold | Peronospora tabacina | Tobacco |
| | Eyespot | Psuedocerosporella herpotrich | Cereals |

Figure 21B

| Taxa | Disease | Fungus | Plant Infection | In vitro adhesion | Plant adhesion |
|---|---|---|---|---|---|
| Ascomycetes | Rice Blast | *Magnaporthe grisea* | ✓ | ✓ | ✓ |
| | Brassica Dark Leaf Spot | *Alternaria brassicicola* | ✓ | ✓ | ongoing |
| | Bean Anthracnose | *Colletotrichum lindemuthianum* | ✓ | ✓ | ✓ |
| | Strawberry Anthracnose | *C. fragarie* *C. acutatum* | ✓ | ✓ | ✓ |
| | Avocado Anthracnose | *C. gleosporioides* | ✓ | Not Tested | Not Tested |
| | Green Mold | *Penicillium italicum/digitatum* | ✓ | Not Tested | Not Tested |
| | Apple Scab | *Venturia inequalis* | ✓ | Not Tested | Not Tested |
| | Grey Mold | *Botrytis cinerea* | Not Tested | ✓ | Not Tested |
| | Leaf Spot | *Septoria tritici* | ✓ | Not Tested | Not Tested |

Figure 22

| | Disease | Fungus | Plant Infection | In vitro adhesion | In planta adhesion |
|---|---|---|---|---|---|
| Basidiomycetes | Wheat brown rust | *Puccinia recondita* | ✓ | ✓ | ✓ |
| | | | | | |
| Oomycetes Pythiaceae | Damping-off | *Pythium aphanidermatum* | ✓ | ongoing | ongoing |
| | Potato late blight | *Phytophthora infestans* | ✓ | ongoing | ongoing |
| Peronosporaceae | Downy Mildew | *Peronospora parasitica* | ongoing | ✓ | ongoing |

Figure 28
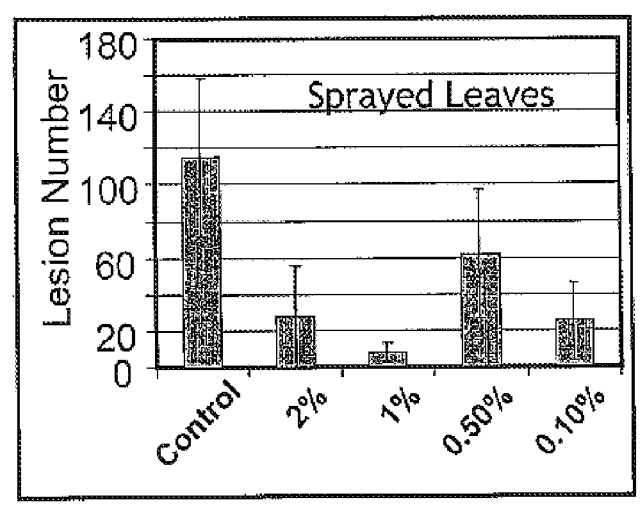
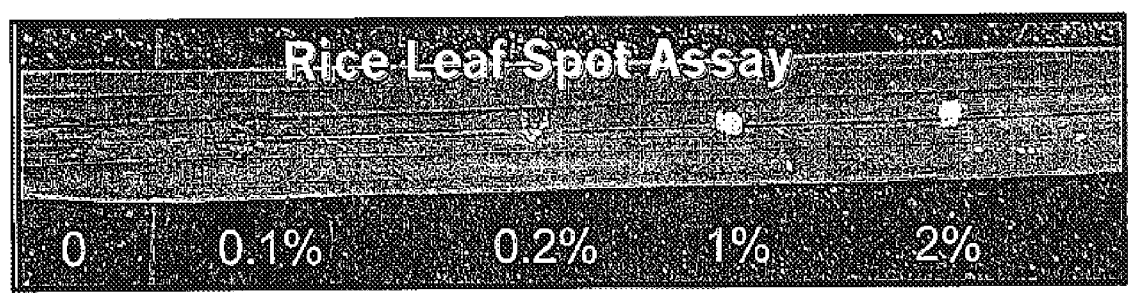

TRANSGENIC PLANTS INCORPORATING TRAITS OF *ZOSTERA MARINA*

CROSS-REFERENCE TO THE RELATED APPLICATION

This application claims the benefit of U.S. Provisional Application Ser. No. 60/202,529 filed May 10, 2000.

1. BACKGROUND OF THE INVENTION

Selective plant breeding has been used to genetically improve crop plants throughout human history. Early hunter-gatherers selectively propagated plants with preferred properties, while early agriculturists deliberately saved seeds from preferred plant types and thereby gradually domesticated a majority of the crop plants known today. Over the past 50 years the combined efforts of plant breeders to successfully develop new crop cultivars have provided the basis for the consistent supply of food in a changing global environment and ever-changing pest and disease populations. This has been a major contributing factor toward the alleviation of world hunger and suffering, and, in some instances, the consequent maintenance of political stability.

The development of plant molecular genetics has facilitated plant breeding methods through such techniques as marker-assisted selection, in which genetic maps of polymorphic markers are used to monitor the selection of plant lines containing desirable alleles of closely-linked genes. Nevertheless, such breeding techniques are ultimately limited by the diversity of the existing genetic material in crop plants. This limitation to the development of crop plants with desirable new genetic traits is substantial in view of the limitations inherent in the genetic diversity of any individual plant species adapted to a select environment in general and the history of inbreeding of crop plants in particular.

Recently developed method of plant genetic engineering offer a means to overcome this limitation by the introduction of new genes into single plant cells from which complete plants can be regenerated via cell and tissue culture methodologies. Genetic engineering of plants has been utilized to improve the quality of crop plant products, such as in the development of an improved tomato with superior ripening characteristics by the expression of an antisense polygalacturonase gene (see Kramer et al. (1994) Euphytica 79: 293–7). Indeed, entire biosynthetic pathways have been altered by plant genetic engineering techniques. For example, starch biosynthesis has been successfully manipulated in tomato (for paste production) and potato (for processing quality and reduced oil uptake) be expression of a bacterial ADP glucose pyrophosphorylase that is insensitive to feedback regulation (see Stark et al. (1996) Ann NY Acad Sci 792: 26–36). There is also great economic potential in the use of transgenic plants engineered for the production of biopharmaceutical compounds. Among the products that are likely to be produced in transgenic plants are cytokines, hormones, monoclonal antibodies, enzymes, and vaccines. Some of these products may be expressed either from stably transformed plants, or from transient expression systems in the form of recombinant plant viral vectors.

The ability to genetically manipulate plants may further allow crops to be grown under conditions of environmental stress or in the presence of plant pathogens. Plants are susceptible to infection by many parasitic, viral, fungal and bacterial organisms, which infect following contact with root, stem, leaf or other plant tissues. Other environmental insults, such as flooding, can damage plants by causing root anoxia. Indeed many agriculturally important crops are destroyed as a result of both infection by pathogens and root damage caused by flooding. For example, corn is highly susceptible to flooding and water logged soil can account for 20–30% losses in the production of this crop in clay-rich soils. The water logging of plant roots causes root anoxia, resulting in a build-up of ethanol and resultant loss of plant viability.

Another environmental stress which seriously affects the productivity of crop plants is salt-stress. Although plant species differ in their relative sensitivity to salt, crop plants are predominantly sensitive to the presence of high concentrations of salts in the soil. Salinity affects more than 40 percent of the world's irrigated lands, including the most productive agricultural areas of the Mediterranean basin, California and southern Asia, where use of poor quality irrigation water has led to the progressive concentration of salts in the soil (Flowers and Yeo (1995) Aust J Plant Physiol 22: 875–884). Approximately 10 million hectares of irrigated land are thought to be rendered useless for crop plant production each year because of the adverse effects of secondary salinization (Szaboles (1987)Acta Agronomica Hungarica 36: 159–72). One strategy for dealing with this problem may be the development of salt-resistant crops, however salt-tolerance does not appear to depend on a single identifiable trait, and traditional plant breeding and the transfer of single traits has been shown to improve salt-tolerance only marginally (Delauney and Verma (1993) Plant J 4: 215–23).

Yet another environmental stress which affects the worldwide productivity of crop plants is exposure to fungal, bacterial and viral pathogens. Certain marine plants may avoid infection by such pathogens, despite continuous exposure to these agents in their aqueous marine environment, by virtue of their production of "anti-fouling" compounds. Fouling is a general term describing the interaction and attachment of various organisms, including marine bacteria and barnacles, to a plant or other surface. The marine seagrass *Zostera marina* has desirable antifouling characteristics which make it resistant to the attachment of such pathogens and parasites. *Zostera marina* produces a variety of phenolic acids, including p-(sulfooxy)-cinnamic acid, as natural products. It has been proposed that such phenolic acids confer resistance to so-called wasting disease and inhibit ampthipod grazing, microbial growth and the attachment of marine bacteria, diatoms, barnacles and polychaetes to artificial surfaces. The sulfated phenolic acids have been shown to possess particularly effective antifouling characteristics in laboratory studies (Todd et al. (1993) Phytochemistry 34: 401–4). Significantly, the attachment of pathogenic bacteria, fungi and viruses is the first step toward infection and so these antifouling characteristics are particularly desirable because they preclude infection.

2. SUMMARY OF THE INVENTION

The invention features compositions and methods for the genetic engineering of plant species to incorporate certain traits of the marine vascular plant, *Zostera marina*. This species of marine eelgrass appears to have evolved from a terrestrial vascular plant family which, in the process of adapting to the marine environment, acquired several desirable genetic traits such as salt and anoxia resistance as well as a particular pathogen defense strategy. The invention involves the incorporation of one or more of the genes responsible for these distinguishing traits into other plant species, such as crop plants.

3. BRIEF DESCRIPTION OF THE FIGURES

FIG. 3 depicts the degenerate (SEQ ID NO: 5–7) and gene-specific primers used in cloning *Zostera marina* sulfotransferase. Amino acid sequences corresponding to the degenerate sequences are indicates by SEQ ID NO: 12–14.

FIG. 4 depicts the nucleotide and amino acid sequence of a sulfotransferase cloned from *Zostera marina* (SEQ ID NO: 15 and 16).

FIG. 5 depicts an alignment of the deduced *Zostera marina* sulfotransferase amino acid sequence (SEQ ID NO: 17) with sulfotransferases from *Arabidopsis thaliana* (P52839) (SEQ ID NO: 19), *Brassica napus* (T07832) (SEQ ID NO: 18), *Flaveria bidentis* (P52832) (SEQ ID NO: 20) and *Homo sapiens* (NM003166) (SEQ ID NO: 21). The arrowed lines indicate the location of the conserved blocks and the dots indicate the motif involved in dimerization of the enzymes. The sequences were aligned using MegAlign program from DNAStar Inc.

FIG. 6 depicts the sequence of the intron from *Zostera marina* sulfotransferase (SEQ ID NO: 22). Sequences inside the boxes are consensus motifs of the 5' and 3' intron splice sites for plant genes. Stop codons are indicated by the dots.

FIG. 7 depicts a method of identifying the function of the *Zostera marina* ST gene product through subcloning, expression and enzymic activity analysis.

Figure 8:
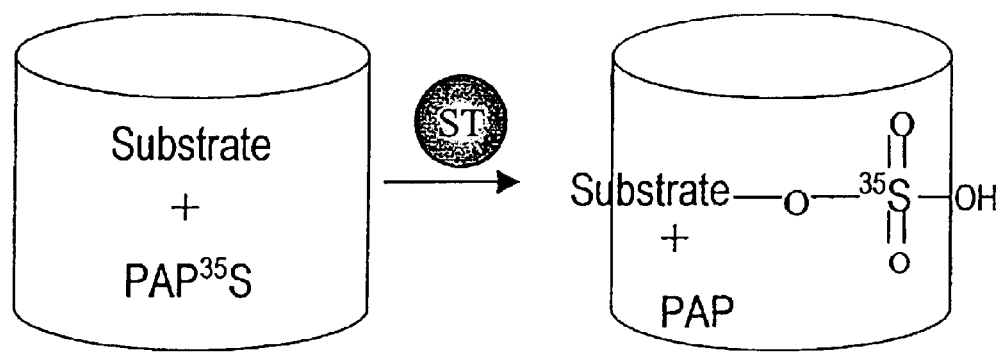

FIG. 8 depicts an ST-catalyzed sulfur transferation reaction assay.

Figure 9:
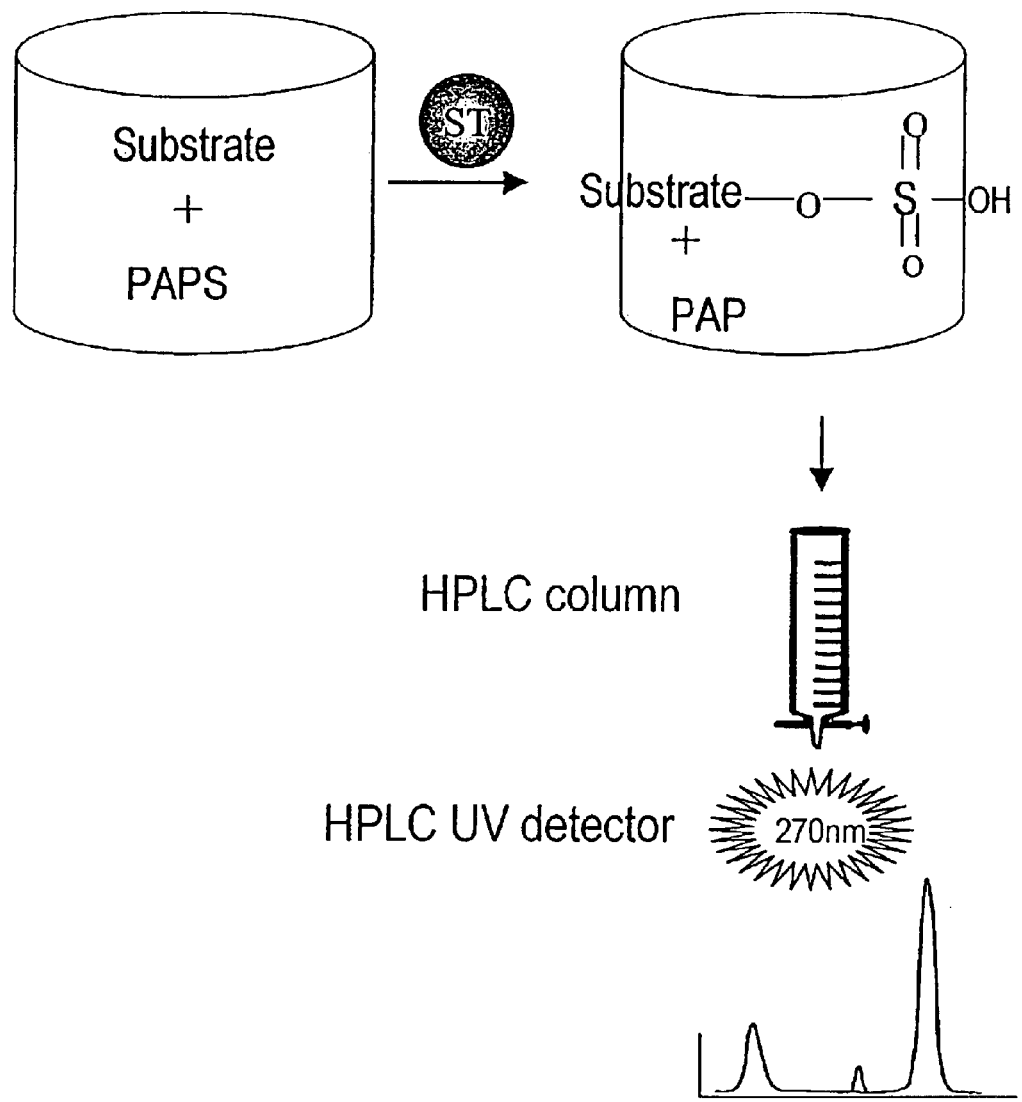

FIG. 9 depicts purification of the ST by the ST-catalyzed sulfur transferation reaction assay.

FIG. 10 summarizes a comparison of *Zostera marina*, *Flaveria* and Rat Dopa/tyrosine ST activities.

FIG. 11 depicts the sequences of degenerate primers to conserved protein sequences of ADH (SEQ ID NO: 23 and 29), CH (SEQ ID NO: 24 and 30) and PAL (SEQ ID NO: 25 and 31) used in cloning *Zostera marina* Alcohol Dehydrogenase, Cinnamate 4-Hydroxylase and Phenylalanine Ammonia Lyase genes from *Zostera marina*.

FIG. 12 summarizes the approximate sizes of the ADH, CH, PAL and POX targeted genes and the size of the of partial clone obtained.

FIG. 13 depicts the nucleotide and amino acid sequence of a partial alcohol dehydrogenase cDNA clone from *Zostera marina* (SEQ ID NO:35 and SEQ ID NO: 36).

FIG. 14 depicts an alignment of the deduced *Zostera marina* ADH amino acid sequence (SEQ ID NO: 37) with *Arabidopsis thaliana* ADH (BAA19623) (SEQ ID NO: 38), corn (S04571) (SEQ ID NO: 39), and *E. coli* (AAC73459) (SEQ ID NO: 40).

FIG. 15 depicts the nucleotide and amino acid sequence of a partial cinnamate 4-hydroxylase cDNA clone from *Zostera marina* (SEQ ID NO: 41 and (SEQ ID NO: 42).

Figure 16:
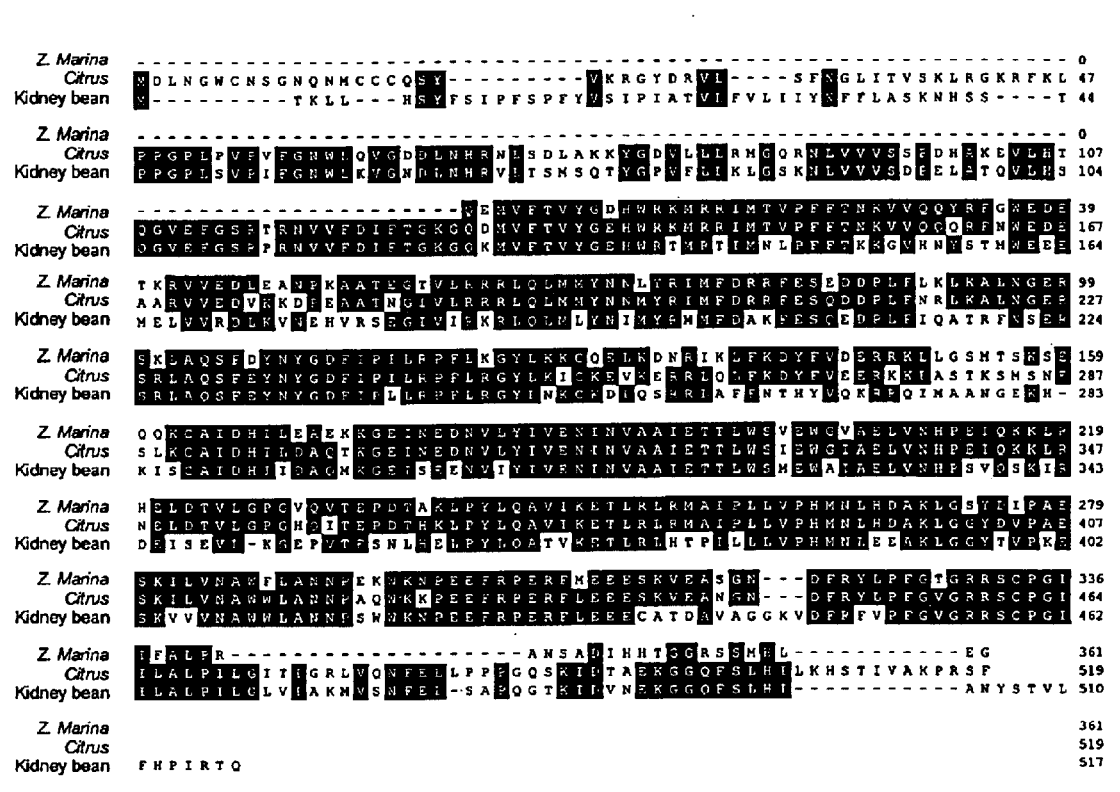

FIG. 16 depicts an alignment of the deduced *Zostera marina* CH amino acid sequence (SEQ ID NO: 43) with *Citrus senensis* CH (AAF66066) (SEQ ID NO: 44) and *Phaseolus vulgaris* (Kidney Bean) CH (T10857) (SEQ ID NO: 45).

FIG. 17 depicts the nucleotide and amino acid sequence of a partial Phenylalanine ammonia lyase cDNA clone from *Zostera marina* (SEQ ID NO: 46 and SEQ ID NO: 47).

Figure 18:
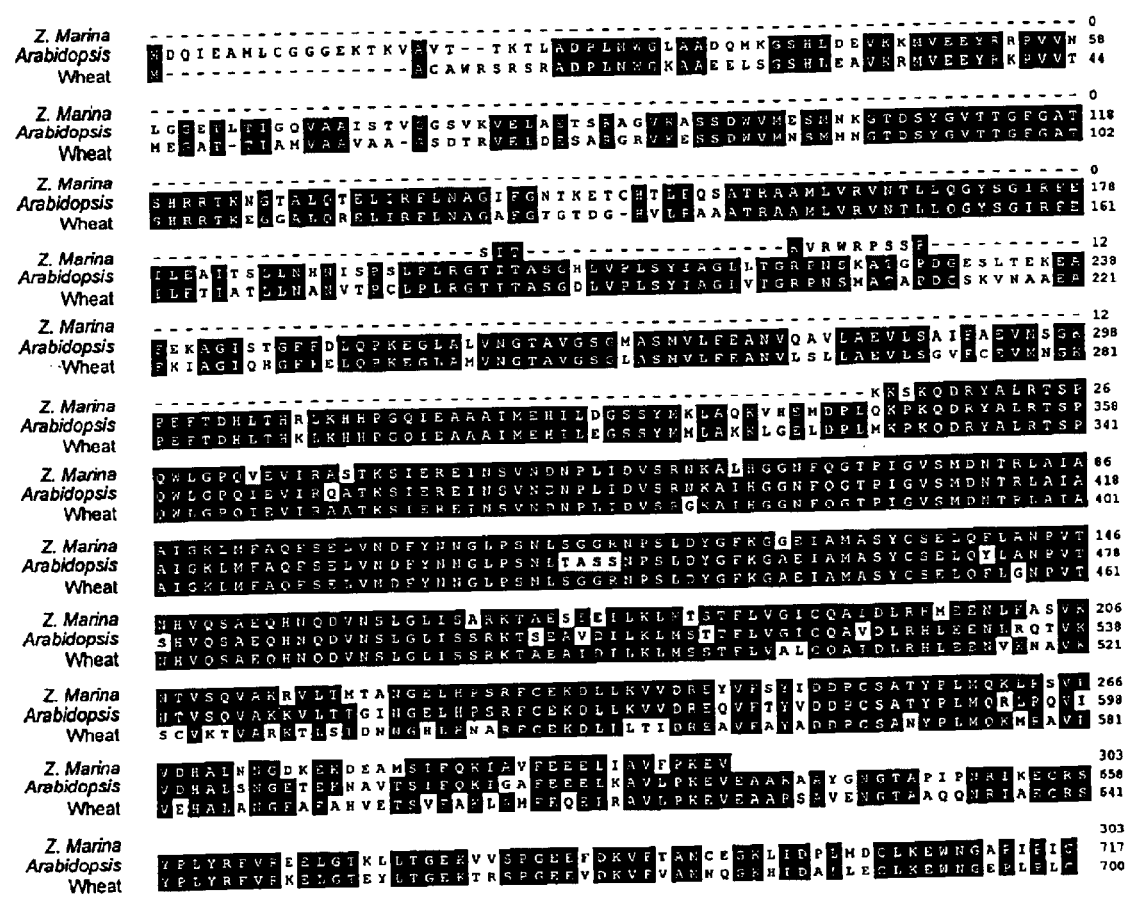

FIG. 18 depicts an alignment of the deduced *Zostera marina* PAL amino acid sequence (SEQ ID NO: 48) with *Arabidopsis thaliana* PAL (S52991) (SEQ ID NO: 49) and *Triticum aestivum* (wheat) PAL (CAA68036) (SEQ ID NO: 50).

Figure 19:
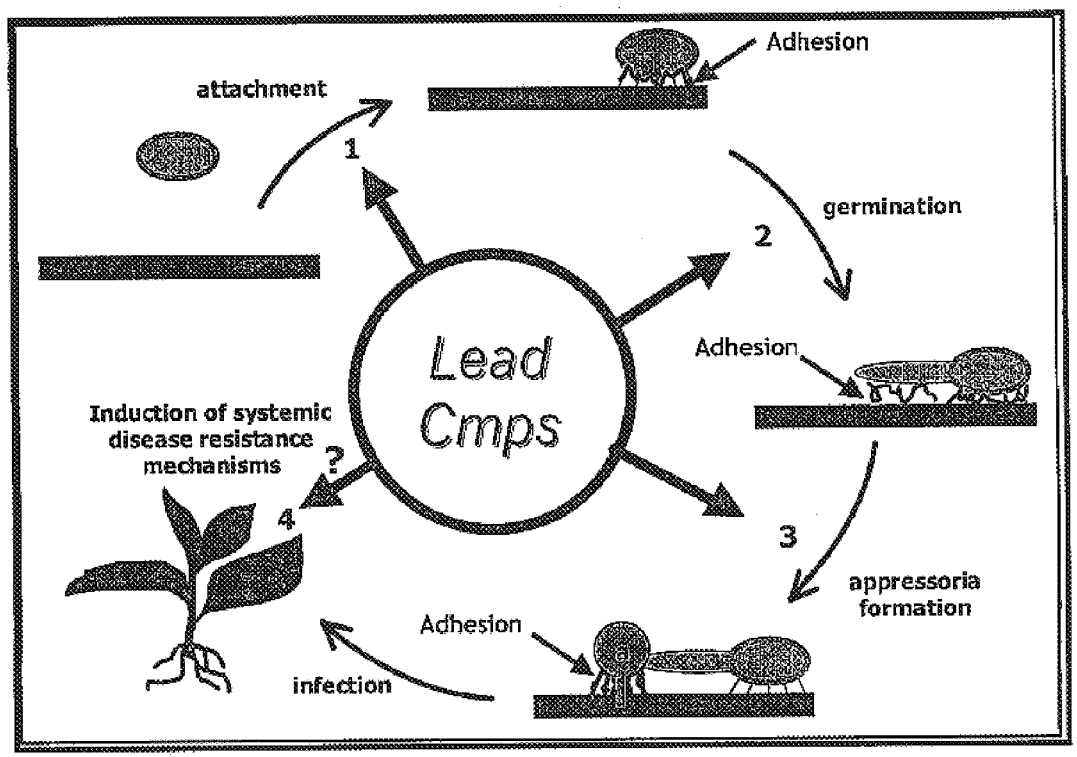

FIG. 19 depicts several steps in fungal infection which may be targeted by one or more of the transgenic strategies of the invention.

Figure 20:
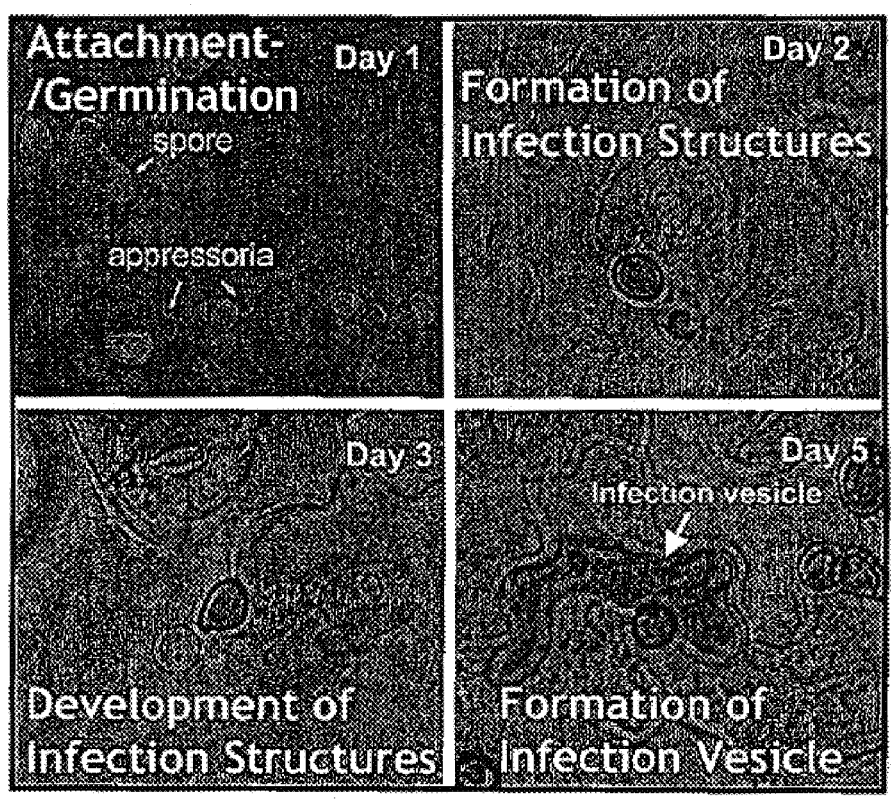

FIG. 20 shows micrographs depicting the infection process for Colletotrichum.

FIG. 21 (A, B) summarizes a number of known plant pathogenic fungi, the popular names of the diseases they cause, and the crop plant types that they infect.

FIG. 22 summarizes some of the results obtained to date using various fungal pathogens.

Figure 23:
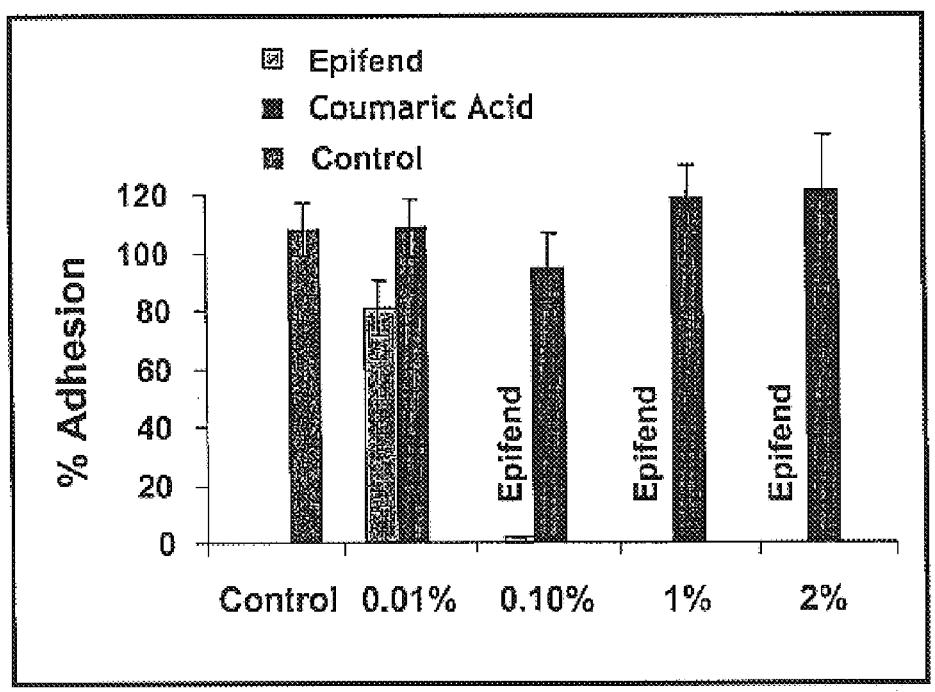

FIG. 23 shows that Epifend inhibits adhesion of Colletotrichum spores to polystyrene, while coumaric acid did not inhibit spore adhesion.

Figure 24:
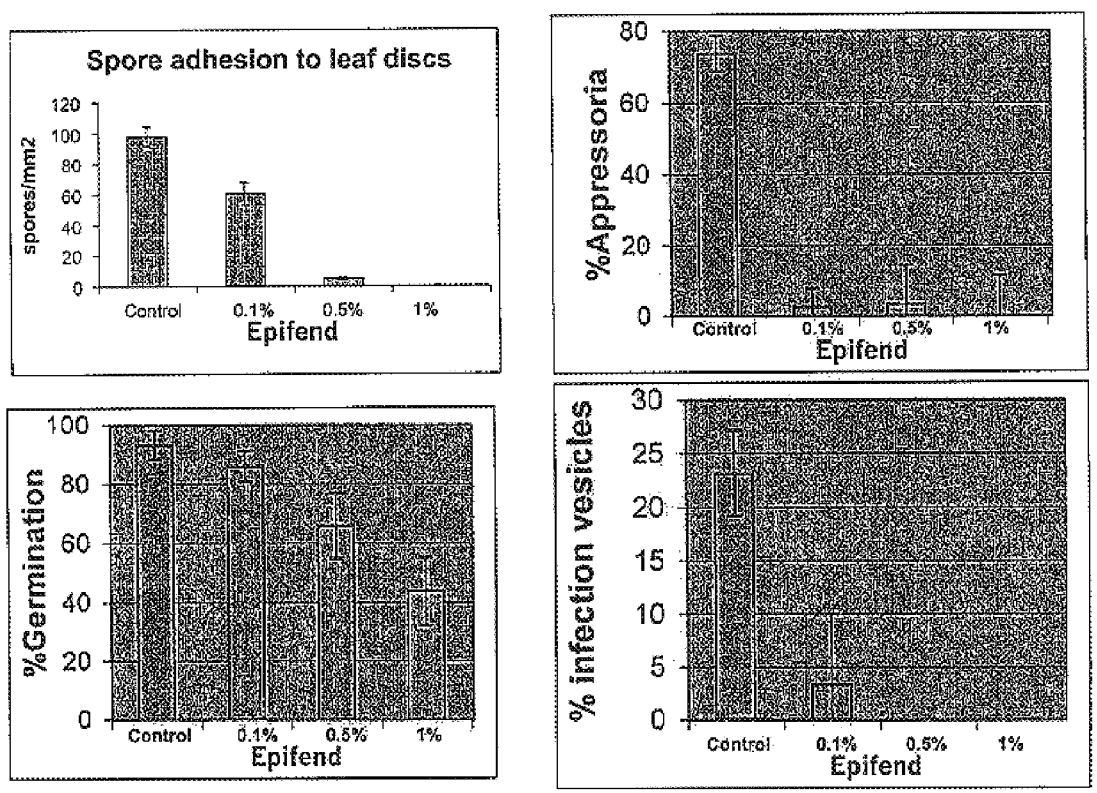

FIG. 24 shows that Epifend inhibits spore adhesion to glass, polystyrene and leaf surfaces, at concentrations as low as 0.01%.

Figure 25:
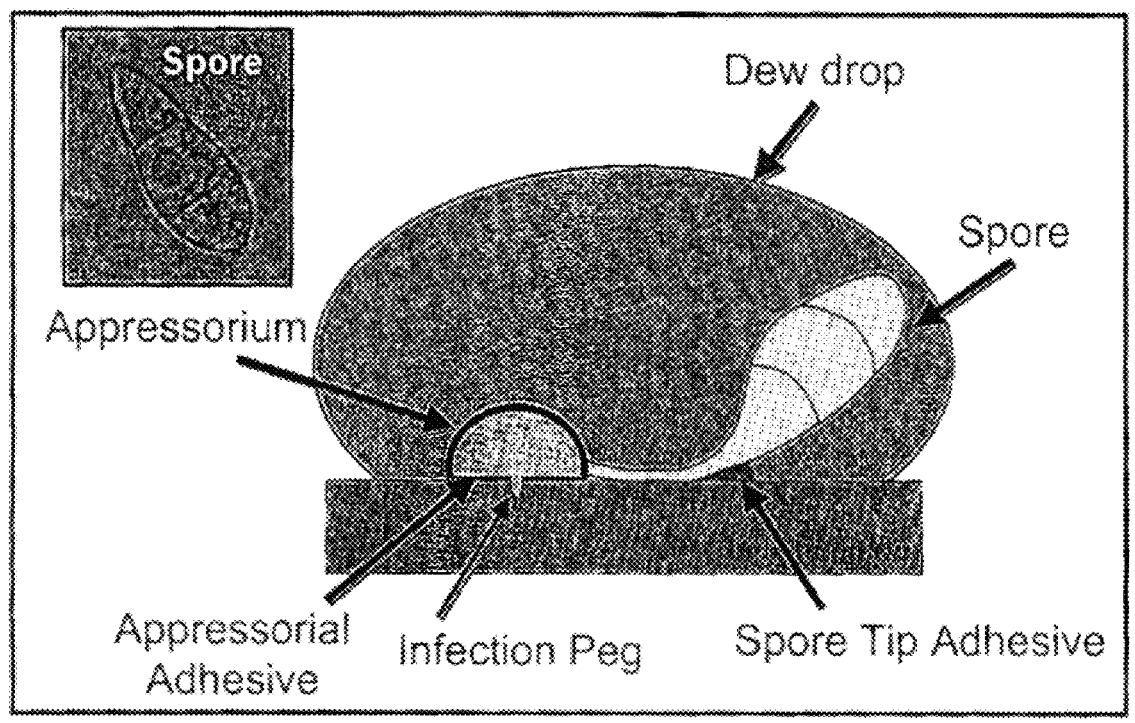

FIG. 25 depicts the infection of rice blast by *Magnaporthe grisea*.

Figure 26:
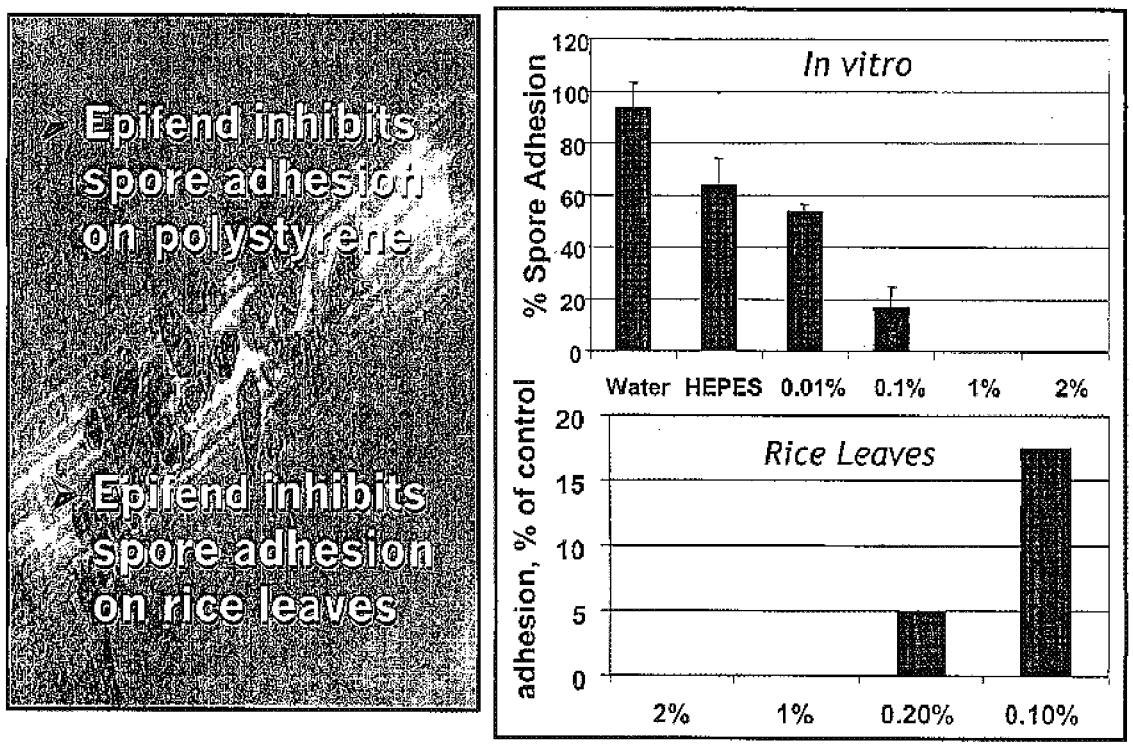

FIG. 26 shows that Epifend inhibits spore adhesion to polystyrene and rice leaf surfaces, at concentrations as low as 0.01%.

Figure 27:
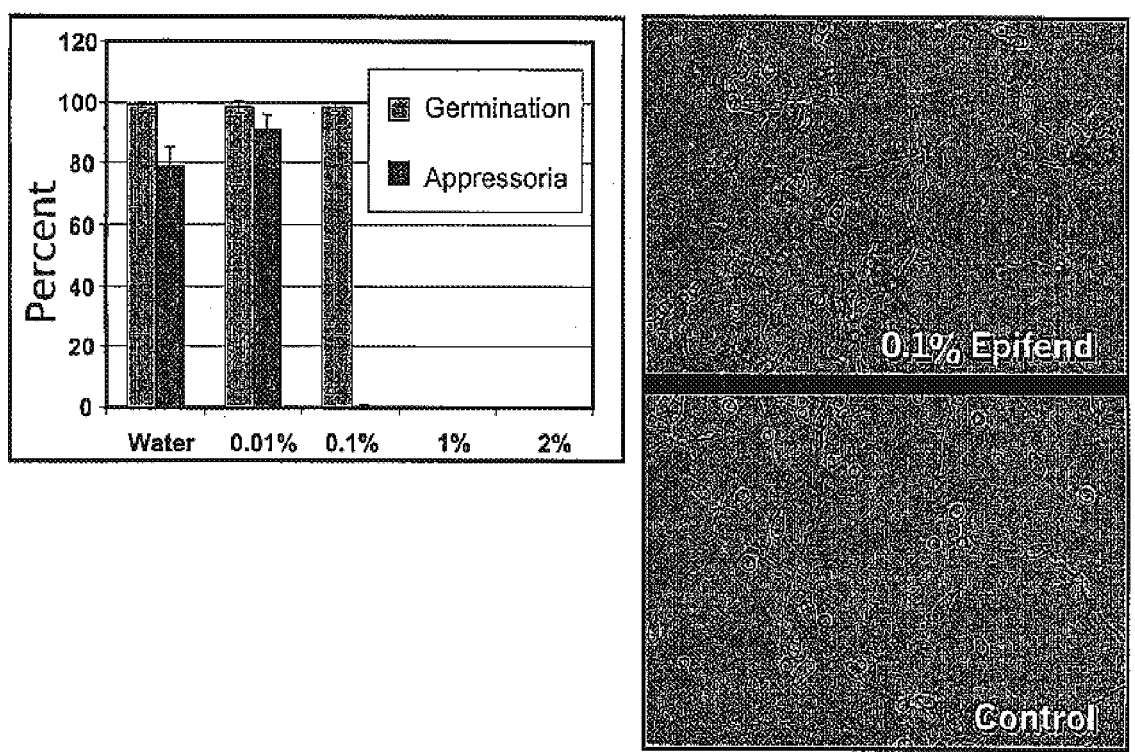

FIG. 27 shows that Epifend-treated rice leaf had ungerminated spores.

FIG. 28 depicts a rice leaf spot assay in which Epifend (at 0.2%) fully prevents lesion formation.

Figure 29:
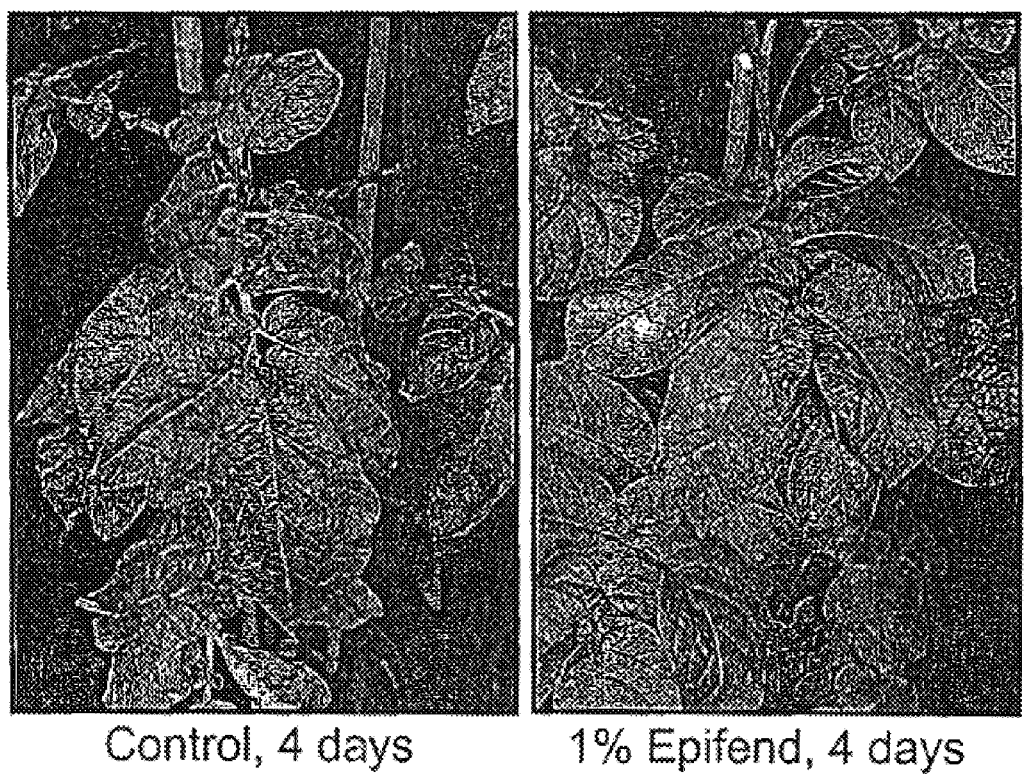

FIG. 29 shows the effect of 1% Epifend in reducing infection in Bintje (at 4 days).

Figure 30:
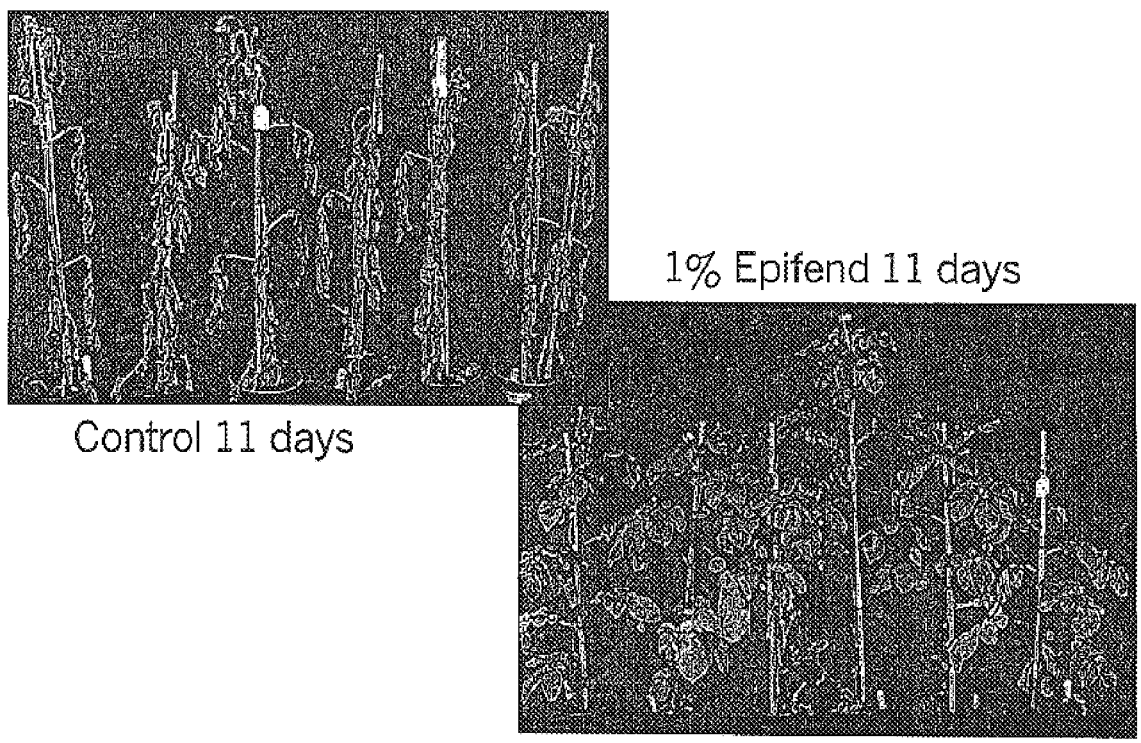

FIG. 30 shows the effect of 1% Epifend in reducing infection in Bintje (at 11 days).

4. DETAILED DESCRIPTION OF THE INVENTION

4.1. General

In general, the invention provides transgenic plants incorporating heterologous genes that confer or contribute to one or more traits of a family of marine vascular plant which includes *Zostera marina*.

4.2. Definitions

For convenience, the meaning of certain terms and phrases employed in the specification, examples, and appended claims are provided below.

The term "abzyme" refers to an immunoglobulin molecule capable of acting as an enzyme or a catalyst.

The term "agonist", as used herein, is meant to refer to an agent that mimics or upregulates (e.g. potentiates or supplements) a bioactivity. For example, a sulfotransferase agonist can be a wild-type sulfotransferase protein or derivative thereof having at least one bioactivity of the wild-type sulfotransferase receptor binding activity. An agonist can also be a compound which increases the interaction of a bioactive polypeptide with another molecule, for example, a receptor. Agonists can be any class of molecule, preferably a small molecule, including a nucleic acid, protein, carbohydrate, lipid or combination thereof.

The term "allele", which is used interchangeably herein with "allelic variant" refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene or allele. Alleles of a specific gene can differ from each other in a single nucleotide, or several nucleotides, and can include substitutions, deletions, and insertions of nucleotides. Frequently occurring sequence variations include transition mutations (i.e. purine to purine substitutions and pyrimidine to pyrimidine substitutions, e.g. A to G or C to T), transversion mutations (i.e. purine to pyrimidine and pyrimidine to purine substitutions, e.g. A to T or C to G), and alteration in repetitive DNA sequences (e.g. expansions and contractions of trinucleotide repeat and other tandem repeat sequences). An allele of a gene can also be a form of a gene containing a mutation. The term "allelic variant of a polymorphic region of a gene" refers to a region of a locus gene having one or several nucleotide sequence differences found in that region of the gene in other individuals.

As used herein, the term "anti-fouling" or "anti-fouling activity" is a general term which encompasses any biological activity that decreases or prevents the interaction, attachment and/or development of any of various organisms, particularly plant pathogenic organisms such as bacteria, yeast, algal and fungal spores and invertebrate larvae, which may attach to a plant or other surface. As used herein, an "anti-fouling" activities may include those which antagonize any step in the infection process such as attachment, adhesion, germination, appressoria formation or infection structure formation or infection vehicle development.

The term "antagonist" as used herein is meant to refer to an agent that downregulates (e.g. suppresses or inhibit;) at least bioactivity. An antagonist can be a compound which inhibits or decreases the interaction between one protein and another molecule, e.g., a substrate. Accordingly, a preferred antagonist is a compound which inhibits or decreases binding to a substrate and thereby blocks enzyme function. An antagonist can also be a compound that downregulates expression of a gene or genes or which reduces the amount of a gene product translated. The target bioactivity antagonist can be a dominant negative form of a polypeptide possessing that bioactivity, for example Kreb's citric acid cycle antagonists would include a form of a pyruvate dehydrogenase subunit polypeptide which is capable of interacting with another subunit of the pyruvate dehydrogenase complex, but which interferes with catalysis of the resulting complex (i.e. a dominant negative form of the target bioactivity). An antangonist can also be an antisense nucleic acid, or a ribozyme capable of interacting specifically with a traget bioactivity-encoding mRNA. Yet other antagonists are molecules which bind to a traget bioactivity and inhibit its action. Such molecules include peptides such as those which will bind the active site of an enzyme and prevent it from interacting with substrate. Yet other target bioactivity antagonists include antibodies which interact specifically with an epitope of the target polypeptide, such that binding interferes with the biological function of the polypeptide. In yet another preferred embodiment, the antagonist is a small molecule, such as a molecule capable of inhibiting the interaction between a target enzyme and its substrate.

"Asexual propagation" refers to producing progeny by regenerating an entire plant from leaf cuttings, stem cuttings, root cuttings, single plant cells (protoplasts) and callus.

The term "catalytic site" refers to the portion of a molecule that is capable of binding a reactant and improving the rate of a reaction. Catalytic sites may be present on polypeptides or proteins, enzymes, organics, organo-metal compounds, metals and the like. A catalytic site may be made up of separate portions present on one or more polypeptide chains or compounds. These separate catalytic portions associate together to form a larger portion of a catalytic site. A catalytic site may be formed by a polypeptide or protein that is bonded to a metal.

"Cells", "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric polypeptide" or "fusion polypeptide" is a fusion of a first amino acid sequence encoding one of the subject polypeptides with a second amino acid sequence defining a domain (e.g. polypeptide portion) foreign to and not substantially homologous with any domain of the subject polypeptide. A chimeric polypeptide may present a foreign domain which is found (albeit in a different polypeptide) in an organism which also expresses the first polypeptide, or it may be an "interspecies", "intergenic", etc. fusion of polypeptide structures expressed by different kinds of organisms. In general, a fusion polypeptide can be represented by the general formula X-polypeptide-Y, wherein polypetide represents a first or subject protein or polypeptide, and X and Y are independently absent or represent amino acid sequences which are not related to the first sequence in an organism, including naturally occurring mutants.

As used herein, "conservatively modified variations" of a particular nucleic acid sequence refer to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For instance, the codons CGU, CGC, CGA, COG, AGA, and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations." Every nucleic acid sequence herein which encodes a polypeptide also describes every possible silent variation. One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in each described sequence. Furthermore, one of skill will recognize that individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

As described herein, sequences are preferably optimized for expression in a particular host cell used to produce the protein (e.g., a plant cell such as a tomato, or a cloning and expression system such as a yeast cell). Similarly, "conservative amino acid substitutions," in one or a few amino acids in an amino acid sequence are substituted with different amino acids with highly similar properties (see, the definitions section, supra), are also readily identified as being highly similar to a particular amino acid sequence, or to a particular nucleic acid sequence which encodes an amino acid. Such conservatively substituted variations of any particular sequence are a feature of the present invention.

A "delivery complex" shall mean a targeting means (e.g. a molecule that results in higher affinity binding of a gene, protein, polypeptide or peptide to a target cell surface and/or increased cellular or nuclear uptake by a target cell). Examples of targeting means include: sterols (e.g. cholesterol), lipids (e.g. a cationic lipid, virosome or liposome), viruses (e.g. tobacco mosaic virus) or target cell specific binding agents (e.g. ligands recognized by target cell specific receptors). Preferred complexes are sufficiently stable in vivo to prevent significant uncoupling prior to internalization by the target cell. However, the complex is cleavable under appropriate conditions within the cell so that the gene, protein, polypeptide or peptide is released in a functional form.

As is well known, genes may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding a target polypeptide" may thus refer to one or more genes within a particular individual. Moreover, certain differences in nucleotide sequences may exist between individual organisms, which are called alleles. Such allelic differences may or may not result in differences in amino acid sequence of the encoded polypeptide yet still encode a polypeptide with the same biological activity.

The phrases "disruption of the gene" and "targeted disruption" or any similar phrase refers to the site specific interruption of a native DNA sequence so as to prevent expression of that gene in the cell as compared to the wild-type copy of the gene. The interruption may be caused by deletions, insertions or modifications to the gene, or any combination thereof.

The term "enzymatic site" refers to the portion of a protein molecule that contains a catalytic site. Most enzymatic sites exhibit a very high selective substrate specificity. An enzymatic site may be comprised of two or more enzymatic site portions present on different segments of the same polypeptide chain. These enzymatic site portions are associated together to form a greater portion of an enzymatic site. A portion of an enzymatic site may also be a metal.

The term "enzyme" refers to a protein, polypeptide, peptide RNA molecule, or multimeric protein capable of accelerating or producing by catalytic action some change in a substrate for which it is often specific.

The term "epitope" refers to portion of a molecule that is specifically recognized by an immunoglobulin product. It is also referred to as the determinant or antigenic determinant.

As used herein, an "immunoglobulin" is a multimeric protein containing the immunologically active portions of an immunoglobulin heavy chain and immunoglobulin light chain covalently coupled together and capable of specifically combining with antigen.

As used herein, a Fab fragment is a multimeric protein consisting of the portion of an immunoglobulin molecule containing the immunologically active portions of an immunoglobulin heavy chain and an immunoglobulin light chain covalently coupled together and capable of specifically combining with antigen. Fab fragments are typically prepared by proteolytic digestion of substantially intact immunoglobulin molecules with papain using methods that are well known in the art. However, a Fab fragment may also be prepared by expressing in a suitable host cell the desired portions of immunoglobulin heavy chain and immunoglobulin light chain using methods well known in the art.

As used herein, an F[v]fragment: A multimeric protein consisting of the immunologically active portions of an immunoglobulin heavy chain variable region and an immunoglobulin light chain variable region covalently coupled together and capable of specifically combining with antigen. F[v]fragments are typically prepared by expressing in suitable host cell the desired portions of immunoglobulin heavy chain variable region and immunoglobulin light chain variable region using methods well known in the art.

As used herein, the term "gene" or "recombinant gene" refers to a nucleic acid comprising an open reading frame encoding a polypeptide of the present invention, including both exon and (optionally) intron sequences. A "recombinant gene" refers to nucleic acid encoding such regulatory polypeptides, which may optionally include intron sequences which are either derived from a chromosomal DNA. Exemplary recombinant genes include those which encode a sulfotransferase activity.

As used herein, "heterologous DNA" or "heterologous nucleic acid" include DNA that does not occur naturally as part of the genome in which it is present or which is found in a location or locations in the genome that differs from that in which it occurs in nature. Heterologous DNA is not endogenous to the cell into which it is introduced, but has been obtained from another cell. Generally, although not necessarily, such DNA encodes RNA and proteins that are not normally produced by the cell in which it is expressed. Heterologous DNA may also be referred to as foreign DNA, Any DNA that one of skill in the art would recognize or consider as heterologous or foreign to the cell in which is expressed is herein encompassed by heterologous DNA. Examples of heterologous DNA include, but are not limited to, isolated DNA that encodes a sulfotransferase protein.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are identical at that position. A degree of homology or similarity or identity between nucleic acid sequences is a function of the number of identical or matching nucleotides at positions shared by the nucleic acid sequences. A degree of identity of amino acid sequences is a function of the number of identical amino acids at positions shared by the amino acid sequences. A degree of homology or similarity of amino acid sequences is a function of the number of amino acids, i.e. structurally related, at positions shared by the amino acid sequences. An "unrelated" or "non-homologous" sequence shares less than 40% identity, though preferably less than 25% identity, with one of the sequences of the present invention.

"Inactivation", with respect to genes of the host cell, means that production of a functional gene product is prevented or inhibited. Inactivation may be achieved by deletion of the gene, mutation of the promoter so that expression does not occur, or mutation of the coding sequence so that the gene product is inactive (constitutively or inducibly). Inactivation may be partial or total.

The term "interact" as used herein is meant to include detectable relationships or association (e.g. biochemical interactions) between molecules, such as interaction between protein-protein, protein-nucleic acid, nucleic acid-nucleic acid, and protein-small molecule or nucleic acid-small molecule in nature.

The term "isolated" as also used herein with respect to nucleic acids, such as DNA or RNA, refers to molecules separated from other DNAs, or RNAs, respectively, that are present in the natural source of the macromolecule. For example, isolated nucleic acids encoding the subject polypeptides preferably include no more than 10 kilobases (kb) of nucleic acid sequence which naturally immediately flanks that gene in genomic DNA, more preferably no more than 5 kb of such naturally occurring flanking sequences, and most preferably less than 1.5 kb of such naturally occurring flanking sequence. The term isolated as used herein also refers to a nucleic acid or polypeptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

The term "knock-out" refers to partial or complete suppression of the expression of an endogenous gene. This is generally accomplished by deleting a portion of the gene or by replacing a portion with a second sequence, but may also be caused by other modifications to the gene such as the introduction of stop codons, the mutation of critical amino acids, the removal of an intron junction, etc.

The term "marker" or "marker sequence" or similar phrase means any gene that produces a selectable genotype or preferably a selectable phenotype. It includes such examples as the neo gene, green fluorescent protein (GFP) gene, TK gene, b-galactosidase gene, etc. The marker sequence may be any sequence known to those skilled in the art that serves these purposes, although typically the marker sequence will be a sequence encoding a protein that confers a selectable trait, such as an antibiotic resistance gene, or an enzyme that can be detected and that is not typically found in the cell. The marker sequence may also include regulatory regions such as a promoter or enhancer that regulates the expression of that protein. However, it is also possible to transcribe the marker using endogenous regulatory sequences. In one embodiment of the present invention, the marker facilitates separation of transfected from untransfected cells by fluorescence activated cell sorting, for example by the use of a fluorescently labeled antibody or the expression of a fluorescent protein such as GFP. Other DNA sequences that facilitate expression of marker genes may also be incorporated into the DNA constructs of the present invention. These sequences include, but are not limited to transcription initiation and termination signals, translation signals, post-translational modification signals, intron splicing junctions, ribosome binding sites, and polyadenylation signals, to name a few. The marker sequence may also be used to append sequence to the target gene. For example, it may be used to add a stop codon to truncate IL-1RN translation. The use of selectable markers is well known in the art and need not be detailed herein. The term "modulation" as used herein refers to both upregulation (i.e., activation or stimulation (e.g., by agonizing or potentiating)) and downregulation (i.e. inhibition or suppression (e.g., by antagonizing, decreasing or inhibiting)).

A "mutated gene" or "mutation" refers to an allelic form of a gene, which is capable of altering the phenotype of a subject having the mutated gene relative to a subject which does not have the mutated gene. If a subject must be homozygous for this mutation to have an altered phenotype, the mutation is said to be recessive. If one copy of the mutated gene is sufficient to alter the genotype of the subject, the mutation is said to be dominant. If a subject has one copy of the mutated gene and has a phenotype that is intermediate between that of a homozygous and that of a heterozygous subject (for that gene), the mutation is said to be co-dominant.

As used herein, the term "nucleic acid" refers to polynucleotides such as deoxyribonucleic acid (DNA), and, where appropriate, ribonucleic acid (RNA). The term should be understood to include either single- or double-stranded forms of nucleic acid, and, as equivalents, analogs of either RNA or DNA. Such nucleic acid analogs may be composed of nucleotide analogs, and, as applicable to the embodiment being described, may be single-stranded (such as sense or antisense) or double-stranded polynucleotides.

The phrase "nucleotide sequence complementary to the nucleotide sequence set forth in SEQ ID NO. x" refers to the nucleotide sequence of the complementary strand of a nucleic acid strand having SEQ ID NO. x. The term "complementary strand" is used herein interchangeably with the term "complement". The complement of a nucleic acid strand can be the complement of a coding strand or the complement of a non-coding strand. When referring to double stranded nucleic acids, the complement of a nucleic acid having SEQ ID NO. x refers to the complementary strand of the strand having SEQ ID NO. x or to any nucleic acid having the nucleotide sequence of the complementary strand of SEQ ID NO. x. When referring to a single stranded nucleic acid having the nucleotide sequence SEQ ID NO. x, the complement of this nucleic acid is a nucleic acid having a nucleotide sequence which is complementary to that of SEQ ID NO. x. The nucleotide sequences and complementary sequences thereof are always given in the 5' to 3' direction.

The phrase "operably linked" refers to functional linkage between a promoter and a second sequence, wherein the promoter sequence initiates transcription of RNA corresponding to the second sequence.

The term "percent identical" refers to sequence identity between two amino acid sequences or between two nucleotide sequences. Identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology/similarity or identity refers to a function of the number of identical or similar amino acids at positions shared by the compared sequences. Various alignment algorithms and/or programs may be used, including FASTA, BLAST or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a, gap weight of 1, e.g., each amino acid gap is weighted as if it were a single amino acid or nucleotide mismatch between the two sequences.

The term "phenolic sulfotransferase," as used herein is meant to include any of a number of naturally-occurring animal or plant enzymes which catalyze the sulfation of phenolic acids or other aromatic alcohols such as flavonols. As used herein, the term "phenolic sulfotransferase" further includes synthetic or genetically engineered polypeptides possessing the ability to catalyze the sulfation of phenolic acids such as codon-optimized derivatives of plant phenolic sulfotransferases or catalytic antibodies derived from transition state intermediates of phenolic sulfotransferase catalytic reactions.

The term "plant" includes whole plants, plant organs (e.g., leaves, stems, flowers, roots, etc.), seeds and plant cells and progeny of same. The class of plants which can be used in the method of the invention is as broad as the class of higher plants amenable to transformation techniques, including both monocotyledonous and dicotyledonous plants, as well as certain lower plants such as algae. It includes plants of a variety of ploidy levels, including polyploid, diploid and haploid. The term "plant" farther includes the following classes of plant species:

Dicotyledon (dicot): A flowering plant whose embryos have two seed halves or cotyledons. Examples of dicots are: tobacco; tomato; the legumes including alfalfa; oaks; maples; roses; mints; squashes; daisies; walnuts; cacti; violets; and buttercups.

Monocotyledon (monocot): A flowering plant whose embryos have one cotyledon or seed leaf. Examples of monocots are: lilies; grasses; corn; grains, including oats, wheat and barley; orchids; irises; onions and palms,.

Lower plant: Any non-flowering plant including ferns, gymnosperms, conifers, horsetails, club mosses, liver warts, hornworts, mosses, red algae, brown algae, gametophytes, sporophytes of pteridophytes, and green algae.

The term "promoter" refers to a region of nucleic acid subsequences located upstream and/or downstream from the start of transcription which aid in the recognition, binding and/or initiation of RNA polymerase or other transcription proteins which initiate transcription of an associated gene. A "plant promoter" is a promoter capable of initiating transcription in plant cells. A "plant leucine aminopeptidase promoter" is a promoter derived from a leucine aminopeptidase gene, e.g., by cloning, isolating or recombinantly modifying a native promoter from a leucine aminopeptidase gene.

A "recombinant nucleic acid" comprises or is encoded by one or more nucleic acid which is derived from a nucleic acid which wag artificially constructed. For example, the nucleic acid can comprise or be encoded by a cloned nucleic acid formed by joining heterologous nucleic acids as taught, e.g., in Berger and Kimmel, Guide to Molecular Cloning Techniques, METHODS IN ENZYMOLOGY Vol. 152 Academic Press, Inc., San Diego, Calif. (Berger) and in Sambrook et al. MOLECULAR CLONING-A LABORATORY MANUAL (2nd ed.) Vol. 1–3 (1989) (Sambrook) and in CURRENT PROTOCOLS IN MOLECULAR BIOLOGY, Ausubel, F. M., et al., eds., Greene Publishing Associates, Inc. and John Wiley & Sons, Inc., (1996 Supplement) (Ausubel). Alternatively, the nucleic acid can be synthesized chemically.

As used herein, a "reporter gene construct" is a nucleic acid that includes a "reporter gene" operatively linked to a transcriptional regulatory sequences. Transcription of the reporter gene is controlled by these sequences. The transcriptional regulatory sequences include the promoter and other regulatory regions, such as enhancer sequences, that modulate the activity of the promoter, or regulatory sequences that modulate the activity or efficiency of the RNA polymerase that recognizes the promoter, or regulatory sequences are recognized by effector molecules.

As used herein, the term "nucleic acid" refers to polynucleotides or oligonucleotides such as deoxyribonucleic acid (DNA), and, where appropriate, ribonucleic acid (RNA). The term should also he understood to include, as equivalents, analogs of either RNA or DNA made from nucleotide analogs and as applicable to the embodiment being described, single (sense or antisense) and double-stranded polynucleotides.

As used herein, the term "promoter" means a DNA sequence that regulates expression of a selected DNA sequence operably linked to the promoter, and which effects expression of the selected DNA sequence in cells. The term encompasses "tissue specific" promoters, i.e. promoters, which effect expression of the selected DNA sequence only in specific cells (e.g. cells of a specific tissue). The term also covers so-called "leaky" promoters, which regulate expression of a selected DNA primarily in one tissue, but cause expression in other tissues as well, The term also encompasses non-tissue specific promoters and promoters that constitutively express or that are inducible (i.e. expression levels can be controlled).

The terms "protein", "polypeptide" and "peptide" are used interchangeably herein when referring to a gene product.

The term "recombinant protein" refers to a polypeptide of the present invention which is produced by recombinant DNA, techniques, wherein generally, DNA encoding a specific polypeptide is inserted into a suitable expression vector which is in turn used to transform a host cell to produce the heterologous protein. Moreover, the phrase "derived from", with respect to a recombinant target gene, is meant to include within the meaning of "recombinant protein" those proteins having an amino acid sequence of a native target polypeptide, or an amino acid sequence similar thereto which is generated by mutations including substitutions and deletions (including truncation) of a naturally occurring form of the polypeptide.

As used herein, "recombinant cells" include any cells that have been modified by the introduction of heterologous DNA. Control cells include cells that are substantially identical to the recombinant cells, but do not express one or more of the proteins encoded by the heterologous DNA, e.g., do not include or express a recombinant sulfotransferase gene.

"Small molecule" as used herein, is meant to refer to a composition, which has a molecular weight of less than about 5 kD and most preferably less than about 4 kD. Small molecules can be nucleic acids, peptides, polypeptides, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays of the invention to identify compounds that modulate a target bioactivity.

As used herein, the term "specifically hybridizes" or "specifically detects" refers to the ability of a nucleic acid molecule of the invention to hybridize to at least approximately 6, 12, 20, 30, 50, 100, 150, 200, 300, 350, 400 or 425 consecutive nucleotides of a gene, preferably a plant sulfotransferase gene.

The term "substantially homologous", when used in connection with amino acid sequences, refers to sequences which are substantially identical to or similar in sequence, giving rise to a homology in conformation and thus to similar biological activity. The term is not intended to imply a common evolution of the sequences.

A "tomato acidic leucine aminopeptidase promoter" refers to a native promoter from a tomato acidic leucine aminopeptidase gene. This promoter is optionally recombinantly fused to heterologous nucleic acids.

As used herein, the term "transfection" means the introduction of a nucleic acid, e.g., via an expression vector, into a recipient cell by nucleic acid-mediated gene transfer. Methods for transformation which are known in the art include any electrical, magnetic, physical, biological or chemical means. As used herein, "transfection" includes such specific techniques as electroporation, magnetoporation, $Ca^{++}$ treatment, injection, bombardment, retroviral infection and lipofection, among others. "Transformation" as used herein, refers to a process in which a cell's genotype is changed as a result of the cellular uptake of exogenous DNA or RNA, and, for example, the transformed cell expresses a recombinant form of a target polypeptide or, in the case of anti-sense expression from the transferred gene, the expression of a naturally-occurring form of the target polypeptide is disrupted.

As used herein, the term "transgene" means a nucleic acid sequence (encoding, e.g., one of the target polypeptides, or an antisense transcript thereto) which has been introduced into a cell. A transgene could be partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can also be present in a cell in the form of an episome. A transgene can include one or more transcriptional regulatory sequences and any other nucleic acid, such as introns, that may be necessary for optimal expression of a selected nucleic acid.

A "transgenic plant" refers to any plant, in which one or more of the cells of the plant contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, but rather is directed to the introduction of a recombinant DNA molecule. This molecule may be integrated within a chromosome, or it may be extrachromosomally replicating DNA. In the typical transgenic plants described herein, the transgene causes cells to express a recombinant form of one of the target polypeptides, e.g. either agonistic or antagonistic forms. However, transgenic plants in which the recombinant target gene is silent are also contemplated, as for example, FLP or CRE recombinant dependent constructs. Moreover, "transgenic plant" also includes those recombinant animals in which gene disruption of one or more plant genes is caused by human intervention, including both recombination and antisense techniques.

A "transgenic plant" is one which has been genetically modified to contain and express heterologous DNA sequences, either as regulatory RNA molecules or as proteins. As specifically exemplified herein, a transgenic plant is genetically modified to contain and express at least one heterologous DNA sequence operably linked to and under the regulatory control of transcriptional control sequences which function in plant cells or tissue or in whole plants. As used herein, a transgenic plant also refers to progeny of the initial transgenic plant where those progeny contain and are capable of expressing the heterologous coding sequence under the regulatory control of the plant-expressible transcription control sequences described herein. Seeds containing transgenic embryos are encompassed within this definition as are cuttings and other plant materials for vegetative propagation of a transgenic plant.

When plant expression of a heterologous gene or coding sequence of interest is desired, that coding sequence is operably linked in the sense orientation to a suitable promoter and advantageously under the regulatory control of DNA sequences which quantitatively regulate transcription of a downstream sequence in plant cells or tissue or in plants, in the same orientation as the promoter, so that a sense (i.e., functional for translational expression) mRNA is produced. A transcription termination signal, for example, as polyadenylation signal, functional in a plant cell is advantageously placed downstream of the metal or organometal resistance coding sequence, and a selectable marker which can be expressed in a plant, can be covalently linked to the inducible expression unit so that after this DNA molecule is introduced into a plant cell or tissue, its presence can be selected and plant cells or tissue not so transformed will be killed or prevented from growing. In the present invention, the mercury resistance coding sequence can serve as a selectable marker for transformation of plant cells or tissue. Where constitutive gene expression is desired, suitable plant-expressible promoters include the 35S or 19S promoters of Cauliflower Mosaic Virus, the nos, ocs or mas promoters of *Agrobacterium tumefaciens* Ti plasmids, and others known to the art. Where tissue specific expression of the plant-expressible metal resistance coding sequence is desired, the skilled artisan will choose from a number of well-known sequences to mediate that form of gene expression. Environmentally regulated promoters are also well known in the art, and the skilled artisan can choose from well known transcription regulatory sequences to achieve the desired result.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of a recombinant gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring form of the protein.

The term "vector" refers to a nucleic acid molecule capable of transporting another nucleic acid to which it has been linked. One type of preferred vector is an episome, i.e., a nucleic acid capable of extra-chromosomal replication.

Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The term "wild-type allelle" refers to an allele of a gene which, when present in two copies in a subject results in a wild-type phenotype. There can be several different wild-type alleles of a specific gene, since certain nucleotide changes in a gene may not affect the phenotype of a subject having two copies of the gene with the nucleotide changes.

The phrase "wound-induced polypeptide" refers to a peptide or protein that the plant cells synthesize in response to injury to the plant.

4.3. Antifouling Genetic Traits

In a preferred embodiment, the invention provides methods and compositions for the creation of transgenic plants with antifouling characteristics. The antifouling genetic traits of *Zostera marina* are, at least in part, due to the production of a number of sulfated phenolic compounds such as zosteric acid (para-(sulphooxy) cinnamic acid), and various flavone sulfates including the 7-sulfates of luteolin, diogmetin, apigenin, chrysoeriol and the 7,3'-disulfate of luteolin (Todd et al. (1993) Phytochemistry 34: 401–4). The biosynthesis of these compounds can be stimulated in a host plant by introducing one or more enzymes which catalyze the biosynthesis of these sulfated compounds from one or more common metabolic intermediates. The invention provides for the expression of such biosynthetic enzymes sufficient to support the production of zosteric acid or other sulfated phenolic compounds in a target plant. For example, in a preferred embodiment the common metabolic intermediate is the amino acid phenylalanine and the enzymes introduced include a phenylalanine ammonium lyase, a cinnamate 4-hydroxylase, or a phenolic sulfotransferase. In other embodiments, fewer or additional biosynthetic enzymes are provided to the host plant. For example, in plants which produce adequate levels of a phenolic acid sulfate precursor, such as p-hydroxy coumaric acid, the addition of a single enzyme such as a phenolic sulfotransferase will suffice to confer the antifouling trait of the invention upon the target plant.

4.3.1. Sulfotransferases and Related Sulfur Metabolism Enzymes

In preferred embodiments the invention provides a nucleic acid which encodes a sulfotransferase catalytic activity for introduction into a host plant. The sulfotransferase catalytic activity may be provided by one or more sulfotransferase enzymes such as a phenol sulfotransferase, an alcohol sulfotransferase or an amine sulfotransferase. In certain embodiments, the sulfotransferase is a phenol sulfotransferase, an hydroxysteroid sulfotransferase or a flavonol sulfotransferase. In preferred embodiments of the invention, the sulfotransferase is a phenol sulfotransferase.

Sulfation in plants has been shown to play a critical role in intermolecular recognition and signaling processes, as indicated by the requirement of a sulfate moiety for the biological activity of gallic acid glucoside sulfate in the seismonastic and gravitropic movement of plants (Varin et al. (1997) The Plant J 12: 831–7), and of Nod RM1 in the cortical cell division during early nodule initiation in *Rhizobium meliloti*-alfalfa interaction (Truchet et al. (1991) Nature 351; 670–3). Several plant sulfotransferase genes have been cloned and their encoded proteins have been characterized at the biochemical level (see Varin et al. (1997) FASEB J 11: 517–25). Furthermore, still other genes which encode cytosolic sulfotranserases have been isolated from several vertebrate species (see Weinshilboum et al. (1997) FASEB J 11: 3–14). These sulfotransferase enzymes share significant homology and also demonstrate a conserved intron/exon structure, which is characteristic of genes having a common evolutionary origin. Accordingly, the invention provides a number of known sulfotransferase encoding genes and enables the cloning of still other sulfotransferase encoding genes, by virtue of their conserved structure, for use in the invention. The sulfotransferases include a number of subfamilies with particular substrate specificities including the phenol sulfotransferases (PST), the hydroxysteroid sulfotransferases (HSST), and, in plants, the flavonol sulfotransferases (FST), members of which share at least 45% amino acid sequence identity. Genes encoding a phenol sulfotransferases (PST) activity are particularly preferred in the method of the present invention.

Phenol sulfotransferase enzymes of the invention include those obtained from animal and plant species, including plant species other than *Zostera marina*. For example, phenol sulfotransferase encoding genes for use in the invention include those comprising the PST gene family, which includes both phenolsulfotransferase and estrogen sulfotransferase encoding genes (Weinshilboum et al. (1997) FASEB J 11: 3), including: the human hTSPST1 gene (GenBank Accession No. L19999, Wilborn et al. (1993) Mol. Pharmacol. 43: 70–77); the human hTSPST2 gene (GenBank Accession No. X78282, Ozawa et al. (1995) Pharmacogenetics 5: S135); the human hTLPST gene (GenBank Accession No. L19956, Wood et al. (1994) Biochem Biophys Res Commun 198: 1119); the human hEST gene (U08098, Aksoy et al. (1994) Biochem Biophs Res Commun 200; 1621); the bovine BPST gene ((GenBank Accession No. 35353, Schauss et al. (1995) Biochem J 311: 1); the bovine bEST gene (GenBank Accession No. X56395, Nash et al. (1988) Austral J Biol 41: 507); the rat rPST gene (Genbank Accession Nos. X52883 and S42994, Ozawa et al. (1990) Nucleic Acids Res 18: 4001); the rat r1B1ST gene (GenBank Accession No. U38419, Sakakibara (1995) J Biol Chem 270: 30470); the rat rAAFST gene (GenBank Accession No, 12239, Nagata (1993) J Biol Chem 268; 24720); the rat rEST gene (GenBank Accession No. M86758, Demyan et al. (1992) Mol Endocrinol 6: 589); the rat rEST-6 gene (GenBank Accession No. S76490, Falany et al. (1995) J Steroid Biochem Mol Biol 52: 35); the mouse mPST gene (GenBank Accession No. L02331, Kong et al. 91993) Biochim Biophys Res Acta 1171: 315); the mouse met gene (GenBank Accession No. S78182, Song et al. (1995) Endocrinol 136: 2477); the guinea pig gpEST (GenBank Accession No. S45979, Mol Endocrinol 6: 1216); and the *Macaca fascicularis* mfPST gene (GenBank Accession No. D85514). In certain instances, a sulfotransferase gene which encodes an enzyme with a presumptive specificity to hydroxysteroids or flavonols may also be used in the invention. For example, the *Arabidopsis thaliana* gene atST (GenBank Accession No. Z46823, Lacomme et al. (1996) Plant Mol Biol 30: 995) which is most homologous in sequence to the flavonol sulfotransferase family, but may have may possess a different or broader substrate specificity which encompasses phenolic compounds. Similarly, four other plant genes encoding sulfotransferases with presumptive flavonol substrate specificities have been identified including: the *Flaveria chloraefolia* fcFST3 gene (GenBank Accession No. M84135, Varin et al. (1992) Proc Natl Acad Sci USA 89: 1286); the *Flaveria bidentis* fbFST3 gene (GenBank Accession No. U10275, Plant Physiol 106: 485); the *Flaveria chloraefolia* fcFST4 gene (GenBank Accession No. M84136, Varin et al. (1992) Proc Natl Acad Sci USA 89: 1286); and the *Flaveria bidentis* fbFST1 gene (GenBank Accession No. U10277, Ananvoranich et al. (1995) Plant Physiol 107: 1019). These genes may be used in their native state, or altered to optimize their phenol sulfotransferase specificity and/or codon utilization in the target host plant as described further below.

The invention further provides methods for cloning still other genes which encode a phenol sulfotransferase activity and for developing synthetic sulfotransferase-encoding genes. The PST gene family described above comprises a set of genes which are at least about 60% identical in amino acid sequence. Certain amino acid sequence motifs within the family are particularly well conserved throughout phylogeny and are therefore useful in cloning new species of PST genes. For example, certain signature sequences of the PSTs are involved in the binding of 3'-phosphoadenosine-5'-phosphosulfate (PAPS), the cosubstrate for the sulfonation reaction. Alignment of the amino acid sequences of sulfotransferase enzymes has revealed at least four areas of sequence that are highly conserved throughout phylogeny (Varin et al. (1992) Proc Natl Acad Sci USA 89: 1286). Two of these regions (region I and region IV) together appear to encode the PAPS substrate binding domain. These regions are particularly well conserved and occur near the amino and carboxy terminus of the sulfotransferase enzyme respectively. Regions I and IV are separated by approximately 190 to 210 amino acid residues. These regions comprise the consensus sequence:
TYPKSGT(N/T)W-$X_{190-210}$-RKGXXGDWKXXFT, where N/T may be an asparagine or a threonine, X may be any amino acid residue and $X_{190-210}$ represents the 190 to 210 amino acid residues intervening between conserved Region I and conserved Region IV which are shown in bold. This sequence motif occurs in virtually all known sulfotransferase proteins and, accordingly, is useful in cloning new species of this gene family using nucleic acid probes directed to conserved regions of the sulfotransferase-encoding gene or polypeptide probes, such as monoclonal antibodies, directed to conserved region of the sulfotransferase protein.

For example, these conserved amino acid regions may be used to design oligonucleotide pools corresponding to candidate nucleic acid sequences which may encode these regions for use in oligonucleotide hybridization cloning or polymerase chain reaction amplification cloning of a *Zostera marina* sulfotransferase encoding gene (see Sambrook et al. (1989) Molecular Cloning, 2nd edition, CSH Press). In particular, the genetic code may be used to design a pool of 27 base oligonucleotides comprising all possible nucleic acid sequences which may encode the 9 amino acid residue region I. The redundancy of the genetic code provides that this pool of oligonucleotides would have a complexity of approximately $2 \times 10^4$, however the size of the pool may be reduced by eliminating certain codon sequences which are disfavored in plants in general or the target plant, from which the sulfotransferase is to be cloned, in particular (see e.g. Duret and Mouchiroud (1999) Proc Natl Acad Sci USA 96:4482; Chiapello et al. (1998) Gene 209:GC1). Furthermore a second pool of oligonucleotides comprising all possible nucleic acid sequences which may encode the conserved 9 amino acid residues of the 13 amino acid residue region IV may be designed using the genetic code. The nonconserved segments of region IV (i.e. the "X" residues in the region IV consensus sequence indicated above) may be accounted for by inserting three inosine nucleotide residues for each nonconserved residue, since inosine is a "neutral" base which pairs adequately with any of the four conventional bases (see section 11.17 of Sambrook et al., ibid.). Accordingly, a pool of 39 base oligonucleotides with a complexity of approximately $1 \times 10^4$ would hybridize to all region IV-encoding segments of the target organism's genomic DNA or cognate cDNA. These two oligonucleotide pools may be used individually or in combination to screen a genomic or cDNA library of, for example, *Zostera marina* (see e.g. sections 8.46–8.49 of Sambrook et al., ibid.). Preferably, a sense oligonucleotide pool of conserved region I may be combined with an antisense oligonucleotide pool of conserved region IV and used to amplify sulfotransferase encoding gene segments from *Zostera marina* or another organism. The polymerase chain reaction approach is particularly desirably since: the amplification will only occur where both conserved regions I and IV occur in close proximity: the size of amplification products derived from a sulfotransferase-encoding cDNA sequence can be predicted from the conserved spacing between regions I and IV to be approximately 266 base pairs; and further amplification of a region I oligonucleotide pool/region IV oligonucleotide pool amplification with a region II oligonucleotide pool and/or a region III oligonucleotide pool (see Chap. 22 of Weinshilboum and Otterness (1994) Handbook of Experimental Pharmacology 112: 45) would result in selective enrichment for bona fide sulfotransferase-encoding sequences. The partial cDNA sulfotransferase sequences thus obtained are then used as probes in screening a, for example, *Zostera marina* cDNA library in order to recover the entire sulfotransferase coding sequence for use in the invention.

The invention still further provides for mutated derivatives of native sulfotransferase gene sequences from an organism such as *Zostera marina*. For example, the gene sequence of a *Zostera marina* sulfotransferase may be altered so as to optimize codon utilization and increase expression in the target host plant. In addition, a synthetic sulfotransferase encoding gene may be used in the method of the invention. For example, catalytic antibodies, designed to bind to a phenol sulfotransferase catalytic intermediate antigen, may be generated using methods known in the art (see e.g. Jacobsen and Schultz (1995) Curr Opin Struct Biol 5: 818). The nucleic acid encoding these antibodies with phenol sulfotransferase catalytic activity may then be introduced into the target host plant to provide a "synthetic" PST activity of the invention.

The sulfation of phenolic compound occurs through the catalytic action of a phenol sulfotransferase acting upon a phenol substrate and a 3'-phosphoadenosine-5'-phosphosulfate (PAPS) sulfate donor (Bic and Leustek (1998) Curr Opin Plant Biol 1:240). The PAPS sulfate donor in turn is generated through the action of an APS kinase (AK), which catalyzes the phosphorylation of 5'-adenylylsulfate (APS) to yield PAPS. APS is a branch point intermediate that is used both for the sulfation pathway leading to synthesis of various sulfated compounds (such as phenol sulfates) as well as the reduction pathway, which leads to the formation of cysteine. Ultimately, the organic sulfate donor is derived from APS, which is generated through the action of an ATP sulfurylase (AS) acting upon ATP and inorganic sulfate. Accordingly, the sulfur metabolism of a target plant may be altered to optimize expression and/or regulation of zosteric acid biosynthesis by the host plant of the invention by altering the expression of one or more of these enzymes/activities. For example, in certain embodiments, the invention provides a transgenic AS or AK-encoding gene. AS-encoding genes for use in the invention include: the *Arabidopsis thaliana* ATP sulfurylase ASAL gene (GenBank Accession No. U40715, Logan et al. (1996) J Biol Chem 271: 12227); the *Allium* cepa ATP-sulfurylase gene (GenBank Accession No AF21154); the *Lotus japonicus* ATP sulfurylase gene (GenBank Accession No. AW164083); the *Arabidopsis thaliana* met3–1 ATP sulfurylase gene (GenBank Accession No. X79210). In certain instances a single polypeptide has been shown to possess both an ATP sulfurylase and a 5'-adenylylsulfate kinase activity. For example, an ATP sulfurylase/APS kinase encoding gene has been isolated from mouse (GenBank Accession No. U34883, Li et al. (1995) J Biol Chem)70: 1945), and human (GenBank Accession No. AF033026, Yanagisawa (1998) Biosci Biotechnol Biochem 62: 1037) sources.

Still other sulfotransferase genes of the invention include: *Mus musculus* phenolsulfotransferase cDNA (GenBank Accession No.AF033653), *Canis familiaris* phenolsulfotransferase cDNA (GenBank Accession No. D29807), *Macaca fascicularis* phenol sulfotransferase subunit cDNA (GenBank Accession No.D85514), *Homo sapiens* phenol sulfotransferase 1 (STP1) cDNA (GenBank Accession No. U71086), *Homo sapiens* phenol sulfotransferase cDNA (GenBank Accession No. L19999), *Homo sapiens* catecholamine sulfating phenol sulfotransferase (STM) cDNA (GenBank Accession No. U37686), *Bos taurus* tracheobronchial phenol sulfotransferase cDNA (GenBank Accession No.U35253), *Homo sapien* phenol sulfotransferase cDNA (GenBank Accession No. U26309), *Homo sapien* aryl sulfotransferase cDNA (GenBank Accession No. L10819), and *Homo sapien* thermolabile monamine, M form phenol sulfotransferase (STM) cDNA (GenBank Accession No. U08032).

In other aspects, the invention takes advantage of a biosynthetic pathwasy in marine algae which is responsible for synthesis of dimethylsulphoniopropionate (see Gage et al. Nature (1997) 387: 891–894. This pathway converts methionine by transamination, reduction and 5-methylation to give the novel sulphonium compound 4-dimethylsulphonio-2-hydroxybutyrate (DMSHB), which is oxidatively decarboxylated to DMSP. The enzymes responsible for these conversions including those known in the art, are incorporated into certain preferred transgenic plant strategies of the invention.

4.3.2. Phenylalanine Ammonium Lyases

In certain embodiments, the invention provides a nucleic acid which encodes a phenylalanine ammonium lyase (PAL) activity. Phenylalanine ammonia-lyase catalyzes the deamination of phenylalanine to form trans-cinnamic acid, a precursor in the biosynthesis of zosteric acid and the first step in phenylpropanoid synthesis. In tobacco leaf tissue, the level of PAL is a dominant factor in regulating the flux into the phenylpropanoid biosynthetic pathway, and in tobacco stem tissue PAL levels affect the rate of accumulation of lignin, a major product of the phenylpropanoid pathway (Bate et al. (1994) Proc Natl Acad Sci USA 91: 7608–12). Furthermore, there is evidence that PAL, gene expression is induced by wounding (Diallinas et al. (1994) Plant Mol Biol 26: 473–9) and may plan an important role in pathogen defense mechanisms through its involvement in the synthesis of the phenylpropanoid product chlorogenic acid (Maher et al. (1994) Proc Natl Acad Sci USA 91: 7802–6). Accordingly, the invention provides methods and compositions for increasing the amount of phenylalanine ammonialyase activity in a host plant, thereby increasing the flux of metabolites into the phenylpropanoid pathway and stimulating zosteric acid biosynthesis. In addition the increased flux into the phenylpropanoid pathway increases the synthesis of other phenylpropanoid products such as chlorogenic acid which are involved in host defense mechanisms. In preferred embodiments, the invention provides PAL-encoding nucleic acids for transformation into a host plant. Phenylalanine ammonia-lyase encoding genes have been cloned from a number of different plant, animal and microbial species. For example, in tobacco PAL is encoded by a small family of two to four unclustered genes (Pellegrini et al. (1994) Plant Physiology 106: 677–86) and corresponding cDNAs for the palA gene (GenBank Accession No. AB008199) and the palB gene (GenBank Accession No. AB008200) have been isolated. Still other PAL encoding genes include; the *Amanita muscaria* PAL cDNA (GenBank Accession No. AJ010143), and the *Vitis vinifera* PAL cDNA (GenBank Accession No.X75967).

4.3.3. Cinnamate 4-Hydroxylases

The invention further provides cinnamate 4-hydroxylase enzymes and related enzymatic activities which promote the hydroxylation of cinnamic acid to p-hydroxy coumaric acid. In plants, cinnamate 4-hydroxyylase is a major P450 enzyme and catalyzes the first oxidative step of the phenylpropanoid pathway. This pathway is critical to the production of plant surface components (suberins), plant cell walls (lignins), plant ultraviolet filters (coumarins), plant pigments (flavonoids) and plant defenses against phathogens (phytoalexins). Accordingly, as with phenylalanine ammonium lyase, most target host plants provide a certain level of endogenous activity of this enzyme. The invention optionally provides heterologous cinnamate 4-hydroxylase-encoding transgenes for use in a target host plant to supplement endogenous levels of this enzyme. In particular, the heterologous transgene may be modified so as to be constitutive or inducible by some stimuli. In preferred embodiments, the stimulus is a plant defense signal. The modified cinnamate 4-hydroxylase is designed to provide optimal doses of sulfated phenolic compounds, preferably zosteric acid, to the transgenic target host plant.

Suitable cinnamate 4-hydroxylase enzymes are known in the art. For example, a novel cinnamate 4-hydroxylase-encoding gene from French bean (i.e. CYP73A15) has been engineered for expression in yeast (Nedelkina et al. (1999) Plant Mol Bio 39: 1079–90). A large number of cinnamate 4-hydroxylase encoding sequences are available for use in the method of the invention. For example; the *Phaseolus vulgaris* cinnamate 4-hydroxylase cDNA (GenBank Accession No. PV09447), the *Arabidopsis thaliana* cinnamate 4-hydroxylase CYP73A5 cDNA (GenBank Accession No. U37235), the *Mesembryanthemum crytallinum* cinnamate 4-hydroxylase cDNA (GenBank Accession No.AF097664), the *Petroselinum crispum* trans-cinnamate 4-monooxygenase cDNA (GenBank Accession No. L38898), the *Arabidopsis thaliana* trans-cinnamate 4-hydroxylase cDNA (GenBank Accession No.D78596), the *Arabidopsis thaliana* cinnamate 4-hydroxylase (atC4H) cDNA (GenBank Accession No. U71081), the *Catharanthus roseus* cinnamate 4-hydroxylase (CYP73) cDNA (GenBank Accession No. Z32563), and the *Vigna radiata* cinnamate 4-hydroxylase cDNA (Genfank Accession No. L07634).

The hydroxylation of cinnamic acid to p-hydroxy coumaric acid is similar to the chemical conversion of phenylalanine to tyrosine by the monooxygenase phenylalanine hydroxylase. This enzyme uses molecular oxygen to convert phenylalanine to para-hydroxy phenylalanine (i.e. tyrosine), creating one molecule of water and converting the reduced coenzyme tetrahydrobiopterin into the oxidized form dihydobiopterin. The reduced form of tetrahydrobiopterin is subsequently regenerated from dihyrobiopterin by reduction with NADPH. Tyrosine hydroxylase acts in a similar fashion to catalyze the hydroxylation of tyrosine to form 3,4-dihydroxyphenylalanine (dopa). Accordingly, the invention optionally provides phenylalanine hydroxylage enzyme functions and tyrogine hydroxylage enzyme functions for promoting the formation of hydroxylated phenolic compounds. In preferred embodiments these hydroxylated phenolic compounds are further sulfated to form, for example, m,p-disulfoxy caffeic acid.

4.4. Salt Tolerance Genetic Traits

Another aspect of the invention is the production of salt tolerance in a target transgenic host plant. In preferred embodiments, the salt tolerance is conferred on the target host by supplying one or more heterologous genes which promote physiological processes which are protective of salt exposure. In particularly preferred embodiments, these salt resistance genes are derived from a marine eel grass such as *Zostera marina*.

Salt tolerant plants have a number of different strategies for dealing with the occurrence of environmental salt Accordingly, a number of different plant genes effecting these diverse physiological strategies, may be used in the method of the invention to produce genetically modified host plants with increased salt tolerance. For example, the desert plant *Mesembryanthemum crystallinum* appears to respond to saline growth conditions by an age-dependent transition from $C_3$ to crassulacean acid metabolism (CAM), and by the ability to accumulate high sodium ion concentrations in the vacuole of young, growing, aerial parts of the plant, balanced by the synthesis of compatible solutes in the cytoplasm. These adaptive responses allow *M. crystallinum* to increase water use efficiency through the regulation of stomatal functioning and osmotic potential. CAM promotes the closing of stomata during the day and the fixation of carbon through the Calvin cycle by employing the carbon dioxide derived from the decarboxylation of malate by malic enzyme. In the evening, stomata open and allow for the influx of carbon dioxide which is fixed into malate by phospho-enol-pyruvate carboxylase (PEPC) and stored in the vacuole.

Accordingly, the method of the invention provides for nucleic acids which encode enzymes which facilitate these plant $C_3$ processes. For example, the increased assimilation of carbon dioxide into malate is facilitated by the induction of genes which encode enzymes that function in malate metabolism including: the CAM-specific PEPC isogene Ppcl whose expression is induced by salt stress (Cushman et al. (1989) Plant Cell 1:715–25); the NAD-glyceraldehyde-3-phosphate dehydrogenase gene Gdp1 (Ostrem et al. (199) J Biol Chem 265: 3497–3502); the cytosolic NADP-malic enzyme encoding gene Mod1 (Cushman et al. (1992) Eur J Biochem 208: 259–66); and the chloroplast NADP-malate dehydrogenase encoding gene Mdh1 (Cushman et al. (1993) Photosynth Res 35:15–27). In one embodiment, the mRNA encoding one of these malate metabolic genes may be functionally linked to a constitutive or inducible promoter and the resulting construct may be used to create a transgenic host plant. In another embodiment, a malate metabolic gene locus, including its naturally occurring promoter and enhancer sequences, may be transferred into the host plant. For example, the Ppcl gene may be obtained as a cDNA (e.g. the *Lycopersicon esculentum* Ppc1 cDNA-GenBank Accession No. AJ243416; or the soybean Ppc1 cDNA-GenBank Accession No. D13998) or as a genomic DNA clone (e.g. the *Arabidopsis thaliana* genomic locus on chromosome 1-GenBank Accession No. AC008075). Therefore, in one aspect of the present invention, one or more such malate metabolism-promoting enzymes is provided to a target host plant in order to promote the CAM pathway and thereby decrease water loss and facilitate drought and salt-tolerance.

Another aspect of the invention invokes another strategy adopted by plants for growth in high salt conditions via the ability to effectively distribute $Na^+$ and still maintain cellular water homeostasis. Salt tolerant plants (halophytes) have the ability to accumulate $Na^+$ whereas salt-intolerant plants (glycophytes) attempt to exclude environmental $Na^+$. Halophytes and galophytes maintain similar levels of cytoplasmic $Na^+$, and the $Na^+$ accumulated by halophytes is stored within cytoplasmic vacuoles. Vacuolar uptake is facilitated by a $Na^+/H^+$ antiporter, or exchanger (Barkla et al. (1995) Plant Physiol 105: 549–56). The proton motive force necessary for active vacuolar transport of $Na^+$ is further facilitated by the activity of the vacuolar $H^+$-ATPase (V-ATPase) and or $H^+$-pyrophosphatase (V-PPase). The active transport of $Na^+$ into the vacuole serves to maintain cytoplasmic $Na^+/K^+$ ratios, avoid cytoplasmic $Na^+$ toxicity, and maintain osmotic balance in a high $Na^+$ environment. The method of the present invention provides for the creation of transgenic host plants which have an increased ability to localize cytoplasmic $Na^+$ into vacuoles, and thereby show and increased tolerance to environmental salt. For example, a $Na^+/H^+$ antiport activity has been reported in the salt tolerant plant *M. crytallinum* (Barkla et al. (1995) Plant Physiol 105: 549–56), and the salt-inducible increase in this antiport activity has further been correlated with a similar increase in V-ATPase activity (Vera-Estrella et al. (1999) Plants 207: 426–35). Therefore, in another aspect of the invention, one or more vacuolar transporter activities is supplied to the transgenic host. For example, the *Arabidopsis thaliana* $Na^+/H^+$-exchanger is encoded by the NAhe1 gene (cDNA sequence corresponds to GenBank Accession No. AF056190), the *Oryza sativa* $Na^+/H^+$ exchanger is encoded by the Ovp2 gene (cDNA sequence corresponds to GenBank Accession No. D45384), and the *Oryza sativa* V-PPase is encoded by Ovp1 (cDNA sequence corresponds to GenBank Accession No. D45383). In certain applications, these genes may be expressed from a strong constitutive or regulatable plant promoter and the increased dose of these genes supplies the host plant with a greater capacity to store $Na^+$ in cytoplasmic vacuoles. In certain preferred embodiments, a gene encoding a vacuolar transporter activity is derived from a salt-tolerant species of plant and its expression and/or the biochemical properties of the encoded transporter provide a host target plant with an increased tolerance for environmental salt.

In another embodiment of the invention, salt tolerance is conferred upon the transgenic host plant by providing one or more aquaporin water channel-encoding genes. The "aquaporins" are a group of channels conserved in animals, plants and micro-organisms that facilitate the passive movement of water across membranes. In plants, aquarporins fall into two distinct subclasses of the MIP family—the putative plasma membrane intrinsic proteins (PIPs) and the putative tonoplast intrinsic proteins (TIPs) (see Yamada et al. (1995) Plant Cell 7: 1129–42). These water channels are believed to function in facilitating cellular hydraulic conductivity during periods of water shortage or following exposure to salt. For example, transcripts encoding a pea shoot MIP homolog have been shown to be induced by water deficit (Guerrero et al. (1990) Plant Mol Biol 15: 11–26). Furthermore, a sunflower TIP-encoding gene has been shown to be drought-induced (Sarda et al. (1997) Plant J. 12: 1103–11). Accordingly, the invention optionally provides one or more MIP aquaporin water channel-encoding genes to the transgenic host plant. For example, the MIP aquaporin water channel-encoding gene may be a genetically engineered gene comprised of an heterologous promoter and an MIP aquaporin-encoding cDNA selected from the group consisting of: the *Arabidopsis thalaina* delta tonoblast integral protein cDNA (GenBank Accession No. U39485, Daniels (1996) Plant Cell 8: 587–99); the *Vernicia fordii* aquaporin cDNA (GenBank Accession No. AF047173, Tang et al. (1998) Plant Physiol 117: 717); the *Medicago sativa* tonoplast intrinsic protein homolog MSMCP 1 cDNA (GenBank Accession No. AF020793, Gregerson et al. (1998) Plant Physiol 116: 869); the *Phaseolus vulgaris* aquaporin Mip-1 eDNA (Genbank Accession No. U97023, Campos et al. (1997) Plant Physiol. 115: 313); the *Mesembryanthemum crystallinum* aquaporin mipB cDNA (GenBank Accession No. L36097, Yamada et al. (1995) Plant Cell 7: 1129–42); and the *Atriplex canescens* aquaporin cDNA (GenBank Accession No. U18403, Cairney et al. (1995) Plant Physiol 108: 1291). In certain embodiments, the invention provides for the salt-inducible down regulation of a PIP subfamily aquaporin in conjunction with the engineering of a halophilic salt-tolerance profile in which the target plant selectively accumulates $Na^+$. Such a mechanism is employed, for example, by the salt tolerant halophile *M. crystallinum*, which decreases levels of expression of three MIP-encoding genes (MipA, MipB and MipC) upon salt-stress (Yamada et al. (1995) Plant Cell 7: 1129–42). In preferred embodiments, the salt-repressible MIP expression is conferred by utilizing a salt-inducible plant promoter which has been functionally linked to an antisense nucleic acid which interferes with the expression of an endogenous aquaporin. In another embodiment, the transgenic target host plant is supplied with a genomic *M. crystallinum* MipA, MipB or MipC gene locus that includes an endogenous salt-repressible *M. crystallinum* promoter element and an aquaporin coding sequence.

In yet another embodiment, the invention provides a transgenic host target plant with non-sodium ion compatible solutes which serve to compensate the osmotic potential of the cytoplasm under water-limiting growth conditions. In a preferred embodiment, these complatible solutes balance the accumulation of sodium ions in the vacuoles and are provided as a low molecular weight compound that can accumulate to high concentrations within the cell without inducing negative effects on other metabolic processes (see e.g. Bohnert et al. (1995) Plant Cell 7: 1099–111). Such preferred compatible solutes include: proline, beataines, fructans, and sugar alcohols such as mannitol, sorbitol, ononitol, pintol and myo-inositol. The accumulation of a preferred compatible solute may be effected by providing the transgenic host target plant with an appropriate regulatory or biosynthetic gene which increases cytoplasmic levels of one or more compatible solute molecules, Examples include; the Vignia pyrroline-5-carbolylate synthase gene (P5CS, a key enzyme in proline biosynthesis) (GenBank Accession No. AJ005686, Stines et al. (1999) Plant Physiol 120: 923), the *M. crysallinum* L-myo-inositol methyltransferase gene (IMTI, a key enzyme in pinitol biosynthesis) (GenBank Accession No. U63634), the *M. crysallinum* myo-ionsitol 1-phosphate synthase gene (INPS, another key enzyme in the pinitol biosynthetic pathway) (GenBank Accession No. U32511, Ishitani et al. (1996) Plant J 9: 537–48). Other examples of compatible solute-increasing genes include the pinitol biosynthetic genes inositol-1-phosphatase (IMP1, e.g. GenBank Accession No. AF037220) and ononitol epimerase (OEP).

In another aspect of the invention, the salt-tolerance engineering of the transgenic host plant includes one or more genes which facilitate the phytoremediation of saline soils. Bioremediation exploits the capacity of living organism to remove toxic compounds from contaminated water or soils. In the case of plants (phytoremediation), applications include the removal of heavy metals by "hyperaccumulator" plant species that are able to concentrate these heavy metals at higher levels than those found in the soil (See e.g. Raskin et al. (1994) Current Biology 5: 285–90). As the foregoing salt-tolerance genes in certain instances function by accumulating vacuolar sodium ions to concentrations higher than those found in a normal non-transgenic host plant, they may provide the transgenic target host plant with the ability to bioremediate saline soil.

4.5. Hypoxia Resistance Genetic Traits

Another aspect of the invention is the production of hypoxia tolerance in a target transgenic host plant. In preferred embodiments, the hypoxia tolerance is conferred on the target host by supplying one or more heterologous genes which promote physiological processes which are protective of oxygen deprivation, particularly oxygen deprivation in a root tissue. In particularly preferred embodiments, these hypoxia resistance genes are derived from a marine eel grass such as *Zostera marina*.

For example, under anoxic root conditions, *Zostera marina* accumulates the amino acids alanine and g-amino butyric acid, while levels of glutamate and glutamine decline (Pregnall et al. (1984) Marine Biology 83: 141–7). This adaptive metabolic response appears to facilitate adaptation to diurnal root anoxia in the shallow-water marine sediments occupied by this unique vascular marine plant. Indeed the seagrasses are uniquely successful angiosperms in shallow-water coastal marine habitats, which are characterized by the presence of periodically anoxic reducing sediments that contain a high organic content and have high rates of ammonium regeneration (see Izumi et al. (1982) Mar. Biol. 66: 59–65). Terrestrial plants commonly effect the production of ethanol from anaerobic root metabolism in response to anoxia brought on by flooding, *Zostera marina* appears to maintain a high level of expression of alcohol dehydrogenase activity under both aerobic and anaerobic conditions (see Smith et al. (1988) Marine Biology 98: 131–41). The high constitutive levels of ADH activity in *Zostera marina* appear to facilitate its considerable hypoxia tolerance. Accordingly, in a preferred embodiment of the invention, a transgenic host target plant is supplied with one or more ADH-encoding genes. These genes may be expressed from their endogenous source promoters, or may be genetically modified for expression from heterologous constitutive or hypoxia-inducible promoters. Examples of ADH-encoding cDNAs for use in the invention include: *Gossypium arboreum* AdhC cDNA (GenBank Accession No. Af036574); *Arabidopsis thaliana* Yo-0 Adh cDNA (GenBank Accession No. D8424–9); *Arabidopsis thaliana* Ita0 Adh cDNA (GenBank Accession No. D84248); *Arabidopsis thaliana* Gr-1 Adh cDNA (GenBank Accession No. D84247); *Arabidopsis thaliana* Es-0 Adh cDNA (GenBank Accession No. D84246); *Arabidopsis thaliana* Ci-0 Adh cDNA (D84245); *Arabidopsis thaliana* Chi-0 Adh cDNA (GenBank Accession No. D84244); *Arobidopsis thaliana* Bs-0 Adh cDNA (GenBank Accession No. D84243); *Arabidopsis thaliana* Bla-10 Adh cDNA (GenBank Accession No. D84242); *Arabidopsis thaliana* Bl–1 Adh cDNA (GenBank Accession No. D84241); *Arabidopsis thaliana* Al-0 Adh cDNA (GenBank Accession No. D84240); and *Oryza sativa* AdhIII cDNA (GenBank Accession No. U77637). The invention further relates to transgenic plants capable of increased levels of ethanol fermentation and, in particular, ethanol fermentation in response to hypoxia. Accordingly, in addition to constitutive and inducible alcohol dehydrogenase transgenes provided above, the invention provides transgenes encoding glycolytic enzymes which are constitutive or, preferably, hypoxia-inducible. Preferred glycolytic enzymatic functions for use in the invention including the glycolysis pathway control functions such as hexokinase (e.g. an *Arabidopsis thaliana* hexokinase 1 cDNA (AtHXK1; GenBank Accession No. U28214) or hexokinase 2 cDNA (AtHXK2; GenBank Accession No. U28215)); phosphofructokinase (e.g. an *Arabidopsis thaliana* genomic clone encoding phophofructokinase alpha subunit (GenBank Accession No. AC015450) or pyruvate kinase (e.g. an *Arabidopsis thaliana* genomic clone encoding pyruvate kinase (GenBank Accession No. AC011698).

Other glycolytic function encoding functions for use in the invention include: phophoglucose isomerase-encoding genes and cDNAs, aldolase-encoding genes and cDNAs, triose phosphate isomerase-encoding genes and cDNAs, glyceraldehyde 3-phosphate dehyrdrogenage-encoding genes and cDNAs, phosphoglycerate kinase-encoding genes and cDNAs, phosphoglyceromutase-encoding genes and cDNAs, and enolase-encoding genes and cDNAs. Numerous such genes and cDNAs can be identified at, for example, www.ncbi.nlm.nih.gov/entrez/query. The genes and cDNAs may be obtained from the referenced sources or may be obtained readily in the laboratory using appropriate probes and genomic libraries, or, more readily, by pcr amplification using forward and reverse primers on total cDNA derived from the appropriate source as is known in the art.

*Zostera marina* also appears to divert carbon away from ethanol into the production of other products such as alanine and g-amino butyric acid during periods of anaerobiosis. These biosynthetic reactions have the further desirable effect of assimilating nitrogen without being toxic to the plant. Furthermore these products which accumulate under anaerobic conditions permit a rapid return to aerobic respiration and ammonium assimilation upon the resumption of shoot photosynthesis. Accordingly, the invention provides one or more gene or gene homologs which encode activities that promote *Zosiera marina* hypoxia/anoxia-tolerance promoting biosynthetic processes. Examples include: a glutamate decarboxylase encoding cDNA such as *Gallus gallus* GAD67, GenBank Accession No. AF030355; *Arabidopsis thaliana* glutamate decarboxylase GAD, GenBank Accession No. U10034; *Arabidopsis thaliana* glutamate decarboxylase GAD2, GenBank Accession No. U46665; *Nicotiana tabacum* NtGAD1, GenBank Accession No. AF020425; or *Petunia hybrida* GAD, GenBank Accession No. L16977). Yet other functions which fall within this aspect of the invention are hypoxia-inducible biosynthetic activities which increase the rate of glycolysis—e.g. a synthetic gene comprised of an hypoxia-inducible promoter functionally linked to a cDNA encoding a key glycolytic enzyme function such as hexokinase, phosphofructokinase or pyruvate kinase. Also included are hypoxia-inducible pentose phosphate pathway controlling activities and hypoxia-repressible Kreb's cycle controlling activities such as citrate synthetase, isocitrate dehydrogenase, and a-ketoglutarate dehydrogenase.

Also included in this aspect of the invention are genes that provide general molecular/metabolic defense and rescue mechanisms for surviving oxygen deprivation (see e.g. Hochachka et al. (1996) Proc. Natl. Acad. Sci. USA 93: 9493–98). In this aspect of the invention, a host genome may be modified to provide for increased or decreased expression of a particular target gene under conditions of hypoxia or anoxia. For example, in the case of genes whose down-regulation facilitates survival and recovery under anoxic conditions, an antisense genetic construct which interferes with the target gene's translation may be provided. Alternatively, in the case of a particular target genes whose up-regulation facilitates survival and recovery under anoxic conditions, a cognate hypoxia-inducible transgene may be provided. Examples of gene-encoded functions whose up-regulation appears to facilitate survival and recovery from hypoxic or anoxic conditions include "ATP energetic efficiency" functions such as glycolytic functions and AP1 gene activator functions. Still other functions which are adaptively up-regulated in hypoxic cells are enzymes which function in the detoxification of end products derived from oxidative metabolism during a subsequent anoxia recovery period (see e.g. Moffat et al. (1994) J Biol Chem 269: 16397–402). Such protective functions include superoxide digmutases and glutathione 9-trangferases. Examples of gene-encoded functions whose down-regulation appears to facilitate survival and recovery from hypoxic or anoxic conditions include "energy turnover" functions such as protein synthesis, protein degradation, $Na^+/K^+$ pumping, and gluconeogenesis. In some particular instances, down regulation of one of these functions may be mediated by up-regulation of a repressor of that function. For example, protein synthesis can be down-regulated by increasing the expression of EF1a, which is an inhibitor of elongation of the nascent polypeptide that acts by forming nonfunctional complexes with polysome-associated mRNAs. Accordingly, the invention provides, for example, an EF1a encoding cDNA (e.g. the *Nicotiana tabacum* EF1a cDNA, GenBank Accession No. AF120093) under the control of an hypoxia-inducible promoter. Another function to be down-regulated under the method of the invention is membrane permeability (i.e. "channel arrest") Regulation of this function is particularly important as it is a major channel for ATP energy and hence a major potential source of hypoxic ATP conservation. In other instances, down-regulation may be achieved by directly repressing the expression of a gene or genes which contribute to that function. For example, gluconeogenesis may be inhibited by repressing expression of phospboenolpyruvate carboxykinase, a key regulator of carbon flow into gluconeogenesis. Accordingly, the invention makes use of anti-sense transgenes which prevent expression of such gluconeogenic enzymatic activities.

The invention further contemplates the use of specific inhibitors of these and other ATP "energy turnover" functions as well as other functions to be down-regulated within the method of the present invention. For example, many biosynthetic enzymes function as multimeric complexes and so dominant negative mutant versions of these genes, such as truncations which retain subunit association activity but have lost catalytic function, may be readily obtained. These mutant proteins interfere with function of the endogenous protein by a process known as "subunit poisoning." When linked to an inducible promoter such mutant proteins allow for inducible repression of key control-point "energy turnover" biosynthetic processes such as gluconeogenesis and the Krebs citic acid cycle.

4.6. Plant Vectors and Transgene Expression

The invention generally provides a variety of methods and reagents for the expression of transgenes from vectors which facilitate transmission of the heterologous transgene and which may further provide other functional elements, such as plant transcriptional promoters, plant transcriptional terminators, plant replication elements, or plant selectable marker genes as described further below.

The invention provides for the expression of a heterologous gene conferring a desired trait of *Zostera marina* by incorporating the heterologous gene into a suitable vector which facilitates DNA transfer into and expression within the target plant host. The amount of DNA transferred is typically 10 kb or less, but can be larger in some instances. The manner in which the transgene is expressed can be controlled by the use of appropriate cis-regulatory sequences in the plant vector. In particular, promoters can be selected that either allow constitutive gene expression or limit gene expression to only specific plant cell types or in response to specific environmental stimuli. Furthermore, the translational fusion of specific signal sequences to the peptide coding region can target expression to particular subcellular or extracellular locations.

4.6.1. Expression Constructs

In accordance to the present invention, a plant with ectopic overexpression of an anti-fouling, hypoxia/anoxia-resistance or salt-resistance promoting activity may be engineered by transforming a plant cell with a gene construct comprising a plant promoter operably associated with a sequence encoding the desired enzyme or other bioactivity. (Operably associated is used herein to mean that transcription controlled by the "associated" promoter would produce a functional messenger RNA, whose translation would produce the enzyme.) In a preferred embodiment of the present invention, the associated promoter is a strong and non tissue- or developmental-specific plant promoter (e.g. a promoter that strongly expresses in many or all tissue types). Examples of such strong, "constitutive" promoters include, but are not limited to, the CaMV 35S promoter, the T-DNA mannopine synthetase promoter, and their various derivatives.

In another embodiment of the present invention, it may be advantageous to engineer a plant with a gene construct operably associating a tissue- or developmental-specific promoter with a sequence encoding the desired enzyme. For example, where expression in photosynthetic tissues and organs are desired, promoters such as those of the ribulose bisphosphate carboxylase (RUBISCO) genes or chlorophyll a/b binding protein (CAB) genes may be used; where expression in seed is desired, promoters such as those of the various seed storage protein genes may be used; where expression in nitrogen fixing nodules is desired, promoters such those of the legehemoglobin or nodulin genes may be used; where root specific expression is desired, promoters such as those encoding for root-specific glutamine synthetase genes may be used (see Tingey et al., 1987, EMBO J. 6:1–9; Edwards et al., 1990, Proc. Nat. Acad. Sci. USA 87:3459–3463).

In an additional embodiment of the present invention, it may be advantageous to transform a plant with a gene construct operably associating an inducible promoter with a sequence encoding the desired enzyme. Examples of such promoters are many and varied. They include, but are not limited to, those of the heat shock genes, the defense responsive gene (e.g., phenylalanine ammonia lyase genes), wound induced genes (e.g., hydroxyproline rich cell wall protein genes), chemically-inducible genes (e.g., nitrate reductase genes, gluconase genes, chitinase genes, etc.), dark-inducible genes (e.g., asparagine synthetase gene (Coruzzi and Tsai, U.S. Pat. No. 5,256,558, Oct. 26, 1993, Gene Encoding Plant Asparagine Synthetase) for example.

Particularly preferred promoters are those which provide expression which is responsive to an environmental signal—e.g. an environmental condition such as exposure to a pathogen, soil salinity or root hypoxia. In particular, the promoter may be selected so as to confer expression of the heterologous transgene in response to an otherwise deleterious environmental condition which the heterologous expression unit is designed to mitigate. For example, in addition to the aforementioned phenylalanine ammonia lyase gene promoter, suitable pathogen-inducible promoters for use with the invention include: the tobacco hsr 203J gene promoter (see e.g. Keller et al. (1999) Plant Cell 11; 223–35); the *Arabiposis* pathogenesis-related protein PR-1 gene promoters (see e.g. Lebel et. al. (1998) Plant J 16: 223–33); the *Arabiposis* Thi2.1 thionin gene promoter (see e.g Bohlmann et al. (1998) FEBS Lett 437: 281-6); the tobacco sesquiterpene cyclase gene promoter (see e.g. Yin et al. (1997) Plant Physiol 115: 437–51); and the tobacco virus-inducible myb gene promoter (see e.g. Yang & Klessig (1996) Proc Natl Acad Sci USA 93: 14972–7). In addition, constitutively active plant avirulence gene promoters such as the avrRxv gene (see e.g. Ciesiolka et al. (1999) Mol Plant Microbe Interact 12: 35–44) may be adapted for expression of the subject heterologous genetic traits. Available hypoxia/anoxia-inducible promoters include: the maize glyceraldehyde-3-phosphate dehydrogenase gpc3 and gpc4 gene promoters (see e.g Manjunath & Sachs (1997) Plant Mol Biol 33: 97–112); the maize Adh1 gene promoter (see e.g Kyozuka et al. (1994) Plant Cell 6: 799–810; Olive et al. (1991) Nucleic Acids Res 19: 7053–60); the *Pisum sativum* Adh gene promoter (see e.g J Mol Biol 195: 115–23); the Arabidopsis Adh gene promoter (see e.g. Chung & Ferl (1999) Plant Physiol 121: 429–36); and the 1-aminocyclopropane-1-carboxylate synthase gene promoter (see e.g Olson (1995) J Biol Chem 270: 14056–61). Available salt-inducible promoters for use with the invention include- the alfalfa MsPRP2 gene promoter (see e.g Bastola et al. (1998) Plant Mol Biol 38: 1123–35); the potato ci7 gene promoter (see e.g Kirch et al. (1997) Plant Mol Biol 33: 897–909), the *Arabidopsis* RD19 and RD21 gene promoters (see e.g. Koizumi (1993) Gene 129: 175–82); and the maize rab28 gene promoter (see e.g. Pla et al. (1993) Plant Mol Biol 21: 259–66).

In yet another embodiment of the present invention, it may be advantageous to transform a plant with a gene construct operably linking a modified or artificial promoter to a sequence encoding the desired enzyme. Typically, such promoters, constructed by recombining structural elements of different promoters, have unique expression patterns and/or levels not found in natural promoters. See erg., Salina et al., 1992, Plant Cell 4:1485–1493, for examples of artificial promoters constructed from combining cis-regulatory elements with a promoter core.

The invention further provides for the ectopic overexpression of a sulfotransferase or other *Zostera marina* genetic trait-conferring activity. Ectopic overexpression of the subject *Zostera* activity may be engineered by increasing the copy number of the gene encoding the desired enzyme. One approach to producing a plant cell with increased copies of the desired gene is to transform with nucleic acid constructs that contain multiple copies of the gene. Alternatively, a gene encoding the desired enzyme can be placed in a nucleic acid construct containing an amplification-selectable marker (ASM) gene such as the glutamine synthetase or dihydrofolate reductase gene. Cells transformed with such constructs is subjected to culturing regimes that select cell lines with increased copies of ASM gene. See Donn et al., 1984, J. Mol. Appl. Genet. 2:549–562, for a selection protocol used to isolate of a plant cell line containing amplified copies of the GS gene. Because the desired gene is closely linked to the ASM gene, cell lines that amplified the ASM gene would also likely to have amplified the gene encoding the desired enzyme.

In another embodiment of the present invention, the ectopic overexpression of a sulfotransferase or other heterologous gene may be engineered by transforming a plant cell with a nucleic acid construct encoding a regulatory gene that controls the expression of the endogenous gene or an transgene encoding the desired enzyme, wherein the introduced regulatory gene is modified to allow for strong expression of the enzyme in the desired tissues and/or developmental stages. synthetase promoter, and their various derivatives.

4.6.2. Suppression Constructs

In accordance to the present invention, a desired plant may be engineered by suppressing certain bioactivities which promote sensitivity to anoxia/hypoxia or high salt conditions. For example, as described herein, salt tolerance may be promoted in a target host plant by the introduction of suppression construct which interferes with expression of one or more MIP aquaporin-encoding genes in a salt-inducible manner. Similarly, anoxia/hypoxia-resistance may be promoted by suppressing gluconogenesis, such as by suppressing the synthesis of phosphoenolpyruvate carboxykinase. The suppression may be engineered by transforming a plant cell with a gene construct encoding an antisense RNA complementary to a segment or the whole of a host target RNA transcript, including the mature target mRNA. In another embodiment, target (e.g., the endogenous MIP-encoding mRNA) suppression may be engineered by transforming a plant cell with a gene construct encoding a ribozyme that cleaves a host target RNA transcript, (e.g., GS RNA transcript, including the mature GS mRNA).

In yet another embodiment, target gene suppression may be engineered by transforming a plant cell with a gene construct encoding the target enzyme containing a "dominant negative" mutation. Preferred mutations are those affecting catalysis, substrate binding (e.g., for phosphoenolpyruvate carboxykinase), or product release. A useful mutation may be a deletion or point-mutation of the critical residue(s) involved with the above-mentioned processes. An artisan can refer to teachings herein and of Herskowitz (Nature, 329:219–222, 1987) for approaches and strategies to constructing dominant negative mutations.

For all of the aforementioned suppression constructs, it is preferred that such gene constructs express with the same tissue and developmental specificity as the target gene. Thus, it is preferred that these suppression constructs be operatively associated with the promoter of the target gene. Alternatively, it may be preferred to have the suppression constructs expressed constitutively. Thus, a strong, constitute promoter, such as the CaMV 35S promoter, may also be used to express the suppression constructs. A most preferred promoter for these suppression constructs is a modified promoter of the target gene, wherein the modification results in enhanced expression of the target gene promoter without changes in the tissue or developmental specificities.

In accordance with the present invention, desired plants with suppressed target gene expression may also be engineered by transforming a plant cell with a co-suppression construct. A co-suppression construct comprises a functional promoter operatively associated with a complete or partial coding sequence of the target gene. It is preferred that the operatively associated promoter be a strong, constitutive promoter, such as the CaMV 35S promoter. Alternatively, the co-suppression construct promoter can be one that expresses with the game tissue and developmental specificity as the target gene. Such alternative promoters could include the promoter of the target gene itself.

According to the present invention, it is preferred that the co-suppression construct encodes a incomplete target mRNA or defective target enzyme, although a construct encoding a fully functional target mRNA or enzyme may also be useful in effecting co-suppression.

In accordance with the present invention, desired plants with suppressed target gene expression may also be engineered by transforming a plant cell with a construct that can effect site-directed mutagenesis of the endogenous target gene. (See Offringa et al., 1990, EMBO J. 9:3077–84; and Kanevskii et al., 1990, Dokl. Akad. Nauk. SSSR 312:1505–1507) for discussions of nucleic constructs for effecting site-directed mutagenesis of target genes in plants.) It is preferred that such constructs effect suppression of target gene by replacing the endogenous target gene sequence through homologous recombination with none or inactive coding sequence.

4.6.3. Nucleic Acids and Proteins

The properties of the nucleic acid sequences of the invention are varied as are the genetic structures of various potential host plant cells. The preferred embodiments of the present invention will describe a number of features which an artisan may recognize as not being absolutely essential, but clearly advantageous. These include methods of isolation, synthesis or construction of gene constructs, the manipulations of the gene constructs to be introduced into plant cells, certain features of the gene constructs, and certain features of the vectors associated with the gene constructs.

Further, the gene constructs of the present invention may be encoded on DNA or RNA molecules. According to the present invention, it is preferred that the desired, stable genotypic change of the target plant be effected through genomic integration of exogenously introduced nucleic acid construct(s), particularly recombinant DNA constructs. Nonetheless, according to the present inventions, such genotypic changes can also be effected by the introduction of episomes (DNA or RNA) that can replicate autonomously and that are somatically and germinally stable. Where the introduced nucleic acid constructs comprise RNA, plant transformation or gene expression from such constructs may proceed through a DNA intermediate produced by reverse transcription.

The nucleic acid constructs described herein can be produced using methods well known to those skilled in the art. Artisans can refer to sources like Sambrook et al., 1989, Molecular Cloning: a laboratory manual, Cold Spring Harbor Laboratory Press, Plainview, N.Y. for teachings of recombinant DNA methods that can be used to isolate, characterize, and manipulate the components of the constructs as well as to built the constructs themselves. In some instances, where the nucleic acid sequence of a desired component is known, it may be advantageous to synthesize it rather than isolating it from a biological source. In such instances, an artisan can refer to teachings of the likes of Caruthers et al., 1980, Nuc. Acids Res. Symp. Ser. 7:215–233, and of Chow and Kempe, 1981, Nuc. Acids Res. 9:2807–2817. In other instances, the desired components may be advantageously produced by polymerase chain reaction (PCR) amplification. For PCR teachings, an artisan can refer to the like of Gelfand, 1989, PCR Technology, Principles and Applications for DNA Amplification, H. A. Erlich, ed., Stockton Press, N.Y., Current Protocols In Molecular Biology, Vol. 2, Ch. 15, Ausubel et al. eds., John Wiley & Sons, 1988.

As described below, one aspect of this invention pertains to an isolated nucleic acid comprising the nucleotide sequence encoding one of the subject heterologous genes, biologically active fragments thereof, and/or equivalents of such nucleic acids. The term "nucleic acid" as used herein is intended to include such fragments and equivalents. Moreover, the term "nucleic acid encoding an heterologous gene" is understood to include nucleotide sequences encoding homologous proteins functionally equivalent to the heterologuous proteins set forth in the sequence listings, or functionally equivalent polypeptides which, for example, retain a desired heterologous gene activity such as an anti-fouling activity, and which may additionally retain other activities of the heterologous protein, e.g., a sulfotransferase activity. In certain embodiments, the present invention contemplates that the subject nucleic acid will encode a heterologous gene from another plant species, such as *Zostera marina* or another species of *Zostera* or another marine vascular plant, e.g. a sulfotransferase gene derived from *Zostera marina* or a related gene from a marine or land plant which will hybridize under stringent conditions to such a sulfotransferase-encoding sequence.

Moreover, it will be understood that such equivalent polypeptides as described above may mimic (agonize) the actions of the authentic form of one of the subject heterologous proteins. However, it is expressly provided that such equivalents will also include polypeptides which antagonize the normal function of the wild-type protein. For instance, dominant negative mutants of the subject proteins may competitively inhibit a biochemical process which is beneficially down-regulated under certain circumstances—e.g., upon exposure to anoxic conditions to promote root survival. Mutants of either of the subject proteins which produce non-productive complexes with other regulatory proteins, e.g., preventing formation of a functional enzymatic complex, can be antagonistic homologs. Accordingly, the term "biological activity", with respect to homologs of the proteins enumerated herein, refers to both agonism and antagonism of the ordinary function of the wild-type form of that protein.

Thus, equivalent nucleotide sequences will include sequences that differ by one or more nucleotide substitutions, additions or deletions, such as intragenus variants; and will also include sequences that differ from the nucleotide sequence encoding the portion of the a protein represented herein due to the degeneracy of the genetic code. Equivalent nucleic acids will also include nucleotide sequences that hybridize under stringent conditions (i.e., equivalent to about 20–27□C. below the melting temperature (Tm) of the DNA duplex formed in about 1 M salt) to a nucleotide sequence of an heterologous gene of the invention.

Preferred nucleic acids encode polypeptides comprising an amino acid sequence which is at least 70% identical, more preferably 80% identical and most preferably 85% identical with an amino acid sequence of the invention. Nucleic acids encoding polypeptides, particularly polypeptides retaining an activity of one of the subject heterologous genes which confer a *Zostera marina* genetic traits, and comprising an amino acid sequence which is at least about 90%, more preferably at least about 95%, and most preferably at least about 98–99% identical with an amino acid sequence of the invention are also within the scope of the invention.

In yet a further embodiment, the recombinant regulatory genes may further include, additional nucleotide sequences. For instance, the recombinant gene can include nucleotide sequences of a PCR fragment generated by amplifying the gene from a genomic DNA library, e.g., 5' and 3' non-coding sequences of either of the subject genes.

Another aspect of the invention provides nucleic acid that hybridizes under high or low stringency conditions to nucleic acid which encodes a polypeptide identical or homologous with an amino acid sequence of the invention. Appropriate stringency conditions which promote DNA hybridization, for example, 6.0 x sodium chloride/sodium citrate (SSC) at about 45□C., followed by a wash of 2.0 x SSC at 50□C., are known to those skilled in the art or can be found in Current Protocols in Molecular Biology, John Wiley & Sons, N.Y. (1989) 6.3.1–6.3.6. For example, the salt concentration in the wash step can be selected from a low stringency of about 2.0×SSC at 50□C. to a high stringency of about 0.2×SSC at 50□C. In addition, the temperature in the wash step can be increased from low stringency conditions at room temperature, about 22□C., to high stringency conditions at about 65□C.

Isolated nucleic acids encoding an heterologous protein of the present invention, yet which differ from the nucleotide sequences referenced herein due to degeneracy in the genetic code, are also within the scope of the invention. Such nucleic acids are understood to be capable of encoding functionally equivalent polypeptides (i.e., a polypeptide having at least a portion of the biological activity of a protein encoded by the enumerated sequences). For instance, a number of amino acids are designated by more than one triplet. Codons that specify the same amino acid (for example, CAU and CAC are synonyms for histidine) may result in "silent" mutations which do not affect the amino acid sequence of the protein. However, it is expected that DNA sequence polymorphisms that do lead to changes in the amino acid sequences of the protein will exist even within the same species. One skilled in the art will appreciate that these variations in one or more nucleotides (up to about 3–4% of the nucleotides) of a gene encoding a protein may exist among individual cells of a given species, e.g., amongst a population of *C. albicans* cells, due to natural allelic variation. Any and all such nucleotide variations and resulting amino acid polymorphisms are within the scope of this invention.

Fragments of the nucleic acid encoding portions of the subject heterologous proteins, such as a fragments which retain the ability to interact with other components of a biochemical pathway, such a; the Krebs' citric acid cycle or an endogeneous sulfotransferase or other protein, are also within the scope of the invention. As used herein, such fragments refer to nucleotide sequences having fewer nucleotides than the coding sequence of the gene, yet still include enough of the coding sequence so as to encode a polypeptide with at least some of the activity of the full-length protein activity.

Nucleic acids within the scope of the invention may also contain linker sequences, modified restriction endonuclease sites and other sequences useful for molecular cloning, expression or purification of the recombinant polypeptides.

As indicated by the examples set out below, a nucleic acid encoding one of the subject proteins may be obtained from mRNA present in a sample of eukaryotic cells, such as those of a marine vascular plant from the genus *Zostera*. It will also be possible to obtain nucleic acids encoding the subject proteins from genomic DNA obtained from such cells. For example, a gene encoding one of the subject sulfotransferase proteins can be cloned from either a cDNA or a genomic library from other *Zostera* species in accordance with protocols described herein, as well as those generally known in the art. For instance, a cDNA encoding an heterologous protein can be obtained by isolating total mRNA from a *Zostera* plant, generating double stranded cDNAs from the total mRNA, cloning the cDNA into a suitable plasmid or bacteriophage vector, and isolating clones expressing the subject protein using any one of a number of known techniques, e.g., oligonucleotide probes, western blot analysis, or complementation. Genes encoding related proteins can also be cloned using established polymerase chain reaction techniques in accordance with the nucleotide sequence information provided by the invention. The nucleic acid of the invention can be DNA or RNA.

Another aspect of the invention relates to the use of the isolated nucleic acid in "antisense" strategy. As used herein, "antisense" refers to delivery or in situ generation of oligonucleotides or nucleic acids or their derivative; which specifically hybridizes (e.g. binds) under cellular conditions, with the cellular mRNA and/or genomic DNA encoding an endogenous target plant activity to be repressed, e.g. a plant gene which promotes plant gluconeogenesis under anaerobic conditions. The "antisense" nucleic acid represses the endogenous plant gene by, for example, inhibiting transcription and/or translation. The binding may be by conventional base pair complementarity, or, for example, in the case of binding to DNA duplexes, through specific interactions in the major groove of the double helix. In general, "antisense" repression refers to the range of techniques generally employed in the art, and includes any therapy which relies on specific binding to nucleic acid sequences.

An antisense construct of the present invention can be delivered, for example, as an expression plasmid which, when transcribed in the cell, produces RNA which is complementary to at least a unique portion of the cellular mRNA which encodes one of the regulatory proteins. Alternatively, the antisense construct is an oligonucleotide probe which is generated ex vivo and which, when introduced into the cell, causes inhibition of expression by hybridizing with the complementary mRNA and/or genomic sequences. In any event, it will be generally desirable to choose an antisense molecule which uniquely hybridizes to the target plant gene, e.g. does not hybridize under physiological conditions to DNA or RNA from an unrelated plant or animal cell, especially a human cell. Such oligonucleotide probes are preferably modified oligonucleotides which are resistant to endogenous nucleases, e.g. exonucleases and/or endonucleases, and is therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775, as well as the peptide nucleic acids known in the art). Additionally, general approaches to constructing oligomers useful in antisense therapy have been reviewed, for example, by van der Krol et al. (1988) Biotechniques 6:958–976; and Stein et al. (1988) Cancer Res 48:2659–2668.

Accordingly, the modified oligomers of the invention are useful in therapeutic, diagnostic, and research contexts. In therapeutic applications, the oligomers are utilized in a manner appropriate for antisense therapy in general. For such therapy, the oligomers of the invention can be formulated for a variety of modes of administration, including systemic and topical or other localized administration. Techniques and formulations generally may be found in Remmington's Pharmaceutical Sciences, Meade Publishing Co., Easton, Pa.

Moreover, the nucleotide sequence determined from the cloning of the subject heterologous genes will permit the generation of probes designed for use in identifying the heterologous transgenic DNA as well as for detecting the presence of the corresponding heterologous mRNA. For example, the subject nucleic acids may be used following transgenic targeting to confirm the presence and integrity of the introduced sequence as well as the amount and specificity of expression in transgenic progeny. For instance, the present invention provides a probe/primer comprising a substantially purified oligonucleotide, wherein the oligonucleotide comprises a region of nucleotide sequence which hybridizes under stringent conditions to at least 10, more preferably 25, 50, or 100 consecutive nucleotides of sense or anti-sense sequence of one of the subject nucleic acids, or naturally occurring mutants thereof. In preferred embodiments, the probe/primer further comprises a label group attached thereto and able to be detected, e.g. the label group is selected from the group consisting of radioisotopes, fluorescent compounds, enzymes, and enzyme co-factors.

This invention also provides expression vectors which include a nucleotide sequence encoding one of the subject polypeptides and operably linked to at least one regulatory sequence. Operably linked is intended to mean that the nucleotide sequence is linked to a regulatory sequence in a manner which allows expression of the nucleotide sequence. Plant egulatory sequences are art-recognized. Accordingly, the term regulatory sequence includes promoters, enhancers and other expression control elements. Exemplary plant regulatory sequences are described in Yusibo et al. (1999) Curr Top Micro & Immun 240: 81–94 and Hood et al. (1999) Adv Exp Med & Biol 464: 127–47. For instance, any of a wide variety of expression control sequences-sequences that control the expression of a DNA sequence when operatively linked to it may be used in these vectors to express DNA sequences encoding the *Zostera* genetic trait-conferring proteins and nucleic acids of this invention. Such useful expression control sequences, include, for example, the constitutive maize ubiquitin promoter (ubi promoter) (Christensen et al. (1992) Plant Mol Biol 18: 675–89; Cornejo et al. (1993) Plant Mol Biol 23: 567–81) and the potato PinII terminator sequence (An et al. (1989) Plant Cell 1: 115–22). Other useful expression control sequences are those derived from plant viruses such as: the 35S promoter, which is derived from Cauliflower Mosaic Virus sequences; and the TMV coat protein promoter, such as that contained in the cloning vector designated "30B" which is derived from the Tobacco Mosaic Virus. Also included in certain aspects of the invention are non-plant transcriptional regulatory sequences such as early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast a-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other proteins encoded by the vector, such as antibiotic markers, should also be considered.

The recombinant construct of the present invention may include a selectable marker for propagation of the construct. For example, a construct to be propagated in bacteria preferably contains an antibiotic resistance gene, such as one that confers resistance to kanamycin, tetracycline, streptomycin, or chloramphenicol. Suitable vectors for propagating the construct include plasmids, cosmids, bacteriophages or viruses, to name but a few.

In addition, the recombinant constructs may include plant-expressible selectable or screenable marker genes for isolating, identifying or tracking of plant cells transformed by these constructs. Selectable markers include, but are not limited to, genes that confer antibiotic resistances (e.g., resistance to kanamycin or hygromycin) or herbicide resistance (e.g., resistance to sulfonylurea, phosphinothricin, or glyphosate). Screenable markers include, but are not limited to, the genes encoding beta-glucuronidase (Jefferson, 1987, Plant Molec Biol. Rep 5:387–405), luciferase (Ow et al., 1986, Science 234:856–859), B and C1 gene products that regulate anthocyanin pigment production (Goff et al., 1990, EMBO J 9:2517–2522).

In embodiment; of the present invention which utilize the Agrobacterium system for transforming plants (see infra), the recombinant DNA constructs additionally comprise at least the right T-DNA border sequence flanking the DNA sequences to be transformed into plant cell. In preferred embodiments, the sequences to be transferred in flanked by the right and left T-DNA border sequences. The proper design and construction of such T-DNA based transformation vectors are well known to those skilled in the art.

This invention also pertains to a host cell transfected with a recombinant gene in order that it may express a recombinant protein of the present invention. The host cell may be any prokaryotic or eukaryotic cell. For example, a plant sulfotransferase protein of the present invention may be expressed in bacterial cells, such as E. coli, insect cells, yeast, or mammalian cells. Other suitable host cells are known to those skilled in the art.

Another aspect of the present invention concerns recombinant forms of the subject plant proteins. The term "recombinant protein" refers to a protein of the present invention which is produced by recombinant DNA techniques, wherein generally DNA encoding the protein is inserted into a suitable expression vector which is in turn used to transform a host cell to produce the heterologous protein. Moreover, the phrase "derived from", with respect to a recombinant gene encoding one of the subject proteins, is meant to include within the meaning of "recombinant protein" those proteins having an amino acid sequence of the native (or "authentic") form of the plant protein, or an amino acid sequence similar thereto, which is generated by mutation so as to include substitutions and/or deletions relative to a naturally occurring form of the protein. To illustrate, recombinant proteins preferred by the present invention, in addition to those having an amino acid sequence of the native proteins, are those recombinant proteins having amino acid sequences which are at least 70% homologous, more preferably 80% homologous and most preferably 90% homologous with an ammo acid sequence of the present invention A polypeptide which having an amino acid sequence that is at least about 95%, more preferably at least about 98%, and most preferably identical to one of the polypeptide sequences of the invention are also within the scope of the invention. Thus, the present invention pertains to recombinant proteins which are derived, for example from *Zostera marina* genes and which have amino acid sequences evolutionarily related to a sequence encoded by an orthologous gene from another plant protein, wherein "evolutionarily related to" refers to polypeptides having amino acid sequences which have arisen naturally (e.g. by allelic variance), as well as mutational variants of the regulatory proteins which are derived, for example, by combinatorial mutagenesis.

The present invention further pertains to methods of producing the subject polypeptides. For example, a host cell transfected with a nucleic acid vector directing expression of a nucleotide sequence encoding one of the subject proteins can be cultured under appropriate conditions to allow expression of the polypeptide to occur. The polypeptide may be secreted and isolated from a mixture of cells and medium containing the recombinant protein, e.g., by including a secretion signal sequence fused in frame to a *Zostera marina* protein. Alternatively, the polypeptide may be retained cytoplasmically and the cells harvested, lysed and the protein isolated. A "cell culture" includes host cells, media and other byproducts. Suitable media for cell culture are well known in the art. The polypeptide can be isolated from cell culture medium, host cells, or both using techniques known in the art for purifying proteins including ion-exchange chromatography, gel filtration chromatography, ultrafiltration, electrophoresis, and/or immunoaffinity purification. In a preferred embodiment, the protein is a fusion protein containing a domain which facilitates its purification, such as a GST or poly-histidine fusion protein.

Thus, a nucleotide sequence derived from the cloning of one of the subject proteins, encoding all or a selected portion of the protein, can be used to produce a recombinant form of the protein via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known intracellular proteins. Similar procedures, or modifications thereof, can be employed to prepare recombinant forms of the subject proteins, or portions thereof, by microbial means or tissue-culture technology in accord with the subject invention. Exemplary expression vectors are described above.

The coding sequences for the subject polypeptides can be incorporated as a part of fusion genes so as to be covalently linked in-frame with a second nucleotide sequence encoding a different polypeptide. This type of expression system can be useful, for instance, where it is desirable to produce an immunogenic fragment of the protein. For example, the VP6 capsid protein of rotavirus can be used as an immunologic carrier protein for portions of the subject polypeptides, either in the monomeric form or in the form of a viral particle. The nucleic acid sequences corresponding to the portion of the protein to which antibodies are to be raised can be incorporated into a fusion gene construct which includes coding sequences for a late vaccinia virus structural protein to produce a set of recombinant viruses expressing fusion proteins comprising a portion of the protein as part of the virion.

In addition to utilizing fusion proteins to enhance immunogenicity, it is widely appreciated that fusion proteins can also facilitate the expression of proteins, for example, recombinant forms of each of the subject pathogen proteins can be generated as glutathione-S-transferase (CST) fusion proteins. Such CST fusion proteins can be used to simplify purification of the protein, such as through the use of glutathione-derivatized matrices (see, for example, Current Protocols in Molecular Biology, Ausabel et al., Eds. John Wiley & Sons, N.Y., 1991). In another embodiment, a fusion gene coding for a purification leader sequence, such as a poly-(His)/enterokinase cleavage site sequence at the N-terminus of the desired portion of the recombinant protein, can facilitate purification of the fusion protein by affinity chromatography using a Ni2+ metal resin. The purification leader sequence can then be subsequently removed by treatment with enterokinase (e.g., see Hochuli et al. (1987) J. Chromatography 411:177; and Janknecht et al. PNAS 88:8972).

Techniques for making fission genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, Current Protocols in Molecular Biology, eds. Ausabel et al. John Wiley & Sons. 1992).

The invention further provides methods for the modification of a transgene to facilitate expression in the host plant. For example, the transgene can be modified by site-directed mutagenesis to reflect preferred codon usage in the host plant. This technique have been used effectively to maximize expression of the avidin gene in maize (Hood et al. (1997) Mol Breeding 3: 291–306).

Another example of transgene modification for optimization of expression in tie host plant is the insertion of an endoplamic reticulum retention sequence which prevents the transgeneic gene polypeptide product from being modified by glycosylation in the golgi apparatus. For example, some proteins are retained in the endoplasmic reticulum simply by inserting the sequence KDEL or HDEL into the transgenic polypeptide (Pelham (1990) Trends Biochem Sci 15: 483–86). Accordingly, the invention provides for the modification of the heterologous transgene by insertion of an appropriate nucleic acid sequence encoding an endoplasmic reticulum retention signal in instances in which it is desirable to avoid the glycosylation or secretion of the transgenic polypeptide. Alternatively, mutant host plants can be generated which are defective in one or more of the golgi enzymes involved in the modification of N-linked glycans, such as those involved in the addition of sialic acid side chains (see e.g. Von Schaewen et al. (1993) Plant Physiol 102: 1109–18).

The present invention also makes available purified, or otherwise isolated forms of the subject proteins, which are isolated from, or otherwise substantially free of, other intracellular proteins which may be normally associated. The term "substantially free of other cellular proteins" (also referred to herein as "contaminating proteins") is defined as encompassing, for example, protein preparations comprising less than 20% (by dry weight) contaminating protein, and preferably comprises less than 5% contaminating protein. Purified forms of the subject polypeptides can be prepared as purified preparations, for example, by using the cloned genes as described herein. The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions. The isolated protein can include, for example, nucleosides, metals, or other non-protein co-factors required for biological activity.

Another aspect of the present invention pertains to isolated/purified complexes of proteins including the subject proteins. As set out in more detail herein, the subject proteins are understood to participate in oligomeric complexes. For instance, the present invention contemplates purified protein complexes including, e.g., one of the subject target plant biosynthetic enzymes, or an appropriate fragment thereof, and one or more other plant biosynthetic enzymes from the game pathway and/or with which the subject enzyme associates (e.g. glycolytic pathway complexes).

Another aspect of the invention related to polypeptides derived from the full-length forms of the subject proteins, Isolated peptidyl portions can be obtained by screening polypeptides recombinantly produced from the corresponding fragment of the nucleic acid encoding such polypeptides. In addition, fragments can be chemically synthesized using techniques known in the art such as conventional Merrifield solid phase f-Moc or t-Boc chemistry. For example, CaSPT3 can be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of, for example, an anti-fouling activity. An exemplary technique for refining binding domains in protein fragments is described by Román et al. (1994) Eur J Biochem 222;65–73. Román et al. describe the use of competitive-binding assays using short, overlapping synthetic peptides from larger proteins; e.g., the technique of Román et al. can be applied to identify binding domains of the subject target plant proteins.

Moreover, there are several forms of mutagenesis generally applicable, in addition to a general combinatorial mutagenesis approach. For example, homologs of the subject proteins (both agonist and antagonist forms) can be generated and screened using, for example, alanine scanning mutagenesis and the like (Ruf et al. (1994) Biochemistry 33;1565–1572; Wang et al. (1994) J Biol Chem 269:3095–3099; Balint et al. (1993) Gene 137:109–118; Grodberg et al. (1993) Eur J Biochem 218:597–601; Nagashima et al. (1993) J Biol Chem 268:2988–2892; Lowman et al. (1991) Biochemistry 30:10832–10838; and Cunningham et al. (1989) Science 244:1081–1085), by linker scanning mutagenesis (Gustin et al. (1993) Virology 193:653–660; Brown et al. (1992) Mol Cell Biol 12:2644–2652; McKnight et al. (1982) Science 232:316); or by saturation mutagenesis (Meyers et al. (1986) Science 232:613). Such techniques will be generally understood to provides for reduction of the subject proteins to generate mimetics, e.g. peptide or non-peptide agents, which are able to disrupt binding of a naturally-occurring form of a protein of the present invention with other proteins in order to provide the *Zostera marina* genetic traits which are a subject of the invention (e.g. antagonists of gluconeogenesis induced by anaerobiosis).

Thus, such mutagenic techniques as described above are particularly useful to map the determinants of the subject proteins which participate in protein-protein interactions. To illustrate, the critical residues of a target plant enzyme which is to be inhibited to promote, for example, anaerobic survival, can be determined and used to generate peptidomimetics which competitively inhibit binding of the native target plant enzyme (see, for example, "Peptide inhibitors of human papillomavirus protein binding to retinoblastoma gene protein" European patent applications EP-412,762A and EP-B31,080A). By employing, for example, scanning mutagenesis to map the amino acid residues of a target plant enzyme involved in binding or other activity, peptidomimetic compounds (e.g. diazepine or isoquinoline derivatives) can be generated which mimic those residues, and which therefore can inhibit binding of the authentic plant enzyme. For instance, non-hydrolyzable peptide analogs of such residues can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffinan et al. in Peptides: Chemistry and Biology, G. R. Marshall ed., ESCOM Publisher: Leiden, Netherlands, 1988), substituted g-lactam rings (Garvey et al. in Peptides: Chemistry and Biology, G. R. Marshall ed., ESCOM Publisher: Leiden, Netherlands, 1988), keto-methylene pseudopeptides (Ewenson et al. (1996) J Med Chem 29,295: and Ewenson et al. in Peptides: Structure and Function (Proceedings of the 9th American Peptide Symposium) Pierce Chemical Co. Rockland, Ill., 1985), beta-turn dipeptide cores (Nagai et al. (1985) Tetrahedron Lett 26:647; and Sato et al. (1986) J Chem Soc Perkin Trans 1: 1231), and b-aminoalcohols (Gordon et al. (1985) Biochem Biophys Res Commun 126:419; and Dann et al. (1986) Biochem Biophys Res Commun 134:71). In similar fashion, mimetics can be designed which agonize or antagonize the subject SPT3 proteins.

Another aspect of the invention pertains to antibodies and antibody preparations specifically reactive with at least one of the subject proteins. For example, by using peptides based on the cDNA sequence of one of the proteins of the invention, anti-protein/anti-peptide antisera or monoclonal antibodies can be made using standard methods. A mammal such as a mouse, a hamster or rabbit, can be immunized with an immunogenic form of the peptide. Techniques for conferring immunogenicity on a protein or peptide include conjugation to carriers or other techniques well known in the art. An immunogenic form of the protein can be administered in the presence of adjuvant. The progress of immunization can be monitored by detection of antibody titers in plasma or serum. Standard ELISA or other immunoassays can be used with the immunogen as antigen to assess the levels of antibodies.

In other embodiments, the antibodies are isolated from synthetic antibody libraries, such as antibody phage display libraries. The antibody can be a light chain, a heavy chain, a heavy chain-light chain pair, a single chain antibody, or CDR-containing fragments thereof.

In a preferred embodiment, the subject antibodies are immunospecific for antigenic determinants of one of the proteins of the present invention. In yet a further preferred embodiment of the present invention, antibodies do not substantially cross react (i.e. do not react specifically) with a protein which is: e.g., less than 90 percent homologous, more preferably less than 95 percent homologous, and most preferably less than 98–99 percent homologous with one of the subject proteins. By "not substantially cross react", it is meant that the antibody has a binding affinity for a nonhomologous protein, particularly orthologous proteins from mammalian cells, which is at least one order of magnitude, more preferably at least two orders of magnitude, and even more preferably at least three orders of magnitude less than the binding affinity of that antibody for one of the proteins of the invention.

4.7. Plant Transformation

The invention provides methods for the transformation of plants with an heterologous gene or genes which contribute to the antifouling, salt resistance, anoxia resistance or other genetic traits of *Zostera marina*. In preferred embodiments, the heterologous gene is introduced by transformation, and the introduced gene is expressed stably over the life of the plant and is further capable of being transmitted to the plant's offspring. In general, it is desirable for the transgene to be integrated into the nuclear DNA, although the plastid genome may be an appropriate target for some constructs.

The transformation of crop and other plants can be effected by a number of methods known in the field of plant biotechnology. The preferred method for transformation will vary with the plant species to be transformed and the desired pattern and stability of transgene expression. For example, particle bombardment methods have been shown to be effective in transforming many plant species, including those previously considered recalcitrant to transformation. This method is commonly used in the transformation of monocotyledonous plants such as corn. Another plant transformation method available is Agrobacterium-mediated gene transfer, which is commonly used to transform dicotyledonous crops.

Still other methods available for plant transformation do not rely upon tissue culture for the recovery of transgenic plants, thereby allowing the production of transgenics from plant species for which no reliable method of tissue culture exists. For example, microtargeting of particle-bound DNA into shoot meristematic tissue produces transgenic flowering parts from which transgenic seeds arise (Sautter et al. (1991) Biotechnology 9: 1080–85). Transgenic seeds can also be created by electrophoresing DNA into meristematic tissue (Griesbach (1994) Plant Sci 102: 81–89; Burchi et al. (1995) J Genet Breeding 49: 163–8). This method has proven successful in the transformation of several plant species including *orchids, chrysantehemums, carnations, lisianthus, peppers*, and even woody plant species such as *plum* (*Plumus domestica*).

In general, the invention provides methods and reagents for the genetic engineering of a target host plant, such as a crop plant, with an heterologous nucleic acid which provides one or more of the *Zostera marina* genetic traits of the invention. A preferred method for transformation makes use of the aforementioned common soil bacterium Agrobacterium (see Birch (1997) Ann Rev Plant Physiol Plant Mol Biol 48: 297–326). This method involves a modified transfer-DNA (T-DNA) vector which carries the desired nucleic acid fragment between the T-DNA border regions (specific 25 base pair direct repeat regions). The resulting vector is transferred into an Agrobacterium host and the target host plant is inoculated with the transformed recombinant bacterium. Virulence genes products of Agrobacterium then actively recognize, excise, transport, and integrate the T-DNA region into the host plant genome.

*Agrobacterium tumefaciens*-mediated transformation techniques, including disarming and use of binary vectors, are well described in the scientific literature (see, e.g. Horsch, et al. (1984) Science 233:496–8, and Fraley, et al. (1983) Proc. Nat'l. Acad. Sci. USA 80:4803. Agrobacterium-mediated transformation is a preferred method of transformation of dicots.

The natural host range of Agrobacterium is limited and so this approach to transformation is not practicable in some target host plants, particularly cereal crops and other monocotyledonous species. For such crops, the invention provides alternative approaches to transformation such as direct uptake of naked DNA into protoplasts or tissues using electroporation or particle gun bombardment. In this method, the co-transformation of a selectable marker gene along with the gene of interest allows the preferential growth of the transformed cells in cell culture. Successive manipulations of the chemical composition of the culture medium, especially the plant hormones, allows the regeneration of complete plants. This method has allowed the recovery of genetically engineered plants in virtually all crop plants.

One method for direct transformation of the transgene construct is by particle bombardment of target plant tissues with high-velocity microprojectiles (see e.g. Finer et al. (1999) Curr Top Micro and Immun 240: 60–80 for review). This method utilizes a particle accelerator or "gene blaster" to penetrate the outer surface layers of the plant tissue or protoplast (Sanford (1988) Trends Biotechnol 6: 299–302). Biolistics, a combination of "biological" and "ballistics", describes a technique which utilizes instrumentation to accelerate DNA coated microprojectiles into cells, past the cell wall and cell membrane. The microprojectile is generally small enough (0.5–5.0 mm) to enter the plant cell without too much damage, yet large enough to have the mass to penetrate the cell wall and carry an appropriate amount of DNA on its surface into the interior of the plant cell.

A number of different particle gun designs may be used. The basis of all of these designs is to coat the DNA onto small dense particles and accelerate the particles towards a target tissue. The particles usually consist of either gold or tungsten spherical particles which are between 0.5 and 5.0 mm in diameter. Gold particles are chemically inert, generally more uniform in size than tungsten particles and produce no cytootoxic effects. Accordingly, gold particles are generally preferred over tungsten particles. Ideally the particles used for bombardment should have good initial affinity for DNA, yet freely release the DNA once inside the target cell cytoplasm or nucleus.

To prepare DNA-coated microprojectiles, washed gold or tungsten particles are mixed with plasmid DNA. The DNA is bound on the particles using either ethanol or calcium chloride precipitation methods, which are known in the art. Spermidine may be added to the mixture, possibly protecting the DNA from degradation and/or altering its conformation. After precipitation, the particles may be washed, resuspended and either dried or stored on ice as an aqueous suspension until needed.

The particle gun may utilize a macrocarrier, which supports or carries the particles and is accelerated along with the particles towards the target. The macrocarrier is usually retained by a stopping plate or screen before it collides with the target, whereas the particles continue along their course. In most cases, the particles are accelerated under partial vacuum in a vacuum chamber to reduce air drag. Particle penetration is controlled by modifying the intensity of the explosive burst, by changing the distance that the particles must travel to reach the target tissue or by using different sized particles. A commercial hand-held device (the Helios Gene Gun) is available from BioRad Laboratories (Hercules, Calif.). A helium-modified bombardment device, which utilizes continual build-up of helium back-pressure delivered to a calibrated rupture disc which transmits a shock wave to a second disc or macrocarrier that holds the DNA-coated particles, is also available from BioRad (i.e. the PDS-1000/He unit). A high voltage electrical discharge gun which causes rapid vaporization of a water droplet which in turn transmits a shock wave to a mylar sheet coated with DNA-bound particles has also been developed (see McCabe and Christou (1993) Plant Cell Tiss Organ Cult 33: 227–236). Yet another device for particle bombardment is a microtargeting device, which does not utilize a macrocarrier (Sautter et al. (1991) Bio/Technology 9: 1080–5). This device accelerates small amounts of a DNA/particle mixture in a focused stream of high-pressure nitrogen. The DNA is not precipitate on the gold particles, but is delivered as a mixture.

A variety of different plant tissues have been used as targets for particle bombardment-mediated transformation. Selection of the appropriate target tissue is dependent on multiple factors. For rapid gene expression analysis, various plasmid constructs can be introduced into different tissues and transient expression can be quickly analyzed to assess promoter activity without the production of stably transformed plants (see e.g. Iida et al. (1995) Plant Cell Rep 14: 539–44). Almost any tissue can be used for transient expression studies as long as the cell wall is penetrable by the DNA-coated particles. For example, embryogenic plant cell cultures have been used successfully for the production of transformed plants (see e.g. Fromm et al. (1990) Bio/Technology 8: 833–9). Shoot apical meristem transformation results in chimeric plants, where the transformed cells directly give rise to germ-line tissue and the introduced DNA is then passed onto progeny plants. Bombardment of shoot meristematic tissues followed by tissue culture expansion of the transformed cells has been used to produce genetically-transmissible transgenic plant lines (McCable et al. (1988) Bio/Technology 6; 923–6). In addition to embryogenic cultures and shoot tips, other tissues that have been subjected to particle bombardment include leaves (Klein et al. (1988) Proc Natl Acad Sci USA 85: 8502–5), root sections (Seki et al. (1991) Appl Microbiol Biotechnol 36: 228–30), stem sections (Loopstra et al. (1992) Can J For Res 22: 993–6), pollen (Twell et al. (1989) Plant Physiol 91–1270–4), styles (Clark and Sims (1994) Plant Physiol 106: 25–36), cereal aleurone cells (Kim et al. (1992) Mol Gen Genet 232: 383–93) and tassel primordia (Dupeuis and Pace (1993) Plant Cell Rep 12: 607–11). In certain instances, it is preferable that the plant tissue selected for particle bombardment-mediated transformation be relatively new, as long-term cell cultures can result in abnormalities that may compromise the usefulness of the transgenic plant—such as infertility of the subsequent transgenic progeny (see Rhodes et al. (1988) Biotechnology 6: 56–60).

In certain instances, the magnitude of transgene expression varies markedly with the site of insertion and the nature of the inserted sequence(s). For example, while T-DNA mediated transfer typically results in the insertion of a single complete intact DNA fragment at a single locus, direct DNA transfer approaches frequently result in long concatamers of the transferred DNA (see e.g. Czernilofsky et al. (1986)

DNA 5: 473–82). Such multiple tandem insertions are associated with transcriptional "silencing" phenomena in certain instances. Furthermore, the site of insertion within the plant genome frequently affects the strength of expression of the transgene—a phenomenon know as "position effect." Accordingly, the invention provides methods for mitigating interference with the expression of the transgene. For example, position effects can be mitigated by flanking transgenes with specific matrix-associated regions which insulate transcriptional regulation from the effects of surrounding chromatin (see e.g. Mlynarova et al. (1994) Plant Cell 7: 599–609). For example, scaffold attachment regions (SARs, also known as matrix attachment regions or MARs) may be included in the transgene vector construct. Preferably, the SARs are ligated to the flanking regions of the gene of interest. These sequences are known in the art (e.g. a tobacco SAR is described in Breyne et al. (1992) Plant Cell 4: 463–71; and Allen et al. (1996) Plant Cell 8: 899–913). Furthermore, transgene silencing mediated by homology-dependent processes can be avoided by utilizing transgenic plant lines which avoid multiple tandem or inverted repeat insertion patterns, and by limiting homology of the inserted transgene with any corresponding endogenous host gene(s) by engineering conserved codon replacements within the transgene construct where appropriate. When the transgene is inserted as one intact DNA fragment at a single locus, its expression generally behaves in a highly consistent manner. Such transgenic loci exhibit the expected additive gene action both within loci (hemizygous versus homozygous) and between loci (dihybrids between homozygous transgenic individuals). Loss of transgene unction is rare in such transgenic lines (approximately one in ten thousand), which is consistent with the performance of many endogenous plant genes. Optimized transgenic plants of the invention may be obtained by screening candidate plants for persistent expression of the transgene through multiple generations of breeding or rounds of vegetative propogation.

5. EXAMPLES 5.1 Cloning and Activity of Salfotransferase from *Zostera marina*

Figure 1:
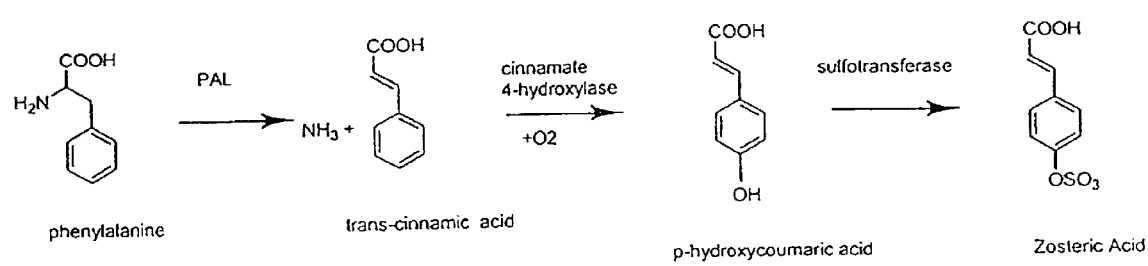
FIG. 1 depicts a pathway for zosteric acid biosynthesis.
Figure 2:
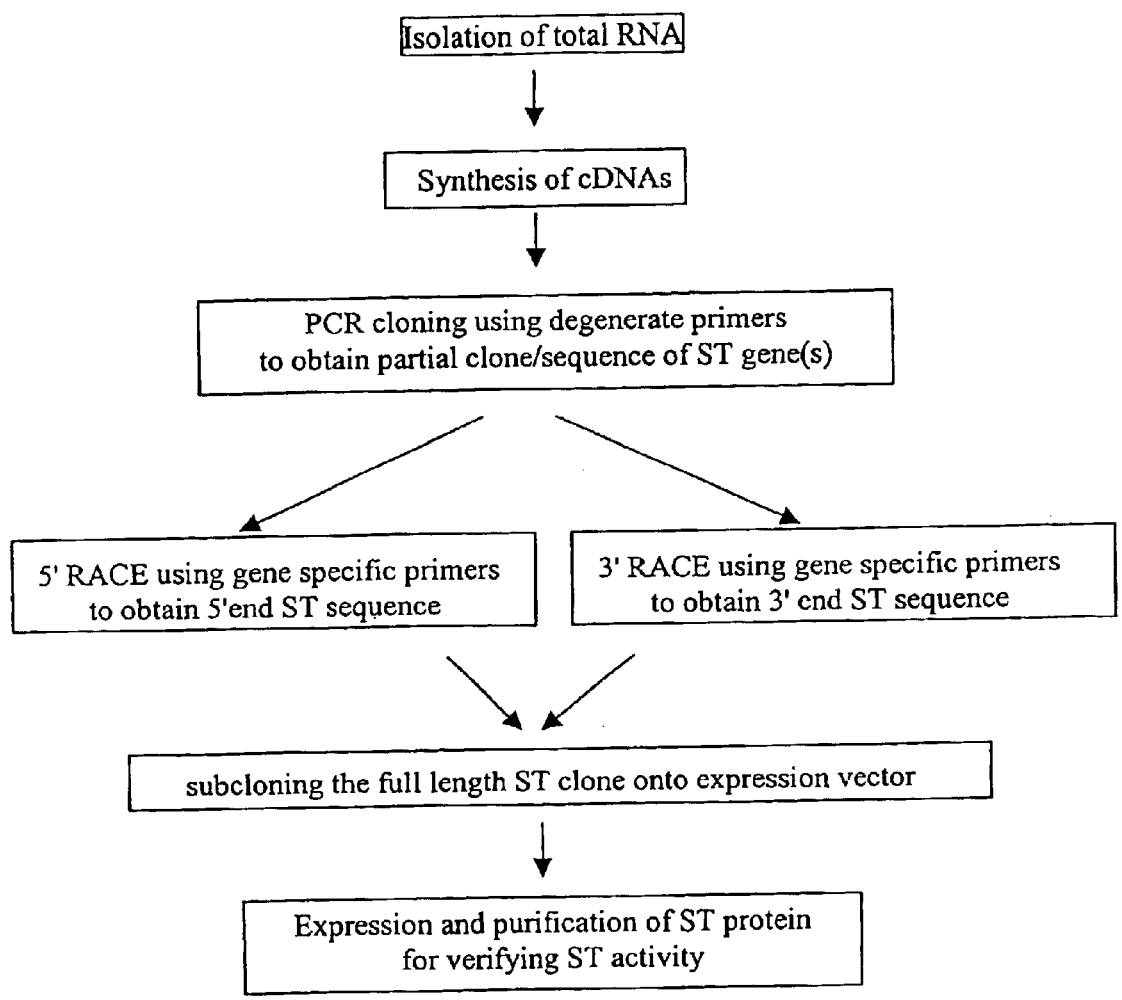
FIG. 2 depicts the basic steps involved in cloning and expressing sulfotransferase (ST) from *Zostera marina*.

A sulfotransferase (ST) was cloned from *Zostera marina* using a PCR-based approach. *Zostera marina* cDNA was obtained from plant tissue using standard methods of plant mRNA isolation and cDNA synthesis (see *Plant Molecular Biology Manual* (1988) Kluwer Academic Press; and *Molecular Cloning: A Laboratory Manual* (1989) Cold Spring Harbor Press). The cloning strategy is illustrated in FIG. 2. Two types of cDNAs were synthesized using total RNA extracted from whole plant tissues of *Z. marina* with OdT primers (single stranded CDNA) or smart II oligos (double stranded cDNA). The single stranded cDNA was used in obtaining partial cDNA ST clones, while the double stranded cDNA was used in 5' and 3' RACE to obtain the remaining sequences at 5' and 3' ends.

In obtaining partial/internal ST sequences, degenerate primers were designed based on the conserved regions of published aryl-STs from vascular plants and human sources. The degenerate and gene-specific primers used for cloning *Zostera marina* sulfotransferase are shown in FIG. 3. Primer pairs of Z-ST-P14 and Z-ST-P16 as well as Z-ST-P14 & Z-ST-P17 yielded a single product of about 850 bp. This PCR product was then cloned into vector pCR2.1 using the TOPO TA cloning Kit from Invitrogen. Restriction mapping of 100 positive colonies randomly picked showed that most were identical clones. Sequence analysis of 8 clones suggest that these clones are partial cDNA ST clones as the sequence exhibited high homology with the flavonol STs from vascular plants as well as the phenol-preferring STs from human. The sequence of these partial clones wag then used to design gene specific primers that were used in 5' and 3' RACE to obtain full-length ST clones and sequence.

3' RACE PCR was performed with primer pairs of Z-ST-P18 and CDSNUP (a mixture of 3' CDS and NUP from CLONTECH), while the 5' RACE was performed using primer Z-ST-P19 and UPM from CLONTECH. A single PCR product was obtained from each of these PCR reaction;, which wag then cloned onto pCR2.1 and sequenced. The results confirm that these PCR products are part of the ST gene, which extended the partial internal ST sequence ca. 290 bp further up the 5' end and ca. 200 bp further down the 3' end with a poly A tail. A detail description of the assembled full sequence is given below.

FIG. 4 illustrates the assembled full-length sequence of the *Z. marina* ST. It contains a 5' region of 48 nucleotides be-fore the first Met codon at 49–51, an open reading frame beginning from nucleotide 49 to the termination codon at 1042–1044 and a 3' untranslated region from nucleotide 1045 to 1075 followed by a poly A tail of ca 20 nucleotides. In the 3' untranslated region, a polyadenylation signal (AATAAA between nucleotide 1055–1060) and a pentamer ATTTA (between nucleotide 1049–1053) known to be involved in MRNA instability are identified. Although there is no hard evidence suggesting that the first 48 nucleotides are 5' untranslated region, the Met codon located at position 49–51 is likely the initiation site for translation as indicated by the alignment of the sequence with known flavonol STs from vascular plants (see FIG. 5).

The alignment of the *Z. marina* ST open reading frame with flavonol STs from *Brassica napus, Arabidopsis thaliana, Flaveria bidentis* and *Homo sapiens* shows that the *Z. marina* ST has a modest level of homology with other aryl-ST (28%, 32%, 31%, 18% identity, respectively) and the homology lies mostly within the 5 conserved blocks. The *Z. marina* ST gene, however, does not contain the motif (KXXXTVXXXE, see dotted nucleotides in FIG. 5) that are important to the dimerization of ST proteins indicating that the *Z. marina* ST protein may function as a monomer (Petrotchenko et al. (2001) FEBS Lett. 490: 39–43).

The first 30 amino acids of the ST protein exhibited the properties of a transmembrane signal (see, e.g. Von Heijne et al. (1989) FEBS Lett 244: 439–46). For instance, it is predicted to form a-helix followed by a very flexible region and it started very hydrophobic and then drastically changed to hydrophilic.

The genomic organization of the ST gene was investigated by PCR with a Z. marina genomic DNA using ST gene specific primers Z-ST-P26 (nucleotide 49 to 72 with an EcoR I site hanging over) and Z-ST-P25 (nucleotide 1133–1156 with an Hind III site hanging over). A stretch of 297 nucleotides that is not seen in the cDNA sequence was obtained (FIG. 6). This fragment of DNA is inserted between nucleotide 258 and 259 on the cDNA sequence, right before the first conserved block (see FIG. 4) and is likely an intron as indicated by 3 lines of evidence. First, It is an AT rich sequence containing many poly T stretches. Secondly, the 5' and 3' sequences of this fragment exhibit high homology to consensus motifs for 5' and 3' intron splice sites in plants (Bredel et al. 1998). In addition, 5 stop codons are located within the sequence.

The full-length ST gene/clones were obtained using the gene specific primers (ZST-P26 and Z-ST-P25) generated according to the far 5' and 3' end sequences (see FIG. 3). The PCR product was then cloned onto expression vector pGEX- 4T-1 at the sites of EcoR I and Sal I. After being sequenced and confirmed to be in frame on the expression vectors, the clone was expressed in BL21 to obtain ST protein, a ST-GST fusion protein of ca. 60 kD, for verifying *Z. marina* ST activity. Trial induction experiments showed that ST-GST protein was expressed in large quantity in BL21. However, these proteins were mostly present in the insoluble inclusion bodies. It was found that lowering temperature to 30° C. and IPTG concentration to 0.1 mM allows for producing significant amount of soluble ST-GST in BL21 cells. Therefore, these conditions were used in the routine preparation for purifying ST-GST fusion protein. The purification of ST-GST was performed using GSH Sepharose™ 4B following the manufacture's instruction. These subcloning, expression and analysis procedures are summarized in FIG. 7.

Enzymatic activity of the purified fusion ST-GST protein was monitored by monitoring the production of products by HPLC along a time course during incubation with the sulfate donor PAPS (3'-phosphate adenosine 5'-phosphosulfate) and a standard phenol substrate, quercetin (see FIGS. 8 and 9). The negative control of GST protein alone did not yield any detectable activity. The quercetin:ST activity was found to be 3 times higher in K-Pi buffer (pH 6.5) than in Tris-HCl (pH 8.0) and was not affected by the high level of GSH presented in the enzyme eluate. The best specific quercetin:ST activity obtained was between 60–100 nmol $min^{-1}$ $mg^{-1}$, which is orders of magnitude higher than that reported for purified enzyme preps from *Flaveria* (0.27 nmol $min^{-1}$ $mg^{-1}$) (see FIG. 10).

5.2 Cloning of Alcohol Dehydrogenase (ADH), Cinnamate 4-Hydroxylase (CH) and Phenylalanine Ammonia Lyase (PAL) from *Zostera marina*

All the genes were cloned by TA TOPO cloning method (Invitrogen) with the PCR products obtained using Taq polymerase, a cDNA library from *Zostera marina* and degenerate primers designed from the conserved regions among known sequences from vascular plants. The primer sequences and their corresponding conserved protein sequences are listed in FIG. 11. The approximate size of the targeted gene and the size of the of partial clone obtained are summarized in FIG. 12. The sequencing gel electrophoresis of the positive clones was performed by Research Genetics Inc. (Huntsville, Ala.) and the resulting sequences were analyzed using Lasergene System (DNAStar Inc.).

The initial PCR products for ADH gene(s) were obtained using primer Z-ADH-P1 and Z-ADfl-P5, which exhibited a single banding pattern on agarose gels. The PCR products, after being cloned onto pCR2.1 vector, were subjected to sequencing and analysis. The results revealed that they are identical products and contain a continuous open reading frame of approximately 940 bp (FIG. 13). The sequence exhibited high homology to *Arabidopsis thaliana* and Maize ADH genes (77–83% identity at protein sequence level; see FIG. 14), demonstrating that this sequence is part of an ADH gene from *Z. marina*. It also shares 48% homology with an ADM gene from *Escherichia coli*.

For cloning CH gene(s), primer Z—CH—P1 and Z—CH—P4 were used. Sequence analysis of the clones from the resulting PCR products shows that they contain a DNA fragment of 1085 bp (FIG. 15). An alignment of the translated protein sequence of the fragment with Citrus senensis and kidney bean CH genes show that they have a high level of homology (60–80% identity, see FIG. 16), confirming that these clones are partial cDNA clones of CH from *Z. marina*.

The PAL clones were obtained by the same method used for cloning ADH and CH, using primer Z-PAL-P1 and Z-PAL-P4. Analysis of the sequence data revealed that these clones contain an insert of 912 bp (FIG. 17). The deduced amino acid sequence of the DNA fragment exhibits 78–81% identity with PAL genes from *A. thaliana* and wheat, verifying that this DNA fragment is a part of PAL gene from *Z. marina* (see FIG. 18). In addition, the sequence shows only 20% identity with human PALs.

5.3 Crop Protection using Ectopic Zosteric Acid

The infection of crop plants by fungal and other pathogens involves a multi-step process which includes spore adhesion, germination, and the formation of infection structures and vehicles. FIG. 19 depicts several steps in fungal infection which may be targeted by one or more of the transgenic strategies of the invention. FIG. 20 shows microscopically the infection process for Colletotrichum. FIG. 21 (A and B) summarizes a number of known plant pathogenic fungi, the popular names of the diseases they cause, and the crop plant types that they infect.

Zosteric acid (ZA) inhibits attachment of a wide range of organisms including bacteria, yeast, algal and fungal spores, and invertebrate larvae. Epifend is non-toxic synthetic Zosteric Acid salt which was utilized to determine the efficacy of topical administration in preventing "fouling" or infection of a number of crop plants by a number of pathogenic organisms. Studies demonstrated that Epifend was particularly useful in inhibiting fungal spore attachment, and was effective at a does of ≦0.2% (wt/v) for broad range of pathogens and plant species. In these studies, no phytotoxicity was observed at dosages as great as 10× effective concentration. Furthermore, this compound is not likely to generate pathogen resistance and I readily biodegradable to simple end-products.

In initial studies conducted with Epifend, synthetic ZA, in vitro assays in polystyrene plates or 96-well plates were utilized. Several concentrations of the compounds were examined—no attempt was made to conduct detailed dosage response. Typically $10^4–10^6$ spores $mL^{-1}$ were used for inoculations. In some cases on plants, 0.025% Tween 80 was used as a wetter, while for potatoes Agarol™ (0.015%) was used and Kinetic™ for apples. Experiments were typically run in triplicate, and in almost all cases complete experiments were replicated. The results indicate that Epifend is a broad-spectrum anti-fungal activity which is non-fungicidal and non-fungistatic. Initial studies indicate that topical administration of Epifend targets the initial spore adhesion and subsequent recognition and surface attachments events required for infection structure formation. Studies indicate that Epifend is effective against ascomycete, basidiomycete and oomycete pathogens. FIG. 22 summarizes some of the results obtained to date using various fungal pathogens. The data shows effective dosage at ≦0.2% and no phytotoxicity at concentrations 5–10× above effective levels Another assay, using spore Adhesion on Polystyrene, indicates that Epifend inhibits adhesion of Colletotrichum spores to polystyrene, while coumaric acid did not inhibit spore adhesion in this assay (see FIG. 23). Epifend does not inhibit Colletotrichum mycelial growth in liquid culture at levels 1% or less (data not shown). Epifend also inhibits spore adhesion to glass, polystyrene and leaf surfaces, at concentrations as low as 0.01% (FIGS. 24 and 26). Epifend (at 0.1%) does not affect germination but reduces appressorial initiation and infection vesicle formation. Furthermore, Epifend (0.1%) delays plant disease development, while Epifend (at 1%) reduces germination. Epifend at ≦1% does not inhibit hyphal growth. Accordingly, the data support a non-fungicidal/non-fungistatic mode-of-action of Epifend.

Further studies indicate that Epifend blocks apressoria formation. FIG. 25 depicts the infection of rice blast by *Magnaporthe grisea*. Epifend (0.1%) does not affect germination in vitro but fully eliminates appressorium formation on polystyrene (FIG. 27). Studies in which Epifend was applied to leaves indicate that appressoria formed by germinated spores on control rice leaf, while Epifend-treated rice leaf had ungerminated spores (FIG. 27). Further rice plant studies indicate that Epifund reduces lesions in spot-inoculated as well as spray-inoculated rice leaves. Rice blast studies indicate that Epifend (at 0.1%) block spores adhesion in vitro and on leaves, Epifend (at <1%) has little effect on spore germination. Epifend (at 0.1%) fully blocks appressoria formation in vitro and on leaves. In leaf spot assays, Epifend (at 0.2%) fully prevents lesion formation (see FIG. 28). In leaf sprays, Epifend (at 0.1–1%) prevented lesion formation, In conclusion, all data support a non-fungicidal/non-fungistatic mode-of-action of Epifend on rice blast.

Further studies indicate that Epifend controls apple scab, *Venturia inaequalis*, an extremely aggressive pathogen which, in the 2000 season New England growing season, caused the worst apple scab infestation in recorded history. Infection by *Venturia inaequalis* occurs during blossom stage and is manifested on the flowers, leaves and fruits. Studies indicate that Epifend controls apple scab (at 0.2%) as effectively as a commercial fungicide (Dithane or Mancozeb) (data not shown). Initial studies indicate that Epifend does not control powdery mildew under "dry" conditions, however, in post-harvest applications, Epifend controls the ascomycete pathogens, *Penicillium digtatum, P. italicum* and *Colletotrichum gleosporioides*, which play an important role in post harvest fruit diseases. Epifend (at 0.2–0.5%) shows greatest efficacy on non-wounded fruits (results not shown).

Still further studies addressed the efficacy of Epifend in treating potato Late blight which is caused by *Phytophthora infestans*, a very aggressive oomycete pathogen. *P. infestans* rapidly destroys potato crops. Pathogen resistance and more than 20 identified resistant strains has caused a recurrence of losses due to this disease worldwide. A greenhouse trial was conducted by the Scottish Crops Research Institute (SCRI) on 2 cultivars and two doses. The trial results indicate that the heavy infection seen in control plants. 1% Epifend reduced infection in Bintje to a few percent while 0.2% reduced disease to approximately 10% (FIGS. 29 and 30).

Equivalents

Those skilled in the art will recognize, or be able to ascertain using no more than routine experimentation, many equivalents of the specific embodiments of the invention described herein. Such equivalents are intended to be encompassed by the following claims.

We claim:

1. An isolated nucleic acid which hybridizes under stringent conditions including a wash step in 0.2×SSC at 65° C. to a nucleic acid consisting of the nucleotide sequence set forth in SEQ ID NO: 15, wherein the isolated nucleic acid encodes a protein having sulfotransferase activity.

2. An isolated nucleic acid encoding a polypeptide comprising an amino acid sequence having at least 95% identity with SEQ ID NO: 16, wherein the polypeptide has a sulfotransferase activity.

3. The isolated nucleic acid of claim 2, encoding a polypeptide comprising an amino acid sequence having at least 99% identity with SEQ ID NO: 16.

4. The isolated nucleic acid of claim 2, encoding a polypeptide comprising the amino acid sequence set forth in SEQ ID NO: 16.

5. The isolated nucleic acid of claim 2, encoding a polypeptide consisting of the amino acid sequence set forth in SEQ ID NO: 16.

6. The isolated nucleic acid of claim 1, wherein the nucleic acid comprises the nucleotide sequence set forth in SEQ ID NO: 15.

7. The isolated nucleic acid of claim 1, consisting of the nucleotide sequence set forth in SEQ ID NO: 15.

8. A vector comprising the nucleic acid of claim 2.

9. A vector comprising the nucleic acid of claim 1.

10. A vector comprising the nucleic acid of claim 3.

11. An expression vector comprising the nucleic acid of claim 2.

12. An expression vector comprising the nucleic acid of claim 1.

13. An expression vector comprising the nucleic acid of claim 3.

14. A cell comprising the vector of claim 11.

15. The cell of claim 14, which is a prokaryotic cell.

16. The cell of claim 14, which is an eukaryotic cell.

17. A cell comprising the vector of claim 12.

18. The cell of claim 17, which is a prokaryotic cell.

19. The cell of claim 17, which is an eukaryotic cell.

20. A cell comprising the vector of claim 13.

21. The cell of claim 20, which is a prokaryotic cell.

22. The cell of claim 20, which is an eukaryotic cell.

23. A plant comprising a heterologous nucleic acid of claim 2.

24. The plant of claim 23, wherein the plant is a monocotyledon.

25. The plant of claim 23, wherein the plant is a dicotyledon.

26. A plant comprising a heterologous nucleic acid of claim 1.

27. The plant of claim 26, wherein the plant is a monocotyledon.

28. The plant of claim 26, wherein the plant is a dicotyledon.

29. A plant comprising a heterologous nucleic acid of claim 3.

30. The plant of claim 29, wherein the plant is a monocotyledon.

31. The plant of claim 29, wherein the plant is a dicotyledon.

* * * * *